(12) United States Patent
Bower et al.

(10) Patent No.: US 7,943,768 B2
(45) Date of Patent: May 17, 2011

(54) PIPERAZINE COMPOUNDS USEFUL AS ANTAGONISTS OF C-C CHEMOKINES (CCR2B AND CCR5) FOR THE TREATMENT OF INFLAMMATORY DISEASES

(75) Inventors: Justin Fairfield Bower, Cheshire (GB); Peter Wedderburn Kenny, Cheshire (GB); Jeffrey Philip Poyser, Cheshire (GB)

(73) Assignee: AstraZeneca AB, Södertälje (SE)

( * ) Notice: Subject to any disclaimer, the term of this patent is extended or adjusted under 35 U.S.C. 154(b) by 135 days.

(21) Appl. No.: 12/158,248

(22) PCT Filed: Dec. 18, 2006

(86) PCT No.: PCT/GB2006/004732
§ 371 (c)(1),
(2), (4) Date: Jun. 19, 2008

(87) PCT Pub. No.: WO2007/071952
PCT Pub. Date: Jun. 28, 2007

(65) Prior Publication Data
US 2008/0287453 A1 Nov. 20, 2008

(30) Foreign Application Priority Data
Dec. 21, 2005 (GB) .................................. 0525957.7

(51) Int. Cl.
| C07D 239/72 | (2006.01) |
| C07D 403/00 | (2006.01) |
| C07D 401/00 | (2006.01) |
| C07D 413/00 | (2006.01) |
| C07D 417/00 | (2006.01) |
| C07D 419/00 | (2006.01) |
| C07D 405/00 | (2006.01) |
| C07D 409/00 | (2006.01) |
| C07D 295/00 | (2006.01) |
| C07D 411/00 | (2006.01) |
| C07D 213/46 | (2006.01) |
| C07D 211/60 | (2006.01) |

(52) U.S. Cl. ........ 544/292; 544/295; 544/359; 544/360; 544/362; 544/363; 544/364; 544/367; 544/368; 544/370; 544/374; 544/388; 546/252.16; 546/252.17; 546/252.18; 546/245; 546/315; 546/277; 546/254.06; 546/254.04; 546/253.01; 546/253.04; 546/253.05; 546/253.06; 546/253.13

(58) Field of Classification Search .................. 514/277, 514/315, 245, 252.16, 252.17, 252.18, 253.01, 514/253.04, 253.05, 253.06, 253.13, 254.06, 514/254.04; 544/295, 292, 363, 362, 368, 544/364, 359, 360, 370, 388, 367, 374
See application file for complete search history.

(56) References Cited

U.S. PATENT DOCUMENTS

| 5,442,064 A | 8/1995 | Pieper et al. |
| 6,060,472 A * | 5/2000 | Karimian et al. .......... 514/253.1 |
| 6,492,368 B1 | 12/2002 | Dorsch et al. |
| 7,371,753 B2 | 5/2008 | Stadtmueller et al. |
| 2004/0077655 A1 | 4/2004 | Dartois et al. |
| 2004/0082589 A1 | 4/2004 | Farina et al. |
| 2006/0063767 A1 | 3/2006 | Javaid et al. |
| 2007/0161634 A1 | 7/2007 | Pei et al. |
| 2009/0099156 A1 | 4/2009 | Bower et al. |
| 2010/0152197 A1 | 6/2010 | Cumming et al. |

FOREIGN PATENT DOCUMENTS

| EP | 0592949 | 4/1994 |
| EP | 0563345 | 7/2002 |
| WO | WO 99/09984 | 3/1999 |
| WO | 9916751 | 4/1999 |
| WO | WO 99/51584 | 10/1999 |
| WO | WO 00/35878 | * 12/1999 |
| WO | WO 00/59502 | 10/2000 |
| WO | WO 02/069973 | 9/2002 |
| WO | WO 2004/035549 | * 4/2004 |
| WO | WO 2004/050024 | 6/2004 |
| WO | WO 2005/087746 | * 9/2005 |
| WO | WO 2005/121123 | 12/2005 |
| WO | WO 2005/123697 | 12/2005 |
| WO | WO 2006/021548 | 3/2006 |
| WO | WO 2006/067401 | 6/2006 |
| WO | WO 2007/003604 | * 1/2007 |

OTHER PUBLICATIONS

Lu, et al., Cloning and Functional Characterization of the Rabbit C-C Chemokine Receptor 2, BMC Immunology, 6:15 (2005).*
K. Peter C. Vollhardt and Neil E. Schore "Properties and reactions of haloalkanes" Organic Chemistry: Structure and Function, Fourth Edition, 224-225 (2002).
Zaragoza et al. "1-Alkyl-4-acylpiperazines as a new class of imidazole-free histamine H3 receptor antagonists" J. Med. Chem., 47(11):2833-2838 (2004).
Castonguay et al. "Binding of 2-Aryl-4-(piperidin-1-yl)butanamines and 1,3,4-trisubstituted pyrrolidines to human CCR5: A molecular modeling-guided mutagenesis study of the binding pocket" Biochemistry, 42(6):1544-1550 (2003).

(Continued)

*Primary Examiner* — James O Wilson
*Assistant Examiner* — Erich A Leeser
(74) *Attorney, Agent, or Firm* — Connolly Bove Lodge & Hutz LLP

(57) ABSTRACT

A compound of formula (I)

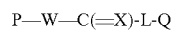

wherein P is an optionally substituted aryl or heteroaryl group; W is an optionally substituted 6 or 7-membered aliphatic ring comprising ring atoms $Y^1$ and $Y^2$ independently selected from Oxygen and Nitrogen, X is selected from Oxygen, Nitrogen and Sulphur; L is an optional $C_{1-4}$ linker; and Q is an optionally substituted 4-7 membered aliphatic ring: for use in the treatment of chemokine mediated diseases or disorders.

10 Claims, No Drawings

OTHER PUBLICATIONS

Hale et al. "1,3,4-Trisubstituted pyrrolidine CCR5 receptor antagonists. Part 2: lead optimization affording selective, orally bioavailable compounds with potent Anti-HIV activity" Bioorganic & Medicinal Chemistry Letters, 11(20):2741-2745 (2001).

Purandare et al. "Optimization of CCR4 antagonists: Side-chain exploration" Bioorganic & Medicinal Chemistry Letters, 16(1): 204-207 (2005).

Shen et al. "Antagonists of human CCR5 receptor containing 4-(pyrazolyl)piperidine side chains. Part 2: Discovery of potent, selective, and orally bioavailable compounds" Bioorganic & Medicinal Chemistry Letters, 14(4):941-945 (2004).

Office Action issued in counterpart European Patent App. No. 06831403.8 (EP1966187) on Apr. 20, 2009.

McDermott et al., "First example of s-BuLi/(-)-Sparteine-Mediated Chiral Deprotonation of a Piperazine and Proof of the Sense of Induction," Synlett, 2008, vol. 6, pp. 875-879.

Shiozawa et al., "Antivertigo Agents. I. Structure-Activity Relationships of 2-(2-Aminoethyl)pyridines," Chem. Pharm. Bull., 1984, vol. 32(2), pp. 553-563.

International Search Report and Written Opinion issued for PCT/GB2006/004732 on Mar. 21, 2007.

Notice of allowance issued for U.S. Appl. No. 11/793,606, filed Jun. 21, 2010.

Notice of allowance issued for U.S. Appl. No. 11/793,606, filed Oct. 19, 2010.

* cited by examiner

PIPERAZINE COMPOUNDS USEFUL AS ANTAGONISTS OF C-C CHEMOKINES (CCR2B AND CCR5) FOR THE TREATMENT OF INFLAMMATORY DISEASES

RELATED APPLICATIONS

The present application is a U.S. National Phase Application of International Application No. PCT/GB2006/004732 (filed Dec. 18, 2006) which claims the benefit of Great Britain Patent Application No. 0525957.7 (filed Dec. 21, 2005), both of which are hereby incorporated by reference in their entirety.

The present invention relates to pharmaceutical compositions which comprise compounds that act via antagonism of the CCR2b receptor for which MCP-1 is one of the known ligands and so may be used to treat inflammatory disease which is mediated by these receptors. These compounds contain a cyclic aromatic moiety. The invention further relates to novel compounds for use in the compositions, to processes for their preparation, to intermediates useful in their preparation and to their use as therapeutic agents.

Chemokines play an important role in immune and inflammatory responses in various diseases and disorders, including rheumatoid arthritis, chronic obstructive pulmonary disease, atherosclerosis and other autoimmune pathologies such as inflammatory bowel disease, diabetes, asthma and allergic diseases. Chemokines also have a role in angiogenesis and modulation of chemokines may be beneficial in the treatment of cancer. Chemokines are small secreted molecules belonging to a growing superfamily of 8-14 kDa proteins characterised by a conserved four cysteine motif. The chemokine superfamily can be divided into two main groups exhibiting characteristic structural motifs, the Cys-X-Cys (C—X—C) and Cys-Cys (C—C) families. These are distinguished on the basis of a single amino acid insertion between the NH-proximal pair of cysteine residues and sequence similarity.

The C—C chemokines include potent chemoattractants of monocytes and lymphocytes such as monocyte chemoattractant proteins 1-3 (MCP-1, MCP-2 and MCP-3), RANTES (Regulated on activation, Normal T expressed and Secreted), eotaxin and the macrophage inflammatory proteins 1α and 1β (MIP-1α and MIP-1β).

The C—X—C chemokines include several potent chemoattractants and activators of neutrophils such as interleukin-8 (IL-8) and neutrophil-activating peptide 2 (NAP-2).

Studies have demonstrated that the actions of chemokines are mediated by subfamilies of G-protein coupled receptors, among which there are the receptors designated CCR1, CCR2, CCR2A, CCR2B, CCR3, CCR4, CCR5, CCR6, CCR7, CCR8, CCR9, CCR10, CXCR1, CXCR2, CXCR3, CXCR4, CXCR5 and CX3CR1. These receptors represent good targets for drug development since agents which modulate these receptors would be useful in the treatment of disorders and diseases such as those mentioned above.

The applicants have found a class of compounds containing a cyclic moiety which has useful antagonism of C—C chemokine receptors and in particular of the CCR2b receptor.

WO-02/069973 discloses piperidine-piperazine compounds useful as ligands of neurotransmitter receptors.

Purandare et al in Bioorganic & Medicinal Chemistry Letters, 2005, 16, 204-207 disclose substituted piperazine compounds useful as CCR4 antagonists. The most preferred compound 8c showed >1000-fold selectivity against inter alia the CCR2 chemokine receptor.

The present invention now provides a compound of Formula I

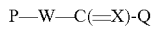  (I)

wherein

P is a monocyclic or bicyclic $C_{5-10}$ aryl or heteroaryl group of up to 20 ring atoms, each of which is optionally substituted by 1, 2 or 3 substituents independently selected from halogen, $C_{1-4}$ alkyl, $C_{3-6}$ cycloalkyl, $C_{2-4}$ alkenyl or $C_{2-4}$ alkynyl, cyano, phenyl, phenoxy, —O—$C_{1-4}$ alkyl, $C_{1-4}$ thioalkyl, carboxy, carboxy $C_{1-4}$ alkyl, —$SO_2CH_3$, $C_{1-4}$ alkylamino and $NO_2$; and wherein $C_{1-4}$ alkyl, —O—$C_{1-4}$ alkyl, or $C_{1-4}$ thioalkyl is optionally substituted by one or more fluorine atoms and wherein the phenyl or phenoxy substituent may in turn be substituted by 1, 2, or 3 of the other substituents listed above for P;

W is a 6- or 7-membered aliphatic ring comprising ring atoms $Y^1$ and $Y^2$ and linked by $Y^1$ and $Y^2$ to groups P and C(=X) respectively, $Y^1$ is N or C and $Y^2$ is N and wherein (i) where $Y^1$ and $Y^2$ are both N then W is optionally substituted on any ring carbon atom by a group independently selected from $C_{1-4}$ alkyl, =O and halogen, and (ii) where $Y^1$ is C and $Y^2$ is N then $Y^1$ is optionally substituted by hydroxy, $C_{1-4}$ alkyl or halogen; and/or the aliphatic ring may optionally have a hydroxy substituent vicinal to $Y^1$ and on any ring carbon atom a substituent independently selected from $C_{1-4}$ alkyl, =O and halogen and the aliphatic ring may also comprise one carbon-carbon double bond adjacent to $Y^1$;

X is O, or two hydrogen atoms each linked by a single bond to the carbon atom in —C(=X)—; and where $Y^2$ is carbon then —C(=X)— can also represent —O—, —S— or —NR— wherein R represents hydrogen or $C_{1-4}$ alkyl;

Q is a 4-7 membered aliphatic ring comprising one nitrogen atom and as a further optional ring member an N, O or S atom or a SO or $SO_2$ group and Q is linked to —C(=X)— via a ring carbon atom, such aliphatic ring being substituted on one or more nitrogen atoms by (i) a $C_{1-6}$ alkyl, $C_{3-6}$ cycloalkyl or $C_{1-4}$ alkenyl group each of which may be further optionally substituted by difluoromethyl, trifluoromethyl, a monocyclic aliphatic or (hetero)aromatic ring of up to 7 ring atoms and comprising up to 3 heteroatoms each independently selected from N, O or S and the ring being optionally substituted by 1, 2 or 3 substituents independently selected from halogen, $C_{1-4}$ alkyl, cyano, —O—$C_{1-4}$ alkyl, $C_{1-4}$ thioalkyl, —$SO_2CH_3$, $C_{1-4}$ alkylamino and $NO_2$; and wherein $C_{1-4}$ alkyl, —O—$C_{1-4}$ alkyl, or $C_{1-4}$ thioalkyl is optionally substituted by one or more fluorine atoms;

(ii) a monocyclic (hetero)aliphatic or (hetero)aromatic ring of up to 7 ring atoms and comprising up to three heteroatoms each independently selected from N, O or S and the ring being optionally substituted by 1, 2 or 3 substituents independently selected from halogen, $C_{1-4}$ alkyl, cyano, —O—$C_{1-4}$ alkyl, $C_{1-4}$ thioalkyl, —$SO_2CH_3$, $C_{1-4}$ alkylamino and $NO_2$; and wherein $C_{1-4}$ alkyl, —O—$C_{1-4}$ alkyl, or $C_{1-4}$ thioalkyl is optionally substituted by one or more fluorine atoms;

(iii) a (hetero)aryl-$C_{1-4}$ alkyl group comprising up to 12 ring atoms of which up to 3 may be heteroatoms independently selected from N, O and S, such group being optionally substituted by up to 3 substituents independently selected from halogen, $C_{1-4}$ alkyl, $C_{2-4}$ alkenyl or $C_{2-4}$ alkynyl, cyano, phenyl, phenoxy, $C_{1-4}$ thioalkyl, carboxy $C_{1-4}$ alkyl, —$SO_2CH_3$ and $NO_2$; and wherein $C_{1-4}$ alkyl, —O—$C_{1-4}$ alkyl, or $C_{1-4}$ thioalkyl is optionally substituted by one or more fluorine atoms and wherein the phenyl or phenoxy substituent may in turn be substituted by 1, 2, or 3 of the other substituents listed above;

(iv) a straight or branched chain alkyl group of up to 8 carbon atoms optionally comprising a double or treble carbon-carbon bond and further optionally substituted by up to 3 substituents independently selected from hydroxy, $CF_3$, $C_{3-7}$ cycloalkyl or —$NR^1R^2$ wherein $R^1$ and $R^2$ are independently selected from hydrogen or any ring substituent listed hereinbefore for Q;

or the aliphatic ring is (i) mono- or di-substituted on one or more ring carbon atoms by halogen, —CN or a $C_{1-4}$ alkyl group which is optionally substituted by hydroxy or a —O—$C_{1-4}$ alkyl group, and/or (ii) disubstituted on a ring carbon atom by $C_{1-4}$ alkyl groups or by a single spiro group having up to 7 ring atoms one of which is optionally O, S, or N, such groups being optionally substituted by a hydroxyl or a —O—$C_{1-4}$ alkyl group and/or (iii) disubstituted on a ring carbon atom by a hydroxy group and a monocyclic heteroaromatic ring of up to 7 ring atoms and comprising up to three heteroatoms each independently selected from N, O or S; and provided that (i) where Q is piperidine, X is O and the piperidine ring nitrogen is substituted by cyclopropyl then P is not unsubstituted 2-pyridyl, unsubstituted 2-pyrazinyl or substituted phenyl, 2-pyridyl, 4-pyridyl, 4-pyridyl fused to another ring, or 4-pyrimidyl wherein in each case the substituent is a single ortho methoxy, trifluoromethyl or cyano substituent;

or a pharmaceutically acceptable salt or solvate thereof.

Compounds of formula (I) can be used in the treatment of diseases in which the chemokine receptor belongs to the C—C receptor subfamily, more preferably the target chemokine receptor is the CCR2 receptor.

CCR2 is a receptor for the Monocyte chemoattractant protein-1 (MCP-1). MCP-1 is a member of the chemokine family of pro-inflammatory proteins which mediate leukocyte chemotaxis and activation. MCP-1 is a C—C chemokine which is potent T-cell and monocyte chemoattractant. MCP-1 has been implicated in the pathophysiology of a large number of inflammatory diseases including rheumatoid arthritis, chronic obstructive pulmonary disease, atherosclerosis and inflammatory bowel disease.

MCP-1 acts through the CCR2 receptor. MCP-2, MCP-3 and MCP-4 may also act, at least in part, through this receptor. Therefore in this specification, when reference is made to "inhibition or antagonism of MCP-1" or "MCP-1 mediated effects" this includes inhibition or antagonism of MCP-2 and/or MCP-3 and/or MCP-4 mediated effects when MCP-2 and/or MCP-3 and/or MCP-4 are acting through the CCR2 receptor.

In addition we have found that certain compounds of formula (I) modulate the function of the CCR5 receptor. The CCR5 receptor is expressed on T-lymphocytes, monocytes, macrophages, dendritic cells, microglia and other cell types. These detect and respond to several chemokines, principally "regulated on activation normal T-cell expressed and secreted" (RANTES), macrophage inflammatory proteins (MIP) MIP-1α and MIP-1β and monocyte chemoattractant protein-2 (MCP-2).

This results in the recruitment of cells of the immune system to sites of disease. In many diseases it is the cells expressing CCR5 which contribute, directly or indirectly, to tissue damage. Consequently, inhibiting the recruitment of these cells is beneficial in a wide range of diseases.

CCR5 is also a co-receptor for HIV-1 and other viruses, allowing these viruses to enter cells. Blocking the receptor with a CCR5 antagonist or inducing receptor internalisation with a CCR5 agonist protects cells from viral infection.

Conveniently in the compounds of formula I each of the substituents is selected independently from the values set out below, or any combination thereof:

P is a monocyclic or bicyclic $C_{5-10}$ aryl group or a heteroaryl group of up to 12 ring atoms, each of which is optionally substituted by 1 or 2 substituents independently selected from halogen, $C_{1-4}$ alkyl, $C_{3-6}$ cycloalkyl, $C_{2-4}$ alkenyl or $C_{2-4}$ alkynyl, cyano, phenyl, phenoxy, —O—$C_{1-4}$ alkyl, $C_{1-4}$ thioalkyl, carboxy, carboxy $C_{1-4}$ alkyl, —$SO_2CH_3$, $C_{1-4}$ alkylamino and $NO_2$; and wherein $C_{1-4}$ alkyl, —O—$C_{1-4}$ alkyl, or $C_{1-4}$ thioalkyl is optionally substituted by one or more fluorine atoms and wherein the phenyl or phenoxy substituent may in turn be substituted by 1, 2, or 3 of the other substituents listed above for P;

W is a 6-membered aliphatic ring comprising ring atoms $Y^1$ and $Y^2$ and linked by $Y^1$ and $Y^2$ to groups P and C(=X) respectively, $Y^1$ and $Y^2$ are independently selected from N and C and wherein (i) where $Y^1$ and $Y^2$ are both N then W is optionally substituted on any ring carbon atom by a group independently selected from $C_{1-4}$ alkyl, =O and halogen, and (ii) where $Y^1$ is C and $Y^2$ is N then $Y^1$ is optionally substituted by hydroxy, $C_{1-4}$ alkyl or halogen; and/or the aliphatic ring may optionally have a hydroxy substituent vicinal to $Y^1$ and on any ring carbon atom a substituent independently selected from $C_{1-4}$ alkyl, =O and halogen and the aliphatic ring may also comprise one carbon-carbon double bond adjacent to $Y^1$;

X is O, or two hydrogen atoms each linked by a single bond to the carbon atom in —C(=X)—; and where $Y^2$ is carbon then —C(=X)— can also represent —O— or —S—;

Q is a 5 or 6-membered aliphatic ring comprising one nitrogen atom and as a further optional ring member an N, O or S atom or a SO or $SO_2$ group and Q is linked to —C(=X)— via a ring carbon atom, such ring being (i) optionally monosubstituted on one or more ring nitrogen atoms by a $C_{1-4}$ alkyl group which may be further optionally substituted by difluoromethyl, trifluoromethyl, a monocyclic aliphatic or (hetero)aromatic ring of up to 7 ring atoms and comprising up to three heteroatoms each independently selected from N, O or S and the ring being optionally substituted by 1, 2 or 3 substituents independently selected from halogen, $C_{1-4}$ alkyl, cyano, —O—$C_{1-4}$ alkyl, $C_{1-4}$ thioalkyl, —$SO_2CH_3$, $C_{1-4}$ alkylamino and $NO_2$, and wherein $C_{1-4}$ alkyl, —O—$C_{1-4}$ alkyl, or $C_{1-4}$ thioalkyl is optionally substituted by one or more fluorine atoms; and/or (ii) optionally monosubstituted on one or more ring nitrogen atoms by a monocyclic (hetero)aliphatic or (hetero)aromatic ring of up to 7 ring atoms and comprising up to three heteroatoms each independently selected from N, O or S and the ring being optionally substituted by 1, 2 or 3 substituents independently selected from halogen, $C_{1-4}$ alkyl, cyano, —O—$C_{1-4}$ alkyl, $C_{1-4}$ thioalkyl, —$SO_2CH_3$, $C_{1-4}$ alkylamino and $NO_2$; and/or (iii) Q is optionally substituted on one or more ring nitrogen atoms by a (hetero)aryl-$C_{1-4}$ alkyl group comprising up to 8 ring atoms of which up to 3 may be heteroatoms independently selected from N, O and S, such group being optionally substituted by up to 3 substituents independently selected from halogen, $C_{1-4}$ alkyl, $C_{2-4}$ alkenyl or $C_{2-4}$ alkynyl, cyano, phenyl, phenoxy, $C_{1-4}$ thioalkyl, carboxy $C_{1-4}$ alkyl, —$SO_2CH_3$ and $NO_2$, and wherein $C_{1-4}$ alkyl, —O—$C_{1-4}$ alkyl, or $C_{1-4}$ thioalkyl is optionally substituted by one or more fluorine atoms and wherein the phenyl or phenoxy substituent may in turn be substituted by 1, 2, or 3 of the other substituents listed above; and/or (iv) Q is optionally substituted on one or more ring nitrogen atoms by a straight or branched chain alkyl group of up to 8 (such as up to 6) carbon atoms optionally comprising a double or treble carbon-carbon bond and further optionally substituted by up to 2 substituents independently selected from hydroxy, $CF_3$, $C_{3-7}$ cycloalkyl or —$NR^1R^2$ wherein $R^1$ and $R^2$ are independently selected from hydrogen or any ring substituent listed hereinbefore for Q; and/or (v) optionally mono-substituted on one or more ring carbon atoms by halogen, —CN or a $C_{1-4}$ alkyl group which is optionally substituted by hydroxy or a —O—$C_{1-4}$ alkyl group, and/or (vi) optionally disubstituted on a ring carbon atom by $C_{1-4}$ alkyl groups or by a single spiro group having up to 5 carbon atoms, such groups being optionally substituted by a —O—$C_{1-4}$ alkyl group.

In further convenient compounds of Formula I each of the substituents is selected independently from the values set out below, or any combination thereof:

P is a phenyl or naphthyl or a heteroaryl group of up to 10 ring atoms such as phenyl, pyridyl (such as 2-pyridyl or 4-pyridyl), quinolyl (such as 2-quinolyl or 4-quinolinyl), quinazolinyl (such as 2-quinazolinyl), quinoxalinyl (such as 2-quinoxalinyl), pyrazinyl (such as 2-pyrazinyl); 1,8-naphthyridinyl (such as 2-(1,8-naphthyridinyl)) each of which is optionally substituted by 1 or 2 substituents independently selected from halogen, $C_{1-4}$ alkyl (such as methyl, ethyl or isopropyl), cyano, $C_{1-4}$ alkyl or $C_{1-4}$ alkoxy optionally substituted by up to 3 halogen atoms, phenyl, phenoxy, —O—$C_{1-4}$ alkyl (such as methoxy or ethoxy), $C_{1-4}$ thioalkyl (such as methylthio or ethylthio), —$SO_2CH_3$, $C_{1-4}$ alkylamino (such as methylamino or ethylamino) and $NO_2$; and wherein the phenyl or phenoxy substituent may in turn be substituted by or 1 or 2 of the other substituents listed above for P;

W is a piperazine or homopiperazine ring optionally substituted on any ring carbon atom by a group independently selected from $C_{1-4}$ alkyl, =O and halogen, or W is a piperidine ring optionally substituted on the carbon atom linking the ring to P by hydroxy, $C_{1-4}$ alkyl, or halogen and on any other ring atom an optional substituent selected from $C_{1-4}$ alkyl, =O and halogen; and the ring may also have a double bond adjacent to the carbon atom linking the ring to P;

X is O, or two hydrogen atoms each linked by a single bond to the carbon atom in —C(=X)—;

Q is a piperazinyl, piperidinyl or pyrrolidinyl ring and linked to —C(=X)— via a ring carbon atom, such ring being optionally monosubstituted on one or more ring nitrogen atoms by a methyl, ethyl, isopropyl or cyclopropyl group each of which may be further optionally substituted by phenyl itself optionally mono- or di-substituted by $C_{1-4}$ alkyl, $C_{1-4}$ alkyl optionally substituted by up to 3 halogen atoms, or halogen;

and/or optionally substituted on one or more ring nitrogen atoms by a straight or branched chain alkyl group of up to 4 carbon atoms optionally comprising a double or treble carbon-carbon bond and further optionally substituted by up to 2 substituents independently selected from hydroxy and —$NR^1R^2$ wherein $R^1$ and $R^2$ are independently selected from hydrogen or any ring substituent listed above for Q;

and/or optionally mono-substituted on one ring carbon atoms by a $C_{1-4}$ alkyl group.

Further convenient compounds are where X is oxygen and Q represents a substituted aliphatic ring comprising two nitrogen atoms; X is two hydrogen atoms each linked by a single bond to the carbon atom in —C(=X) and Q represents a substituted aliphatic ring comprising a single nitrogen atom.

As used herein, the term "heteroatom" refers to non-carbon atoms such as oxygen, nitrogen or sulphur atoms.

The term 'alkyl' when used either alone or as a suffix includes straight chain and branched structures. These groups may contain up to 10, conveniently up to 6 and more conveniently up to 4 carbon atoms. Similarly the terms "alkenyl" and "alkynyl" refer to unsaturated straight or branched structures containing for example from 2 to 10, preferably from 2 to 6 carbon atoms. Cyclic moieties such as cycloalkyl or cycloalkenyl are similar in nature but have at least 3 carbon atoms. They may be bridged. Terms such as "alkoxy" and "alkanoyl" comprise alkyl moieties as defined above, attached to the appropriate functionality.

The term "halo" includes fluoro, chloro, bromo and iodo. References to aryl groups include aromatic carbocylic groups such as phenyl and naphthyl.

The term "and wherein $C_{1-4}$ alkyl, —O—$C_{1-4}$ alkyl, or $C_{1-4}$ thioalkyl is optionally substituted by one or more fluorine atoms" means that in such groups up to 7, such as up to 5, up to 3, up to 2 or 1 hydrogen atoms may be replaced by fluorine atoms. Convenient examples of such groups include difluoromethyl, trifluoromethyl, and trifluoromethoxy.

The term "heterocyclyl" includes aromatic or non-aromatic rings, or partially unsaturated ring systems, for example containing from 4-20, such as up to 10 ring atoms, or containing 5-10 ring atoms such as 5-7 ring atoms, at least one of which is a heteroatom such as oxygen, sulphur or nitrogen. Rings may be mono-, bi- or tricyclic. They may also contain bridges, in particular alkyl bridges. Examples of such groups include furyl, thienyl, pyrrolyl, pyrrolidinyl, imidazolyl, thiazolyl, tetrazolyl, oxazolyl, isoxazolyl, pyrazolyl, pyridyl, pyrimidinyl, pyrazinyl, pyridazinyl, triazinyl, quinolinyl, iosquinolinyl, quinoxalinyl, benzthiazolyl, benzoxazolyl, benzothienyl, benzofuranyl, tetrahydrofuryl, chromanyl, piperidinyl, 1,2,3,4-tetrahydroquinolinyl, 1,2,3,4-tetrahydroisoquinolinyl, piperazinyl, quinoxalinyl, quinazolinyl, cinnolinyl, indolyl, indolinyl, benzimidazolyl, indazolyl, oxazolyl, benzoxazolyl, isoxazolyl, morpholinyl, dioxolane, benzodioxolane, 4H-1,4-benzoxazinyl, 4 H-1,4-benzothiazinyl, 1,2,3-triazolyl, 1,2,4-triazolyl, oxadiazolyl, furazanyl, thiadiazolyl, dibenzofuranyl, dibenzothienyl oxiranyl, oxetanyl, azetidinyl, oxepanyl, oxazepanyl, tetrahydro-1,4-thiazinyl, 1,1-dioxotetrahydro-1,4-thiazinyl, homopiperidinyl, homopiperazinyl, dihydropyridinyl, tetrahydropyridinyl, dihydropyrimidinyl, tetrahydropyrimidinyl, tetrahydrothienyl, tetrahydrothiopyranyl or thiomorpholinyl.

"Heteroaryl" refers to those heterocyclyl groups described above which have an aromatic character. The term "aralkyl" refers to aryl substituted alkyl groups such as benzyl. The terms "aryl" and "heteroaryl" include non-condensed ring systems such as biphenyl.

Other expressions used in the specification include "hydrocarbyl" which refers to any structure comprising carbon and hydrogen atoms. For example, these may be alkyl, alkenyl, alkynyl, aryl, aralkyl, cycloalkyl or cycloalkenyl.

The compounds of Formula I may be prepared as follows:

Route A by reaction of a compound of Formula II with a compound of Formula III:

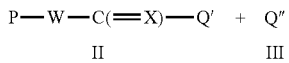

wherein P, W, and X are as defined in relation to Formula I, Q' is a 4-7 membered aliphatic ring as defined for Q but unsubstituted on ring nitrogen atoms, Q" comprises a nitrogen atom substituent as defined for Q in any one of (i), (ii), (iii), or (iv), and wherein Q' and Q" react to form Q, followed by the removal of any protecting groups if used.

Route A1 is a variant of Route A and is a reductive amination using a nitrogen atom on Q' for reaction with an electrophilic carbonyl group on Q".

In some cases, it is appropriate to carry out the reaction in the presence of an organic acid, such as acetic acid, in an alcoholic solvent, such as methanol, in particular where the carbonyl group is in the form of a protected precursor, such as a trimethylsilyl protected hemi-ketal. The reduction may be carried out with a suitable reductant, for example with a solution of sodium cyanoborohydride in tetrahydrofuran (THF) at elevated temperatures.

Alternatively, reaction can be carried out in an organic solvent such as dichloromethane, 1,2-dichloroethane or THF in the presence of a base such as N,N-diisopropylethylamine or triethylamine and an appropriately selected reductant such as sodium triacetoxyborohydride at ambient temperature.

Route A2 is a variant of Route A and is an alkylation reaction wherein the compound of Formula II, wherein P, W, and X are defined in relation to Formula I and Q' is as defined above, is reacted with a compound of Formula III, wherein Q" is as defined above (optionally followed by the removal of any protecting groups). Q" conveniently comprises a leaving group such as halogen or mesylate for reaction with the free nitrogen in Q' to yield Q.

The reaction is suitably effected in an organic solvent such as acetone and an alkali metal carbonate base, such as potassium carbonate at elevated temperatures. As an alternative to this method, the reaction is also suitably effected in an organic solvent such as N,N-dimethylformamide and an alkali metal carbonate base, such as potassium carbonate, at ambient temperature.

Route A3 is a variant of Route A and is the formation of an amide bond between a nitrogen of Q' and a carboxylic acid or derivative thereof comprised in Q" such as an acid halide (eg. Cl or Br) or an acid azide. The reaction is suitably effected in an organic solvent such as TlHF in the presence of a suitably chosen coupling reagent such as O-(7-Azabenzotriazol-1-yl)-N,N,N',N'-TetramethylUronium Hexafluorophosphate (HATU) and an organic base, such as N,N-diisopropylethylamine at ambient temperature The amide carbonyl is subsequently reduced using an appropriate reductant such as borane in an organic solvent such as tetrahydrofuran THF at elevated temperature to give Q.

Route B by interconversion of a compound of Formula I into another compound of formula I. For example where —C(═X)— is carbonyl then this may be reduced to —CH2— with an appropriate reductant such as borane in an organic solvent such as THF at elevated temperature.

Route C by reaction of a compound of Formula IV with a compound of Formula V

wherein P and W are as defined in relation to Formula I above, L is a leaving group and Q''' is an optionally protected form of Q comprising a carboxylic acid group or derivative thereof. Convenient derivatives include chloride, bromide or azide or other activated forms of the acid and protecting groups include t-Boc, benzyloxycarbonyl (Cbz) and benzyl, which protecting group is removed under suitable deprotection conditions which would be apparent to a skilled person, but may include treatment with an acid such as trifluoroacetic acid or (except for t-Boc) treatment with hydrogen in the presence of a catalyst, typically activated palladium on charcoal to provide the compounds of Formula I.

Convenient leaving groups include the conjugate bases of strong acids such as r (HI), $HSO_4^-$ ($H_2SO_4$), $Br^-$ (HBr), $Cl^-$ (HCl), $H_2O(H_3O^+)$, $CH_3SO_3^-$, ($CH_3SO_3H$); cf. pages 224-226 of "Organic Chemistry, Structure and Function", Ed. K. P. C. Vollhardt & N. E. Schore, Fourth Edition, W.H. Freeman & Co.

Route C1 is a variant of Route C and is an amide coupling using a nitrogen atom on W for reaction with a carboxylic acid or derivative comprised in Q'''. The reaction is suitably effected in an organic solvent such as THF, in the presence of a suitably chosen coupling reagent such as HATU and an organic base, such as N,N-diisopropylethylamine at ambient temperature. Where optional protection has been used, this may be removed using conditions apparent to a skilled person to obtain the compounds of Formula I, such may include treatment with an acid such as trifluoroacetic acid or (excepting t-Boc) treatment with hydrogen in the presence of a catalyst, typically activated palladium on charcoal to provide the compounds of Formula I.

Route D by reaction of a compound of Formula VI with a compound of Formula VII

wherein P, W, X are as defined in relation to Formula I, L is a leaving group and Q''' is as defined above, followed by the removal of any protecting groups if used.

Route D1 is a variant of Route D and is a displacement of the leaving group on P using a nitrogen on W i.e $Y^1$. The reaction is suitably effected in an organic solvent such as methanol and optionally catalysed by an acid such as concentrated hydrochloric acid at elevated temperatures, optionally carried out in a microwave vessel.

Intermediates

Compounds of the Formula II are novel and conveniently obtained by reacting compounds of Formula IV with compounds of Formula V

wherein P, W and X are as defined in relation to Formula I, L is a leaving group and Q''' is an optional protected variant of Q and comprises an carboxylic acid or derivative thereof such as an acid halide (eg. Cl or Br) or an acid azide Compounds of the Formula III are commercially available, from inter alia Aldrich Chemical Company, Inc., 3b Medical Systems, Inc. and Ennova MedChem Group, Inc.

Compounds of the Formula IV are commercially available, for example Aldrich Chemical Company, Inc. and Lancaster Synthesis, Limited. Alternatively, compounds of Formula IV can be conveniently obtained from compounds of Formula VI and VII, wherein P-L and W' are obtained from commercial sources, W' being a an optionally protected variant of W.

P—L                    VI

W'                      VIII

Compounds of the Formula V may be prepared from a suitable, optionally monoprotected compound available commercially by reaction with an organic halide, such as an alkyl, aralkyl, alkenyl or alkynyl halide. The reaction is suitably effected in an organic solvent such as ethanol in the presence of an alkali metal carbonate base, such as sodium carbonate at elevated temperatures and may be carried out either thermally or in a microwave vessel. Alternatively, the above monoprotected compound is reacted with a commercially available carbonyl compound. The reaction can be carried out in an organic solvent such as dichloromethane, 1,2-dichloroethane or THF in the presence of a base such as N,N-diisopropylethylamine or triethylamine and an appropriately selected reductant such as sodium triacetoxyborohydride at ambient temperature.

Compounds of the Formula VI are commercially available, for example from Aldrich Chemical Company Inc. and Lancaster Synthesis Limited.

Compounds of the Formula VII are novel and conveniently obtained by reacting compounds of Formula VIII with compounds of formula IX.

W'                      VIII

L—C(═X)—Q'''         IX wherein W' is as defined above and is commercially available for example from Aldrich Chemical Company Inc. The compound of Formula IX may comprise an aldehyde which in turn may be conveniently prepared from a suitably protected precursor which is commercially available, for example from Aldrich Chemical Company Inc.

Compounds of the Formula VIII are commercially available, for example from Aldrich Chemical Company Inc. and Lancaster Synthesis Limited.

Compounds of the Formula IX may be conveniently prepared from a suitably protected precursor which is commercially available, for example from Aldrich Chemical Company Inc.

Protected Intermediates

In a further aspect of the invention we provide N-protected derivatives of the formulae P—W—C(═X)-Q''' wherein P, W and X are as defined in relation to Formula I and Q''' is a monoprotected ring (as hereinbefore defined)

P—W—C(═X)-Q''' wherein P, W and X are as defined in relation to Formula I and Q''' is a diprotected ring (as hereinbefore defined)

Where Q''' has one nitrogen atom (eg. piperidine) then this is mono-protected. Where ring Q''' has two nitrogen atoms (eg. piperazine) then this is either mono- or di-protected. Convenient protecting groups include tertiary-butyloxycarbonyl (t-Boc), benzyloxycarbonyl (Cbz) and benzyl.

A compound of formula (I), or a pharmaceutically acceptable salt thereof, may be used in the treatment of:

1. Respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;

2. Bone and joints: arthritides associated with or including osteoarthritis/osteoarthrosis, both primary and secondary to, for example, congenital hip dysplasia; cervical and lumbar spondylitis, and low back and neck pain; rheumatoid arthritis and Still's disease; seronegative spondyloarthropathies including ankylosing spondylitis, psoriatic arthritis, reactive arthritis and undifferentiated spondarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muclde-Wells syndrome, and Familial Hibernian Fever, Kikuchi disease; drug-induced arthalgias, tendonititides, and myopathies;

3. Pain and connective tissue remodelling of musculoskeletal disorders due to injury [for example sports injury] or disease: arthitides (for example rheumatoid arthritis, osteoarthritis, gout or crystal arthropathy), other joint disease (such as intervertebral disc degeneration or temporomandibular joint degeneration), bone remodelling disease (such as osteoporosis, Paget's disease or osteonecrosis), polychondritis, scleroderma, mixed connective tissue disorder, spondyloarthropathies or periodontal disease (such as periodontitis);

4. Skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

5. Eyes: blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial;

6. Gastrointestinal tract: glossitis, gingivitis, periodontitis; oesophagitis, including reflux; eosinophilic gastro-enteritis, mastocytosis, Crohn's disease, colitis including ulcerative colitis, proctitis, pruritis ani; coeliac disease, irritable bowel syndrome, and food-related allergies which may have effects remote from the gut (for example migraine, rhinitis or eczema);

7. Abdominal: hepatitis, including autoimmune, alcoholic and viral; fibrosis and cirrhosis of the liver; cholecystitis; pancreatitis, both acute and chronic;

8. Genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

9. Allograft rejection: acute and chronic following, for example, transplantation of kidney, heart, liver, lung, bone marrow, skin or cornea or following blood transfusion; or chronic graft versus host disease;

10. CNS: Alzheimer's disease and other dementing disorders including CJD and nvCJD; amyloidosis; multiple sclerosis and other demyelinating syndromes; cerebral atherosclerosis and vasculitis; temporal arteritis; myasthenia gravis; acute and chronic pain (acute, intermittent or persistent, whether of central or peripheral origin) including visceral pain, headache, migraine, trigeminal neuralgia, atypical facial pain, joint and bone pain, pain arising from cancer and tumor invasion, neuropathic pain syndromes including diabetic, post-herpetic, and HIV-associated neuropathies; neurosarcoidosis; central and peripheral nervous system complications of malignant, infectious or autoimmune processes;

11. Other auto-immune and allergic disorders including Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome;

12. Other disorders with an inflammatory or immunological component; including HIV infection and acquired immune deficiency syndrome (AIDS), leprosy, Sezary syndrome, and paraneoplastic syndromes;

13. Cardiovascular: atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (for example syphilitic); vasculitides; disorders of the proximal and peripheral veins including phlebitis and thrombosis, including deep vein thrombosis and complications of varicose veins;

14. Oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and, 15. Gastrointestinal tract: Coeliac disease, proctitis, eosinopilic gastro-enteritis, mastocytosis, Crohn's disease, ulcerative colitis, microscopic colitis, indeterminant colitis, irritable bowel disorder, irritable bowel syndrome, non-inflammatory diarrhea, food-related allergies which have effects remote from the gut, e.g., migraine, rhinitis and eczema.

The invention further provides a compound of Formula (I) as defined above for use in the treatment of C—C-chemokine mediated disease such as inflammatory disease. When used in this way, the compounds are suitably formulated into pharmaceutical compositions which further contain a pharmaceutically acceptable carrier and these form a further aspect of the invention. The compound is conveniently used for the treatment of a CCR2b mediated inflammatory disease and/or a CCR5 mediated inflammatory disease.

Furthermore, the invention provides the use of a compound of Formula (I) as defined above in the preparation of a medicament for treating C—C chemokine mediated disease, and in particular for the treatment of CCR2B mediated inflammatory disease.

Furthermore, the invention provides the use of a compound of Formula (I) as defined above in the preparation of a medicament for treating a CCR5 mediated disease state.

The invention further relates to combination therapies wherein a compound of the invention, or a pharmaceutically acceptable salt thereof, or a pharmaceutical composition or formulation comprising a compound of the invention, is administered concurrently or sequentially or as a combined preparation with another therapeutic agent or agents, for the treatment of one or more of the conditions listed.

In particular, for the treatment of the inflammatory diseases such as (but not restricted to) rheumatoid arthritis, osteoarthritis, asthma, allergic rhinitis, chronic obstructive pulmonary disease (COPD), psoriasis, and inflammatory bowel disease, the compounds of the invention may be combined with agents listed below.

Non-steroidal anti-inflammatory agents (hereinafter NSAIDs) including non-selective cyclo-oxygenase COX-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate; leflunomide; hydroxychloroquine; d-penicillamine; auranofin or other parenteral or oral gold preparations; analgesics; diacerein; intra-articular therapies such as hyaluronic acid derivatives; and nutritional supplements such as glucosamine.

The present invention still further relates to the combination of a compound of the invention, or a pharmaceutically acceptable salt thereof, together with a cytokine or agonist or antagonist of cytokine function, (including agents which act on cytokine signalling pathways such as modulators of the SOCS system) including alpha-, beta-, and gamma-interferons; insulin-like growth factor type I (IGF-1); interleukins (IL) including IL1 to 17, and interleukin antagonists or inhibitors such as anakinra; tumour necrosis factor alpha (TNF-α) inhibitors such as anti-TNF monoclonal antibodies (for example infliximab; adalimumab, and CDP-870) and TNF receptor antagonists including immunoglobulin molecules (such as etanercept) and low-molecular-weight agents such as pentoxyfylline.

In addition the invention relates to a combination of a compound of the invention, or a pharmaceutically acceptable salt thereof, with a monoclonal antibody targeting B-Lymphocytes (such as CD20 (rituximab), MRA-aIL16R and T-Lymphocytes, CTLA4-Ig, HuMax I1-15).

The present invention still further relates to the combination of a compound of the invention, or a pharmaceutically acceptable salt thereof, with a modulator of chemokine receptor function such as an antagonist of CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and $CX_3CR1$ for the C—$X_3$—C family.

The present invention further relates to the combination of a compound of the invention, or a pharmaceutically acceptable salt thereof, with an inhibitor of matrix metalloprotease (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-9 and MMP-12, including agents such as doxycycline.

The present invention still further relates to the combination of a compound of the invention, or a pharmaceutically acceptable salt thereof, and a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; a N-(5-substituted)-thiophene-2-alkylsulfonamide; 2,6-di-tert-butylphenolhydrazones; a methoxytetrahydropyrans such as Zeneca ZD-2138; the compound SB-210661; a pyridinyl-substituted 2-cyanonaphthalene compound such as L-739,010; a 2-cyanoquinoline compound such as L-746,530; or an indole or quinoline compound such as MK-591, MK-886, and BAY x 1005.

The present invention further relates to the combination of a compound of the invention, or a pharmaceutically acceptable salt thereof, and a receptor antagonist for leukotrienes (LT) B4, LTC4, LTD4, and LTE4. selected from the group consisting of the phenothiazin-3-1s such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY x 7195.

The present invention still further relates to the combination of a compound of the invention, or a pharmaceutically acceptable salt thereof, and a phosphodiesterase (PDE) inhibitor such as a methylxanthanine including theophylline and aminophylline; a selective PDE isoenzyme inhibitor including a PDE4 inhibitor an inhibitor of the isoform PDE4D, or an inhibitor of PDE5.

The present invention further relates to the combination of a compound of the invention, or a pharmaceutically acceptable salt thereof, and a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine; applied orally, topically or parenterally.

The present invention still further relates to the combination of a compound of the invention, or a pharmaceutically acceptable salt thereof, and a proton pump inhibitor (such as omeprazole) or a gastroprotective histamine type 2 receptor antagonist.

The present invention further relates to the combination of a compound of the invention, or a pharmaceutically acceptable salt thereof, and an antagonist of the histamine type 4 receptor.

The present invention still further relates to the combination of a compound of the invention, or a pharmaceutically acceptable salt thereof, and an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethylnorepinephrine hydrochloride.

The present invention further relates to the combination of a compound of the invention, or a pharmaceutically acceptable salt thereof, and an anticholinergic agents including muscarinic receptor (M1, M2, and M3) antagonist such as atropine, hyoscine, glycopyrrrolate, ipratropium bromide, tiotropium bromide, oxitropium bromide, pirenzepine or telenzepine.

The present invention still further relates to the combination of a compound of the invention, or a pharmaceutically acceptable salt thereof, and a beta-adrenoceptor agonist (including beta receptor subtypes 1-4) such as isoprenaline, salbutamol, formoterol, salmeterol, terbutaline, orciprenaline, bitolterol mesylate, or pirbuterol, or a chiral enantiomer thereof.

The present invention further relates to the combination of a compound of the invention, or a pharmaceutically acceptable salt thereof, and a chromone, such as sodium cromoglycate or nedocromil sodium.

The present invention still further relates to the combination of a compound of the invention, or a pharmaceutically acceptable salt thereof, with a glucocorticoid, such as flunisolide, triamcinolone acetonide, beclomethasone dipropionate, budesonide, fluticasone propionate, ciclesonide or mometasone furoate.

The present invention further relates to the combination of a compound of the invention, or a pharmaceutically acceptable salt thereof, with an agent that modulates a nuclear hormone receptor such as PPARs, for example rosiglitazone.

The present invention still further relates to the combination of a compound of the invention, or a pharmaceutically acceptable salt thereof, together with an immunoglobulin (Ig) or Ig preparation or an antagonist or antibody modulating Ig function such as anti-IgE (for example omalizumab).

The present invention further relates to the combination of a compound of the invention, or a pharmaceutically acceptable salt thereof, and another systemic or topically-applied anti-inflammatory agent, such as thalidomide or a derivative thereof, a retinoid, dithranol or calcipotriol.

The present invention still further relates to the combination of a compound of the invention, or a pharmaceutically acceptable salt thereof, and combinations of aminosalicylates and sulfapyridine such as sulfasalazine, mesalazine, balsalazide, and olsalazine; and immunomodulatory agents such as the thiopurines, and corticosteroids such as budesonide.

The present invention further relates to the combination of a compound of the invention, or a pharmaceutically acceptable salt thereof, together with an antibacterial agent such as a penicillin derivative, a tetracycline, a macrolide, a beta-lactam, a fluoroquinolone, metronidazole, an inhaled aminoglycoside; an antiviral agent including acyclovir, famciclovir, valaciclovir, ganciclovir, cidofovir, amantadine, rimantadine, ribavirin, zanamavir and oseltamavir; a protease inhibitor such as indinavir, nelfinavir, ritonavir, and saquinavir; a nucleoside reverse transcriptase inhibitor such as didanosine, lamivudine, stavudine, zalcitabine or zidovudine; or a non-nucleoside reverse transcriptase inhibitor such as nevirapine or efavirenz.

The present invention still further relates to the combination of a compound of the invention, or a pharmaceutically acceptable salt thereof, and a cardiovascular agent such as a calcium channel blocker, a beta-adrenoceptor blocker, an angiotensin-converting enzyme (ACE) inhibitor, an angiotensin-2 receptor antagonist; a lipid lowering agent such as a statin or a fibrate; a modulator of blood cell morphology such as pentoxyfylline; thrombolytic, or an anticoagulant such as a platelet aggregation inhibitor.

The present invention further relates to the combination of a compound of the invention, or a pharmaceutically acceptable salt thereof, and a CNS agent such as an antidepressant (such as sertraline), an anti-Parkinsonian drug (such as deprenyl, L-dopa, ropinirole, pramipexole, a MAOB inhibitor such as selegine and rasagiline, a comP inhibitor such as tasmar, an A-2 inhibitor, a dopamine reuptake inhibitor, an NMDA antagonist, a nicotine agonist, a dopamine agonist or an inhibitor of neuronal nitric oxide synthase), or an anti-Alzheimer's drug such as donepezil, rivastigmine, tacrine, a COX-2 inhibitor, propentofylline or metrifonate.

The present invention still further relates to the combination of a compound of the invention, or a pharmaceutically acceptable salt thereof, and an agent for the treatment of acute or chronic pain, such as a centrally or peripherally-acting analgesic (for example an opioid or derivative thereof), carbamazepine, gabapentin, pregabalin, phenyloin, sodium valproate, amitryptiline or other anti-depressant agent-s, paracetamol, or a non-steroidal anti-inflammatory agent.

The present invention further relates to the combination of a compound of the invention, or a pharmaceutically acceptable salt thereof, together with a parenterally or topically-applied (including inhaled) local anaesthetic agent such as lignocaine or a derivative thereof.

A compound of the present invention, or a pharmaceutically acceptable salt thereof, can also be used in combination with an anti-osteoporosis agent including a hormonal agent such as raloxifene, or a biphosphonate such as alendronate.

The present invention still further relates to the combination of a compound of the invention, or a pharmaceutically acceptable salt thereof, together with a: (i) tryptase inhibitor; (ii) platelet activating factor (PAF) antagonist; (iii) interleukin converting enzyme (ICE) inhibitor; (iv) IMPDH inhibitor; (v) adhesion molecule inhibitors including VLA-4 antagonist; (vi) cathepsin; (vii) kinase inhibitor such as an inhibitor of tyrosine kinase (such as Btk, Itk, Jak3 or MAP, for example Gefitinib or Imatinib mesylate), a serine/threonine kinase (such as an inhibitor of a MAP kinase such as p38, JNK, protein kinase A, B or C, or IKK), or a kinase involved in cell cycle regulation (such as a cylin dependent kinase); (viii) glucose-6 phosphate dehydrogenase inhibitor; (ix) kinin-B.sub1.- or B.sub2.-receptor antagonist; (x) anti-gout agent, for example colchicine; (xi) xanthine oxidase inhibitor, for example allopurinol; (xii) uricosuric agent, for example probenecid, sulfinpyrazone or benzbromarone; (xiii) growth hormone secretagogue; (xiv) transforming growth factor (TGFβ); (xv) platelet-derived growth factor (PDGF); (xvi) fibroblast growth factor for example basic fibroblast growth factor (bFGF); (xvii) granulocyte macrophage colony stimulating factor (GM-CSF); (xviii) capsaicin cream; (xix) tachykinin NK.sub1. or NK.sub3. receptor antagonist such as NKP-608C, SB-233412 (talnetant) or D-4418; (xx) elastase inhibitor such as UT-77 or ZD-0892; (xxi) TNF-alpha converting enzyme inhibitor (TACE); (xxii) induced nitric oxide synthase (iNOS) inhibitor; (xxiii) chemoattractant receptor-homologous molecule expressed on TH2 cells, (such as a CRTH2 antagonist); (xxiv) inhibitor of P38; (xxv) agent modulating the function of Toll-like receptors (TLR), (xxvi) agent modulating the activity of purinergic receptors such as P2×7; or (xxvii) inhibitor of transcription factor activation such as NFkB, API, or STATS.

A compound of the invention, or a pharmaceutically acceptable salt thereof, can also be used in combination with an existing therapeutic agent for the treatment of cancer, for example suitable agents include:

(i) an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); an antimetabolite (for example an antifolate such as a fluoropyrimidine like 5-fluorouracil or tegafur, raltitrexed, methotrexate, cytosine arabinoside, hydroxyurea, gemcitabine or paclitaxel); an antitumour antibiotic (for example an anthracycline such as adriamycin, bleomycin, doxorubicin, daunomycin, epirubicin, idarubicin, mitomycin-C, dactinomycin or mithramycin); an antimitotic agent (for example a vinca alkaloid such as vincristine, vinblastine, vindesine or vinorelbine, or a taxoid such as taxol or taxotere); or a topoisomerase inhibitor (for example an epipodophyllotoxin such as etoposide, teniposide, amsacrine, topotecan or a camptothecin);

(ii) a cytostatic agent such as an antioestrogen (for example tamoxifen, toremifene, raloxifene, droloxifene or iodoxyfene), an oestrogen receptor down regulator (for example fulvestrant), an antiandrogen (for example bicalutamide, flutamide, nilutamide or cyproterone acetate), a LHRH antagonist or LHRH agonist (for example goserelin, leuprorelin or buserelin), a progestogen (for example megestrol acetate), an aromatase inhibitor (for example as anastrozole, letrozole, vorazole or exemestane) or an inhibitor of 5α-reductase such as finasteride;

(iii) an agent which inhibits cancer cell invasion (for example a metalloproteinase inhibitor like marimastat or an inhibitor of urokinase plasminogen activator receptor function);

(iv) an inhibitor of growth factor function, for example: a growth factor antibody (for example the anti-erbb2 antibody trastuzumab, or the anti-erbb1 antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro- 4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) or 6-acrylamido-N-(3-chloro-4-fluorophenyl)-7-(3-morpholinopropoxy)quinazolin-4-amine (CI 1033)), an inhibitor of the platelet-derived growth factor family, or an inhibitor of the hepatocyte growth factor family;

(v) an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin αvβ3 function or an angiostatin);

(vi) a vascular damaging agent such as combretastatin A4, or a compound disclosed in WO 99/02166, WO 00/40529, WO 00/41669, WO 01/92224, WO 02/04434 or WO 02/08213;

(vii) an agent used in antisense therapy, for example one directed to one of the targets listed above, such as ISIS 2503, an anti-ras antisense;

(viii) an agent used in a gene therapy approach, for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; or (ix) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Some compounds of formula (I) may possess chiral centres. It is to be understood that the invention encompasses the use of all such optical isomers and diasteroisomers as well as compounds of formula (I) in any of these forms, and pharmaceutical compositions containing compounds of formula (I).

The invention further relates to all tautomeric forms of the compounds of formula (IA) and pharmaceutical compositions containing these.

It is also to be understood that certain compounds of the formula I can exist in solvated as well as unsolvated forms such as, for example, hydrated forms. It is to be understood that the invention encompasses all such solvated forms and pharmaceutical compositions containing these.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intermuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, and esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedure well known in the art.

Compositions for administration by insufflation may be in the form of a finely divided powder containing particles of average diameter of, for example, 30μ or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the Formula I will naturally vary according to the nature and severity of the conditions, the age and sex of the animal or patient and the route of administration, according to well known principles of medicine.

In using a compound of the Formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred.

In a further aspect, the invention provides a method of treating inflammatory disease by administering a compound of Formula I as described above, or a pharmaceutical composition as described above.

The Invention is Further Illustrated, but not Limited by the Following Biological Assay and Examples in which the Following General Procedures were Used Unless Stated Otherwise:

Anhydrous N,N-Dimethylformamide (DMF) and tetrahydrofuran (THF) were obtained from Aldrich SURESEAL™ bottles. Other commercially available reagents and solvents were used without further purification unless otherwise stated. Organic solvent extracts were dried over anhydrous $MgSO_4$. $^1H$, $^{13}C$ and $^{19}F$ NMR were recorded on Bruker WM200, WM250, WM300 or WM400 instruments using $Me_2SO$-$d_6$ with $Me_4Si$ or $CCl_3F$ as internal standard as appropriate, unless otherwise stated. Chemical shifts are in d (ppm) and peak multiplicities are designated as follows: s, singlet; d, doublet; dd, doublet of doublets; t, triplet; dt, doublet of triplets; q, quartet; m, multiplet; br, broad. Mass spectra were recorded on VG 12-12 quadrupole, VG 70-250 SE, VG ZAB 2-SE or a VG modified AEI/Kratos MS9 spectrometers. For TLC analysis, Merck precoated TLC plates (silica gel 60 F254, d=0.25 mm) were used. Flash chromatography was performed on silica (Merck Kieselgel: Art.9385). Melting point determinations were performed on a Kofler block or with a Büchi melting point apparatus and are uncorrected. All temperatures are in degrees Centigrade. EDCI is 1-(3-dimethylaminopropyl)-3-ethylcarbodiimide hydrochloride. HOBT is 1-hydroxybenzotriazole.

Biological Assays for hMCP-1 Antagonists
a) hMCP-1 Receptor-Binding Assay
i) Cloning and Expression of hMCP-1 Receptor The MCP-1 receptor B (CCR2B) cDNA was cloned by PCR from THP-1 cell RNA using suitable oligonucleotide primers based on the published MCP-1 receptor sequences (Charo et al., 1994, *Proc. Natl. Acad. Sci. USA*, 91, 2752). The resulting PCR products were cloned into vector PCR-II™ (InVitrogen, San Diego, Calif.). Error free CCR2B cDNA was subcloned as a Hind III-Not I fragment into the eukaryotic expression vector pCDNA3 (InVitrogen) to generate pCDNA3/CC-CKR2A and pCDNA3/CCR2B respectively.

Linearised pCDNA3/CCR2B DNA was transfected into CHO-K1 cells by calcium phosphate precipitation (Wigler et al., 1979, *Cell*, 16, 777). Transfected cells were selected by the addition of Geneticin Sulphate (G418, Gibco BRL) at 1 mg/ml, 24 hours after the cells had been transfected. Preparation of RNA and Northern blotting were carried out as described previously (Needham et al., 1995, *Prot. Express. Purific.*, 6, 134). CHO-K1 clone 7 (CHO—CCR2B) was identified as the highest MCP-1 receptor B expressor.

ii) Preparation of Membrane Fragments

CHO-CCR2B cells were grown in DMEM supplemented with 10% foetal calf serum, 2 mM glutamine, 1× Non-Essential Amino Acids, 1× Hypoxanthine and Thymidine Supplement and Penicillin-Streptomycin (at 50 μg streptomycin/ml, Gibco BRL). Membrane fragments were prepared using cell lysis/differential centrifugation methods as described previously (Siciliano et al., 1990, *J. Biol. Chem.*, 265, 19658). Protein concentration was estimated by BCA protein assay (Pierce, Rockford, Ill.) according to the manufacturer's instructions.

iii) Assay $^{125}$I-labeled MCP-1 was prepared using Bolton and Hunter conjugation (Bolton et al., 1973, *Biochem. J.*, 133, 529; Amersham International plc].

Test compounds were dissolved in DMSO and further diluted in assay buffer (50 mM HEPES, 1 mM $CaCl_2$, 5 nM $MgCl_2$, 0.03% BSA, pH 7.2) to give a range of concentrations starting with a top final concentration of 10 uM. All incubations had a 100 ul final volume and a DMSO concentration of 1%. Incubations contained 200 pM $^{125}$I-labeled MCP-1 (Amersham Pharmacia), 2.5 mg/ml Scintillation proximity assay beads (Amersham Pharmacia RPNQ) and approx 5 ug CHO-CCR2B cell membranes. Non-specific binding was determined by the inclusion of a 1 uM unlabelled MCP-1 in the place of test compound. Total binding was determined in the presence of 1% DMSO without compound. Incubations were performed in sealed optiplates and kept at room temperature for 16 hours after which the plates were counted on a Packard TopCount (Packard TopCount™). Dose-response curves were generated from duplicate date points and $IC_{50}$ values were calculated using GraphPad Prizm® software. Percent inhibitions were calculated for single concentrations of compound by using the following formula 100−((compound binding minus non-specific binding)/(total binding minus non-specific binding)×100).

In the above assay each compound set out in the Examples below showed an $IC_{50}$ value of better than 20 μmol.

b) Biological Assay for the Ability of Compounds to Inhibit the Binding of MIP-1α

This ability is assessed using an in vitro radioligand binding assay. Membranes are prepared from Chinese hamster ovary cells which express the recombinant human CCR5 receptor. These membranes are incubated with 0.1 nM iodinated MIP-1α, scintillation proximity beads and various concentrations of the compounds of the invention in 96-well plates. The amount of iodinated MIP-1α bound to the receptor is then determined by scintillation counting. Competition curves are obtained for compounds and the concentration of compound which displaces 50% of bound iodinated MIP-1α is calculated ($IC_{50}$).

In the above assay some of the compounds set out in the Examples showed an $IC_{50}$ value of better than 10 μmol.

| Example Number | Structure | Characterisation Data | Route |
|---|---|---|---|
| 1 | 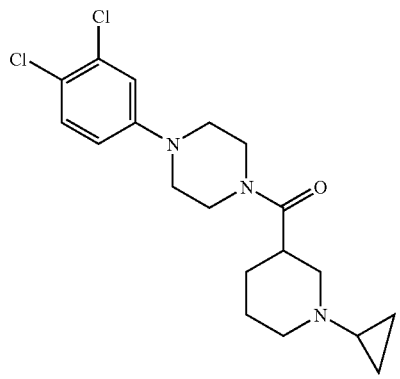 | 1-[(1-cyclopropylpiperidin-3-yl)carbonyl]-4-(3,4-dichlorophenyl)piperazine<br>LCMS M/z(+) 383.07 (M + H$^+$)<br>$^1$H-NMR (CDCl$_3$): 0.33-0.52 (m, 4H), 1.53 (t, 2H), 1.71-1.84 (m, 2H), 2.18 (t, 1H), 2.40 (t, 1H), 2.69-2.78 (m, 1H), 3.00-3.29 (m, 4H), 3.60-3.80 (m, 4H), 6.72 (dd, 1H), 6.95 (d, 1H) and 7.29 (d, 1H) | A1 |
| 2 | 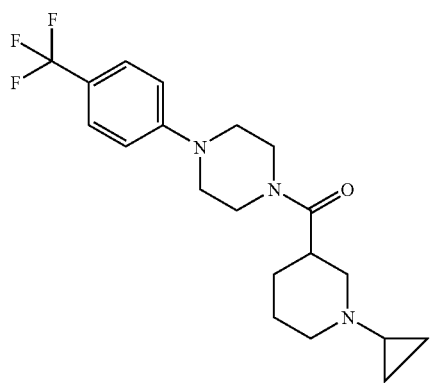 | 1-[(1-cyclopropylpiperidin-3-yl)carbonyl]-4-[4-(trifluoromethyl)phenyl]piperazine<br>LCMS M/z(+) 382.39 (M + H$^+$) | A1 |

-continued

| Example Number | Structure | Characterisation Data | Route |
|---|---|---|---|
| 3 | 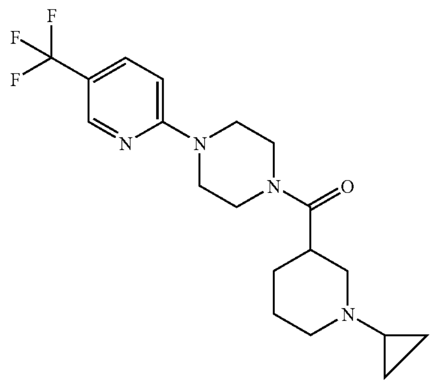 | 1-[(1-cyclopropylpiperidin-3-yl)carbonyl]-4-[5-(trifluoromethyl)pyridin-2-yl]piperazine<br>LCMS M/z(+) 383.37 (M + H⁺) | A1 |
| 4 | 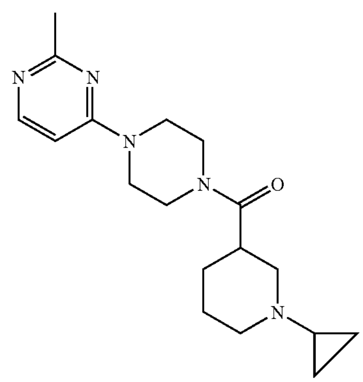 | 4-{4-[(1-cyclopropylpiperidin-3-yl)carbonyl]piperazin-1-yl}-2-methyl pyrimidine<br>LCMS M/z(+) 330.33 (M + H⁺) | A1 |
| 5 | 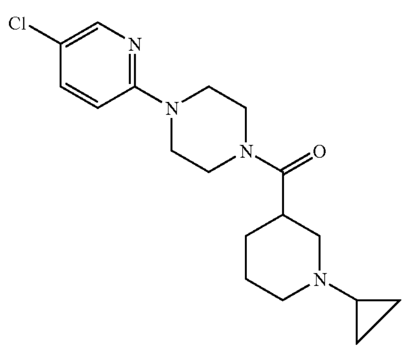 | 1-(5-chloropyridin-2-yl)-4-[(1-cyclopropylpiperidin-3-yl)carbonyl]piperazine<br>LCMS M/z(+) 349.3 (M + H⁺)<br>¹H-NMR (CDCl₃): | A1 |
| 6 | 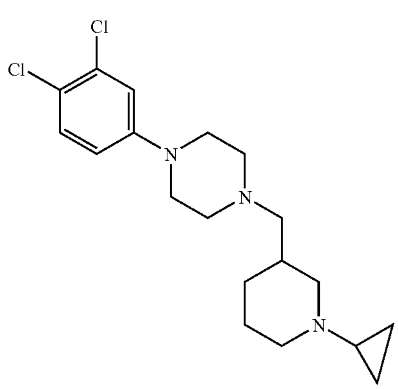 | 1-[(1-cyclopropylpiperidin-3-yl)methyl]-4-(3,4-dichlorophenyl)piperazine<br>LCMS M/z(+) 370.38 (M + H⁺)<br>¹H-NMR (CDCl₃): 0.41 (m, 4H), 0.91 (m, 1H), 1.46-1.82 (m, 6H), 2.11 (m, 1H), 2.19 (m, 2H), 2.54 (m, 4H), 2.96 (d, 1H), 3.09 (d, 1H), 3.15 (t, 4H), 6.71 (dd, 1H), 6.94 (d, 1H), and 7.24 (s, 1H) | B |

| Example Number | Structure | Characterisation Data | Route |
|---|---|---|---|
| 7 | 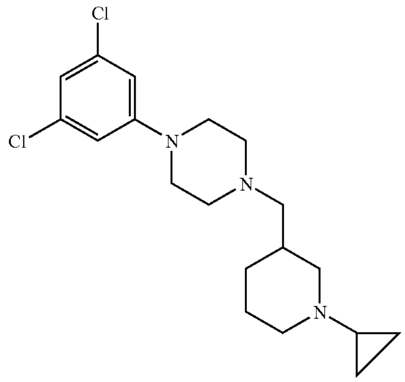 | 1-[(1-cyclopropylpiperidin-3-yl)methyl]-4-(3,5-dichlorophenyl)piperazine<br>LCMS M/z(+) 370.38 (M + H$^+$)<br>$^1$H-NMR (CDCl$_3$): 0.30-0.40 (m, 4H), 0.84 (m, 1H), 1.38-1.75 (m, 6H), 2.05 (m, 1H), 2.14 (m, 2H), 2.37-2.50 (m, 4H), 2.89 (d, 1H), 3.04 (d, 1H), 3.13 (t, 4H), 6.65 (m, 2H) and 6.69 (s, 1H) | B |
| 8 | 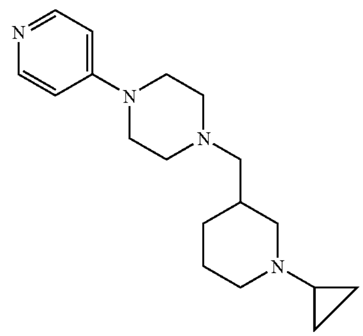 | 1-[(1-cyclopropylpiperidin-3-yl)methyl]-4-pyridin-4-ylpiperazine<br>LCMS M/z(+) 301.49 (M + H$^+$) $^1$H-NMR (CDCl$_3$): | B |
| 9 | 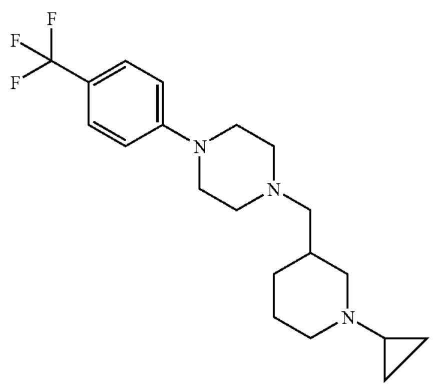 | 1-[(1-cyclopropylpiperidin-3-yl)methyl]-4-[4-(trifluoromethyl)phenyl]piperazine<br>LCMS M/z(+) (M + H$^+$)<br>$^1$H-NMR (CDCl$_3$): 0.30-0.40 (m, 4H), 0.83 (m, 1H), 1.38-1.80 (m, 6H), 2.05 (m, 1H), 2.15 (m, 2H), 2.40-2.53 (m, 4H), 2.90 (d, 1H), 3.03 (d, 1H), 3.19 (t, 4H), 6.86 (d, 2H), and 7.40 (d, 2H) | B |
| 10 | 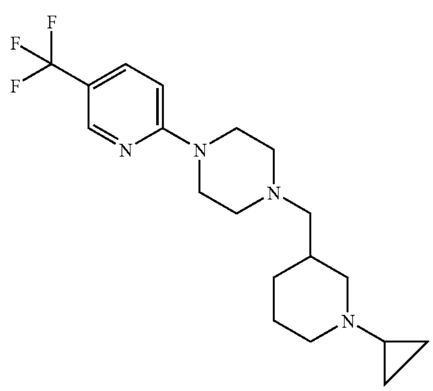 | 1-[(1-cyclopropylpiperidin-3-yl)methyl]-4-[5-(trifluoromethyl)pyridin-2-yl]piperazine<br>LCMS M/z(+) 369.64 (M + H$^+$)<br>$^1$H-NMR (CDCl$_3$): 0.28-0.41 (m, 4H), 0.84 (m, 1H), 1.38-1.80 (m, 6H), 2.05 (m, 1H), 2.13 (m, 2H), 2.35-2.49 (m, 4H), 2.91 (d, 1H), 3.06 (d, 1H), 3.57 (t, 4H), 6.55 (d, 1H), 7.52 (dd, 1H) and 8.30 (s, 1H) | B |

| Example Number | Structure | Characterisation Data | Route |
|---|---|---|---|
| 11 | 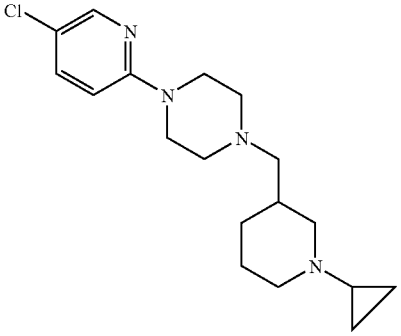 | 1-(5-chloropyridin-2-yl)-4-[(1-cyclopropylpiperidin-3-yl)methyl]piperazine<br>LCMS M/z(+) 335.46 (M + H$^+$)<br>$^1$H-NMR (CDCl$_3$): 0.28-0.41 (m, 4H), 0.85 (m, 1H), 1.39-1.80 (m, 6H), 2.06 (m, 1H), 2.13 (m, 2H), 2.34-2.48 (m, 4H), 2.91 (d, 1H), 3.05 (d, 1H), 3.43 (t, 4H), 6.49 (d, 1H), 7.33 (dd, 1H) and 8.04 (d, 1H) | B |
| 12 | 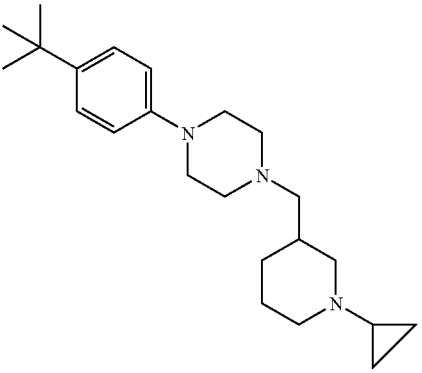 | 1-(4-tert-butylphenyl)-4-[(1-cyclopropylpiperidin-3-yl)methyl]piperazine<br>LCMS M/z(+) 356.67 (M + H$^+$)<br>$^1$H-NMR (CDCl$_3$): 0.30-0.40 (m, 4H), 0.83 (m, 1H), 1.24 (s, 9H), 1.36-1.80 (m, 6H), 2.05 (m, 1H), 2.13 (m, 2H), 2.39-2.53 (m, 4H), 2.91 (d, 1H), 3.02 (d, 1H), 3.10 (t, 4H), 6.70 (d, 2H), and 7.30 (d, 2H) | B |
| 13 | 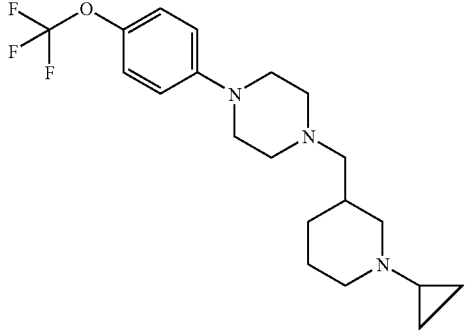 | 1-[(1-cyclopropylpiperidin-3-yl)methyl]-4-[4-(trifluoromethoxy)phenyl]piperazine<br>LCMS M/z(+) 384.82 (M + H$^+$)<br>$^1$H-NMR (CDCl$_3$): 0.28-0.41 (m, 4H), 0.85 (m, 1H), 1.37-1.79 (m, 6H), 2.05 (m, 1H), 2.13 (m, 2H), 2.3-2.54 (m, 4H), 2.91 (d, 1H), 3.04 (d, 1H), 3.09 (t, 4H), 6.70 (d, 2H), and 7.10 (d, 2H) | B |
| 14 | 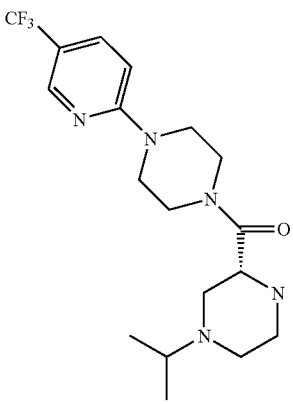 | (3R)-1-isopropyl-3-({4-[5-(trifluoromethyl)pyridin-2-yl]piperazin-1-yl}carbonyl)piperazine<br>LCMS M/z(+) 386 (M + H$^+$).<br>$^1$H NMR (400.132 MHz, CDCl$_3$) 1.00 (m, 6H), 2.08 (m, 2H,), 2.66 (m, 3H), 2.77 (d, 1H), 2.95 (d, 1H), 3.70 (m, 11H), 6.98 (d, 1H), 7.82 (dd, 1H,), 8.42 (d, 1H) | C1 |

| Example Number | Structure | Characterisation Data | Route |
|---|---|---|---|
| 15 | 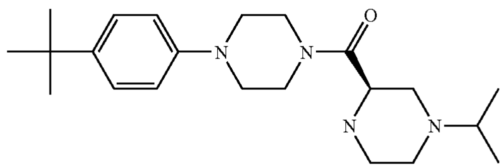 | (3R)-3-{[4-(4-tert-Butylphenyl) piperazin-1-yl]carbonyl}-1-isopropyl piperazine<br>LCMS M/z(+) 373 (M + H$^+$).<br>$^1$H NMR (400.132 MHz, DMSO) 1.00 (t, 6H), 1.25 (s, 9H), 2.14-2.36 (m, 2H), 2.61-3.22 (m, 9H), 3.38-3.87 (m, 4H), 4.03 (d, 1H), 6.90 (d, 2H), 7.26 (d, 2H) | C1 |
| 16 | 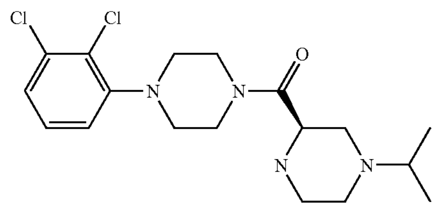 | (3R)-3-{[4-(2,3-Dichlorophenyl) piperazin-1-yl]carbonyl}-1-isopropyl piperazine<br>LCMS M/z(+) 385 (M + H$^+$).<br>$^1$H NMR (400.132 MHz, DMSO) 0.94-1.04 (m, 6H), 2.07-2.30 (m, 2H), 2.63-3.15 (m, 9H), 3.42-3.84 (m, 4H), 3.94 (d, 1H), 7.07-7.22 (m, 1H), 7.27-7.44 (m, 2H) | C1 |
| 17 | 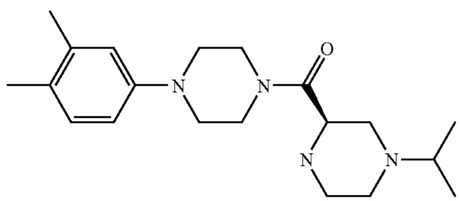 | (3R)-3-{[4-(3,4-Dimethylphenyl) piperazin-1-yl]carbonyl}-1-isopropyl piperazine<br>LCMS M/z(+) 345 (M + H$^+$).<br>$^1$H NMR (400.132 MHz, DMSO) 0.99 (t, 6H), 2.05-2.25 (m, 8H), 2.13 (s, 3H), 2.18 (s, 2H), 2.62-2.88 (m, 4H), 2.92-3.21 (m, 5H), 3.45-3.78 (m, 4H), 3.88 (d, 1H), 6.68 (dd, 1H), 6.78 (s, 1H), 6.99 (d, 1H) | C1 |
| 18 | 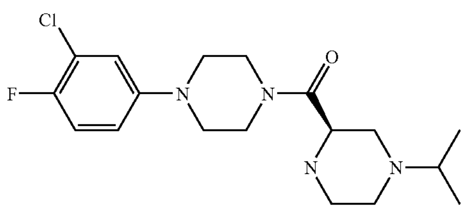 | (3R)-3-{[4-(3-Chloro-4-fluorophenyl)piperazin-1-yl]carbonyl}-1-isopropyl piperazine<br>LCMS M/z(+) 369 (M + H$^+$).<br>$^1$H NMR (400.132 MHz, DMSO) 0.91-1.03 (m, 6H), 2.09-2.28 (m, 2H), 2.64-2.90 (m, 4H), 2.92-3.39 (m, 5H), 3.43-3.77 (m, 4H), 3.92 (d, 1H), 6.89-7.00 (m, 1H), 7.06-7.15 (m, 1H), 7.27 (t, 1H) | C1 |
| 19 | 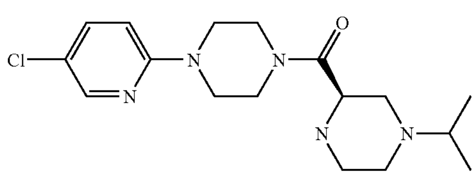 | (3R)-3-{[4-(5-Chloropyridin-2-yl) piperazin-1-yl]carbonyl}-1-isopropyl piperazine<br>LCMS M/z(+) 352 (M + H$^+$).<br>$^1$H NMR (400.132 MHz, CDCl$_3$) 1.33-1.37 (m, 6H), 2.69-2.95 (m, 2H), 3.20-3.87 (m, 13H), 4.47-4.51 (m, 1H), 6.60 (d, 1H), 7.46 (d, 1H), 8.12 (s, 1H) | C1 |
| 20 | 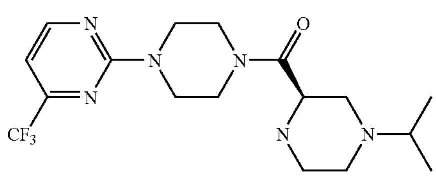 | 2-(4-{[(2R)-4-Isopropylpiperazin-2-yl]carbonyl}piperazin-1-yl)-4-(trifluoromethyl)pyrimidine<br>LCMS M/z(+) 387 (M + H$^+$).<br>$^1$H NMR (400.132 MHz, CDCl$_3$) 1.34 (t, 6H), 2.68-2.82 (m, 1H), 2.82-2.96 (m, 1H), 3.23-3.49 (m, 5H), 3.50-3.70 (m, 2H), 3.71-3.90 (m, 4H), 3.92-4.13 (m, 2H), 4.49 (dd, 1H), 6.83 (s, 1H), 8.53 (s, 1H) | C1 |
| 21 | 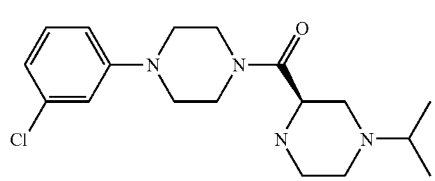 | (3R)-3-{[4-(3-Chlorophenyl)piperazin-1-yl]carbonyl}-1-isopropylpiperazine<br>LCMS M/z(+) 351, 353 (M + H$^+$).<br>$^1$H NMR (400.132 MHz, CDCl$_3$) 1.28-1.39 (m, 6H), 2.72-2.96 (m, 2H), 3.07-3.53 (m, 9H), 3.61-3.91 (m, 4H), 4.48 (d, 1H), 6.78 (d, 1H), 6.84-6.91 (m, 2H), 7.18 (t, 1H) | C1 |

| Example Number | Structure | Characterisation Data | Route |
|---|---|---|---|
| 22 | 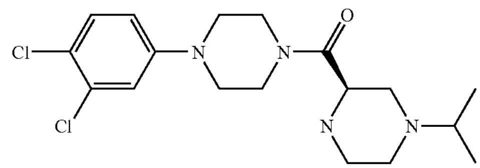 | (3R)-3-{[4-(3,4-Dichlorophenyl) piperazin-1-yl]carbonyl}-1-isopropyl piperazine<br>LCMS M/z(+) 385, 387 (M + H+).<br>$^1$H NMR (400.132 MHz, CDCl$_3$) 0.97-1.16 (m, 6H), 2.10-2.37 (m, 2H), 2.69-3.23 (m, 9H), 3.54-4.04 (m, 5H), 6.74 (dd, 1H), 6.96 (d, 1H), 7.29 (d, 1H) | C1 |
| 23 | 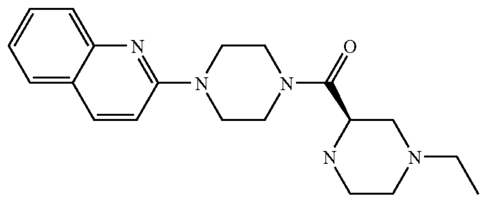 | 2-(4-{[(2R)-4-ethylpiperazin-2-yl] carbonyl}piperazin-1-yl)quinoline<br>LCMS M/z(+) 354 (M + H+).<br>$^1$H NMR (400.132 MHz, DMSO) 1.05-1.16 (m, 3H), 2.25-2.89 (m, 2H), 2.96-3.21 (m, 2H), 3.20-3.43 (m, 2H), 3.42-4.13 (m, 10H), 4.50-4.71 (m, 1H), 7.20-7.43 (m, 2H), 7.53-7.68 (m, 2H), 7.76 (d, 1H), 8.15 (d, 1H), 9.86 (br. s, 1H) | C1 |
| 24 | 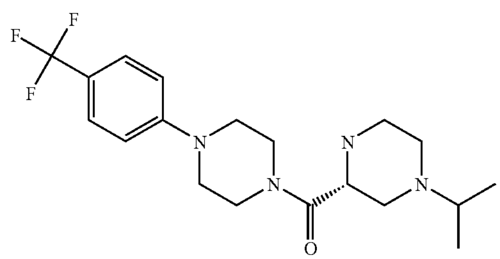 | (3R)-1-isopropyl-3-({4-[4-(trifluoromethyl)phenyl]piperazin-1-yl}carbonyl)piperazine<br>LCMS M/z(+) 386 (M + H+).<br>$^1$H NMR (400.132 MHz, DMSO) 0.92-0.99 (m, 6H), 1.97-2.11 (m, 2H), 2.55-2.78 (m, 4H), 2.90 (d, 1H), 3.14-3.43 (m, 4H), 3.45-3.81 (m, 5H), 7.08 (d, J = 8.8 Hz, 2H), 7.53 (d, 2H) | C1 |
| 25 | 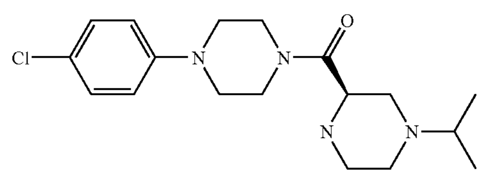 | (3R)-3-{[4-(4-chlorophenyl)piperazin-1-yl]carbonyl}-1-isopropylpiperazine<br>LCMS M/z(+) 351 (M + H+).<br>$^1$H NMR (400.132 MHz, DMSO) 0.90-0.99 (m, 6H), 1.96-2.09 (m, 2H), 2.55-2.77 (m, 4H), 2.84-2.96 (m, 1H), 2.99-3.25 (m, 4H), 3.45-3.79 (m, 5H), 6.97 (d, 2H), 7.26 (d, 2H) | C1 |
| 26 | 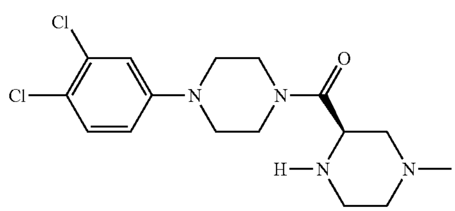 | (3R)-3-{[4-(3,4-dichlorophenyl) piperazin-1-yl]carbonyl}-1-methyl piperazine<br>LCMS M/z(+) 357.31 (M + H+).<br>$^1$H NMR (DMSO-d$_6$)(373 K): 1.84 (2H, m), 2.08 (3H, s), 2.59 (1H, dquintet), 2.69-2.77 (2H, m), 2.91 (2H, m, partially obscured), 3.23 (4H, t), 3.65 (4H, t), 3.69 (1H, dd), 6.91 (1H, dd), 7.09 (1H, d), 7.37 (1H, d) | C1 |
| 27 | 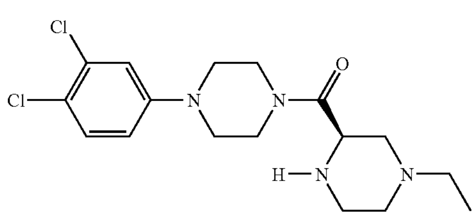 | (3R)-3-{[4-(3,4-dichlorophenyl) piperazin-1-yl]carbonyl}-1-ethyl piperazine<br>LCMS M/z(+) 371.34 (M + H+)<br>$^1$H NMR (400.132 MHz, DMSO): 0.99 (3H, m), 1.80 (2H, m), 2.31 (3H, m), 2.68 (2H, m), 2.80 (2H, m), 2.90 (2H, m), 3.63 (6H, m), 6.95 (1H, m), 7.14 (1H, m), 7.41 (1H, m) | C1 |

| Example Number | Structure | Characterisation Data | Route |
|---|---|---|---|
| 28 | 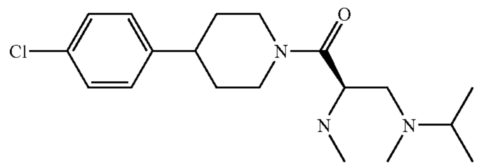 | (3R)-3-{[4-(4-chlorophenyl)piperidin-1-yl]carbonyl}-1-isopropylpiperazine<br>LCMS M/z(+) 350, 352 (M + H$^+$).<br>$^1$H NMR (400.132 MHz, CDCl$_3$) 1.08 (m, 6H), 1.46-1.75 (m, 2H), 1.77-2.03 (m, 2H), 2.06-2.38 (m, 2H), 2.51-3.27 (m, 8H), 3.85-3.99 (m, 1H), 4.07-4.21 (m, 1H), 4.69-4.85 (m, 1H), 7.05-7.18 (m, 2H), 7.24-7.35 (m, 2H) | C1 |
| 29 | 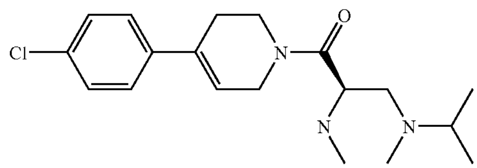 | (3R)-3-{[4-(4-chlorophenyl)-3,6-dihydropyridin-1(2H)-yl]carbonyl}-1-isopropylpiperazine<br>LCMS M/z(+) 348, 350 (M + H$^+$).<br>$^1$H NMR (400.132 MHz, CDCl3) 0.99-1.18 (m, 6H), 2.11-2.37 (m, 2H), 2.45-2.66 (m, 2H), 2.71-3.23 (m, 6H), 3.64-4.44 (m, 6H), 6.04 (d, 1H), 7.15-7.42 (m, 4H) | C1 |
| 30 | 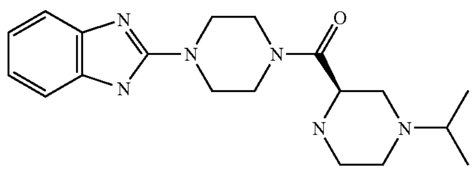 | 2-(4-{[(2R)-4-Isopropylpiperazin-2-yl]carbonyl}piperazin-1-yl)-1H-benzimidazole<br>LCMS M/z(+) 357 (M + H$^+$).<br>$^1$H NMR (400.132 MHz, DMSO) 0.99 (m, 6H), 2.08 (m, 2H), 2.60-2.81 (m, 3H), 2.95 (d, 1H), 3.40-3.79 (m, 10 H), 6.95 (m, 2H), 7.21 (m, 2H) | C1 |
| 31 | 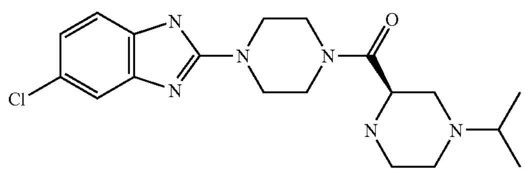 | 6-Chloro-2-(4-{[(2R)-4-isopropyl piperazin-2-yl]carbonyl}piperazin-1-yl)-1H-benzimidazole<br>LCMS M/z(+) 391, 393 (M + H$^+$).<br>$^1$H NMR (400.132 MHz, DMSO) 1.00-1.21 (m, 6H), 2.81-2.95 (m, 1H), 3.07 (t, 1H), 3.20-3.85 (m, 13H), 4.68 (m, 1H), 7.18 (d, 1H), 7.32 (d, 1H), 7.39 (s, 1H) | C1 |
| 32 | 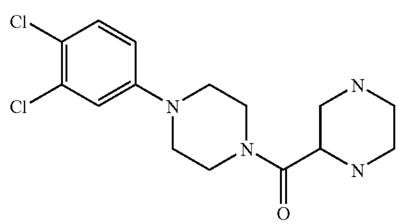 | (2R,S)-1-(3,4-dichlorophenyl)-4-(piperazin-2-ylcarbonyl)piperazine<br>LCMS M/z(+) 342.87 (M + H$^+$).<br>$^1$H NMR (400.132 MHz, DMSO) 2.39-2.49 (m, 2H), 2.54-2.71 (m, 3H), 2.76-2.88 (m, 2H), 3.49-3.76 (m, 5H), 3.10-3.38 (m, 5H), 6.96 (dd, 1H), 7.16 (d, 1H), 7.41 (d, 1H) | C1 |
| 33 | 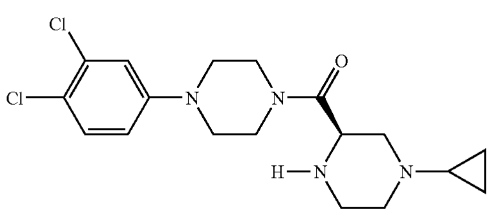 | (3R)-1-cyclopropyl-3-{[4-(3,4-dichloro phenyl)piperazin-1-yl]carbonyl}piperazine<br>LCMS M/z(+) 383.4(M + H$^+$)<br>$^1$H NMR (399.902 MHz, DMSO): 0.33 (2H, m), 0.41 (2H, m), 1.66 (1H, m), 2.17 (2H, m), 2.66 (1H, m), 2.76 (1H, m), 2.93 (3H, m), 3.22 (4H, m), 3.63 (5H, m), 6.90 (1H, m), 7.08 (1H, m), 7.37 (1H, m) | A1 |
| 34 | 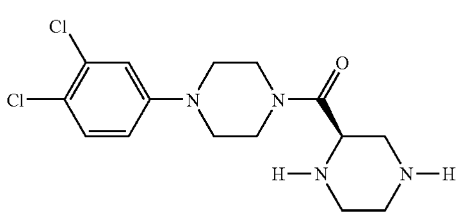 | (2R)-1-(3,4-dichlorophenyl)-4-[piperazin-2-ylcarbonyl]piperazine<br>LCMS M/z(+) 343.26(M + H$^+$)<br>$^1$H NMR (400.132 MHz, DMSO): 2.67 (2H, m), 2.85 (2H, m), 3.17 (4H, m), 3.70 (5H, m), 6.96 (1H, m), 7.19 (1H, d), 7.42 (1H, m) (4H obscured) | C1 |

| Example Number | Structure | Characterisation Data | Route |
|---|---|---|---|
| 35 | 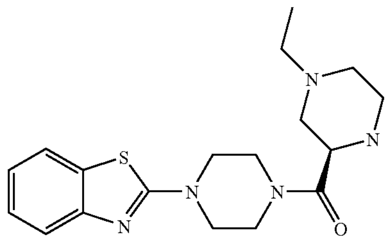 | 2-(4-{[(2R)-4-ethylpiperazin-2-yl]carbonyl}piperazin-1-yl)-1,3-benzothiazole<br>LCMS M/z(+) 360.41 (M + H⁺)<br>¹H NMR (DMSO-d₆) 1.05-1.10 (3H, m), 2.25-2.35 (2H, m), 2.50-2.62 (2H, m), 2.80-2.90 (2H, m), 2.97-3.05 (1H, m), 3.60-3.75 (8H, m), 4.02-4.08 (1H, m), 7.10 (1H, m), 7.30 (1H, m), 7.70 (1H, m). | C1 |
| 36 | 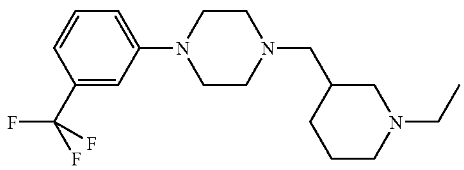 | (3R,S)-1-[(1-ethylpiperidin-3-yl)methyl]-4-[3-(trifluoromethyl)phenyl]piperazine<br>LCMS M/z(+) 355.96 (M + H⁺).<br>¹H NMR (400.132 MHz, CDCl3) 0.83-0.97 (m, 1H), 1.08 (t, 3H), 1.53-1.94 (m, 6H), 2.21 (d, 2H), 2.33-2.47 (m, 2H), 2.47-2.54 (m, 2H), 2.56-2.64 (m, 2H), 2.91 (d, 1H), 3.02 (d, 1H), 3.21 (t, 4H), 7.01-7.07 (m, 2H), 7.10 (s, 1H), 7.31 (t, 1H) | B |
| 37 | 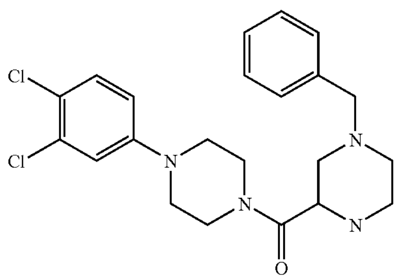 | (3R,S)-1-benzyl-3-{[4-(3,4-dichlorophenyl)piperazin-1-yl]carbonyl}piperazine<br>LCMS M/z(+) 432.83 (M + H⁺).<br>¹H NMR (400.132 MHz, CDCl3) 1.95-2.04 (m, 2H), 2.78 (d, 1H), 2.84 (d, 1H), 2.88-3.00 (m, 2H), 3.04-3.16 (m, 4H), 3.46-3.59 (m, 3H), 3.63-3.78 (m, 3H), 3.82 (dd, 1H), 6.69-6.74 (m, 1H), 6.92 (d, 1H), 7.24-7.37 (m, 6H) | A1 |
| 38 | 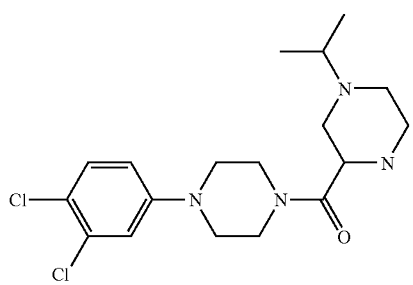 | (3R,S)-3-{[4-(3,4-dichlorophenyl)piperazin-1-yl]carbonyl}-1-isopropylpiperazine<br>LCMS M/z(+) 384.86 (M + H⁺).<br>¹H NMR comparable to chiral material | A2 |
| 39 | 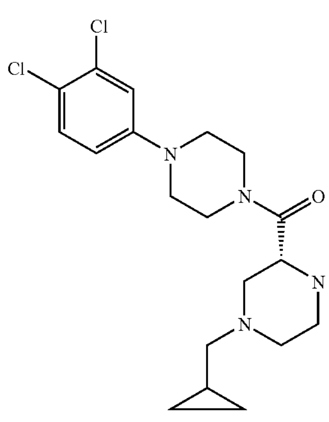 | (3R)-1-(cyclopropylmethyl)-3-{[4-(3,4-dichlorophenyl)piperazin-1-yl]carbonyl}piperazine<br>LCMS M/z(+) 397.35 (M + H⁺)<br>¹H NMR (DMSO-d₆)- 0.01 (2H, m), 0.37 (2H, m), 0.76 (1H, m), 1.82 (2H, m), 2.11 (2H, m), 2.65 (1H, m), 2.74 (1H, m), 2.85 (2H, m), 3.14 (4H, m), 3.58 (6H, m), 6.88 (1H, m), 7.09 (1H, m), 7.35 (1H, m) | A1 |

| Example Number | Structure | Characterisation Data | Route |
|---|---|---|---|
| 40 | 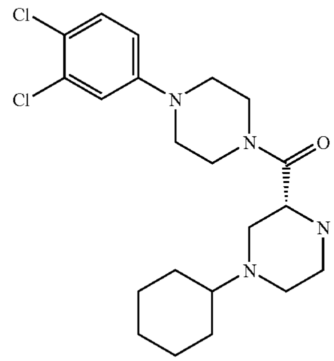 | (3R)-1-cyclohexyl-3-{[4-(3,4-dichloro phenyl)piperazin-1-yl]carbonyl}piperazine<br>LCMS M/z(+) 425.31 (M + H⁺)<br>¹H NMR (300.074 MHz, DMSO-d₆): 1.09 (5H, m), 1.55 (1H, m), 1.71 (4H, m), 2.15 (4H, m), 2.63 (2H, m), 2.76 (1H, m), 2.87 (1H, m), 3.60 (5H, m), 6.93 (1H, m), 7.13 (1H, m), 7.40 (1H, m) (4 H obscured) | A1 |
| 41 | 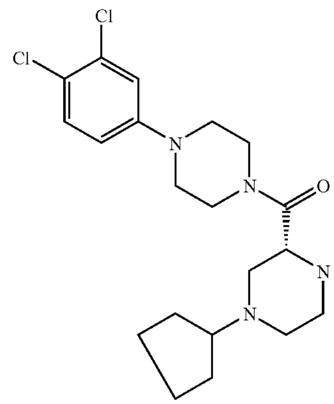 | (3R)-1-cyclopentyl-3-{[4-(3,4-dichloro phenyl)piperazin-1-yl]carbonyl}piperazine<br>LCMS M/z(+) 411.40 (M + H⁺)<br>¹H NMR (400.132 MHz, DMSO): 1.21 (2H, m), 1.38 (2H, m), 1.50 (2H, m), 1.68 (2H, m), 1.79 (2H, m), 2.64 (2H, m), 2.80 (2H, m), 3.09 (4H, m), 3.54 5H, m), 6.87 (1H, m), 7.07 (1H, m), 7.33 (1H, m), (2H obscured) | A1 |
| 42 | 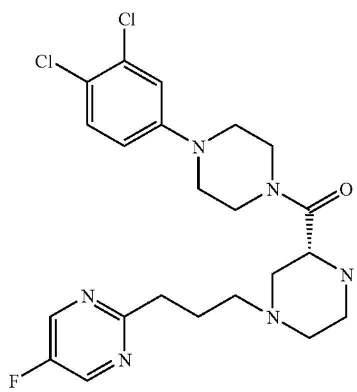 | 2-[3-((3R)-3-{[4-(3,4-dichlorophenyl)piperazin-1-yl]carbonyl}piperazin-1-yl)propyl]-5-fluoropyrimidine<br>LCMS M/z(+) 481.36 (M + H⁺)<br>¹H NMR (DMSO-d₆) ¹H NMR (400.132 MHz, DMSO): 1.86 (4H, m), 2.32 (2H, m), 2.65 (3H, m), 2.77 (1H, m), 2.89 (3H, m), 3.17 (4H, m), 3.60 (6H, m), 6.96 (1H, m), 7.16 (1H, m), 7.42 (1H, m), 8.79 (1H, m) | A1 |
| 43 | 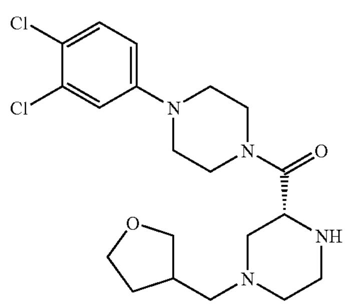 | (3R)-3-{[4-(3,4-dichlorophenyl)piperazin-1-yl]carbonyl}-1-(tetrahydrofuran-3-ylmethyl)piperazine<br>LCMS M/z(+) 427.32 (M + H⁺)<br>¹H NMR (400.132 MHz, DMSO): 1.41 (1H, m), 1.78 (2H, m), 2.15 (2H, m), 2.38 (2H, m), 2.70 (4H, m), 3.16 (4H, m), 3.26 (3H, m), 3.53 (7H, m), 6.87 (1H, m), 7.07 (1H, m), 7.33 (1H, m) | A1 |

-continued

| Example Number | Structure | Characterisation Data | Route |
|---|---|---|---|
| 44 | 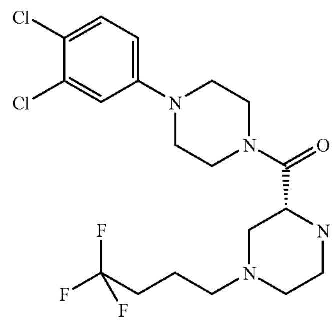 | (3R)-3-{[4-(3,4-dichlorophenyl)piperazin-1-yl]carbonyl}-1-(4,4,4-trifluorobutyl)piperazine<br>LCMS M/z(+) 453.30 (M + H⁺)<br>¹H NMR (DMSO-d₆): 1.63 (2H, m), 1.85 (2H, m), 2.26 (4H, m), 2.70 (4H, m), 2.89 (1H, m), 3.15 (4H, m), 3.60 (5H, m), 6.94 (1H, m), 7.13 (1H, m), 7.40 (1H, m) | A1 |
| 45 | 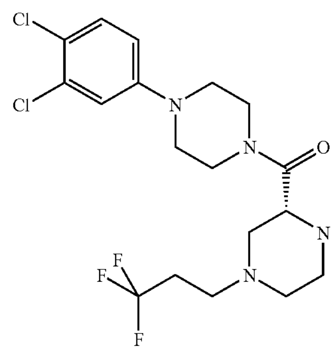 | (3R)-3-{[4-(3,4-dichlorophenyl)piperazin-1-yl]carbonyl}-1-(3,3,3-trifluoropropyl)piperazine<br>LCMS M/z(+) 439.29 (M + H⁺)<br>¹H NMR (DMSO-d₆) | A1 |
| 46 | 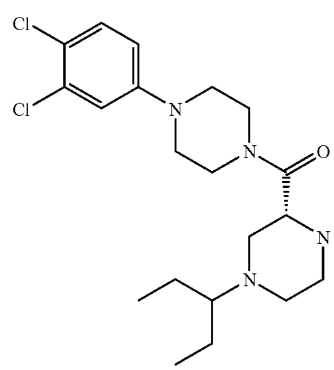 | (3R)-3-{[4-(3,4-dichlorophenyl)piperazin-1-yl]carbonyl}-1-(1-ethylpropyl)piperazine<br>LCMS M/z(+) 413.33 (M + H⁺)<br>¹H NMR (DMSO-d₆) 0.90 (6H, t), 1.25-1.35 (2H, m), 1.40-1.50 (2H, m), 2.15-2.20 (1H, m), 2.55-2.60 (1H, m), 2.65-2.75 (2H, m), 3.25 (4H, m), 3.65 (5H, m), 6.90, dm), 7.10 (1H, m), 7.37 (1H, d), (2H obscured) | A1 |
| 47 | 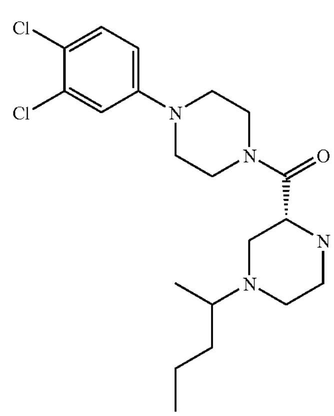 | (3R)-3-{[4-(3,4-dichlorophenyl)piperazin-1-yl]carbonyl}-1-(1-methylbutyl)piperazine<br>LCMS M/z(+) 413.34 (M + H⁺)<br>¹H NMR (DMSO-d₆) 0.85-0.95 (6H, m), 1.20-1.30 (1H, m), 1.30-1.40 (2H, m), 1.45-1.55 (1H, m), 2.12-2.22 (1H, m), 2.27-2.37 (1H, m), 2.50-2.62 (2H, m), 2.70-2.80 (2H, m), 3.20-3.25 (4H, m), 3.60-3.70 (4H, m), 3.70-3.80 (1H, m), 6.90 (1H, m), 7.10 (1H, m), 7.38 (1H, m), (2H obscured) | A1 |

-continued

| Example Number | Structure | Characterisation Data | Route |
|---|---|---|---|
| 48 | 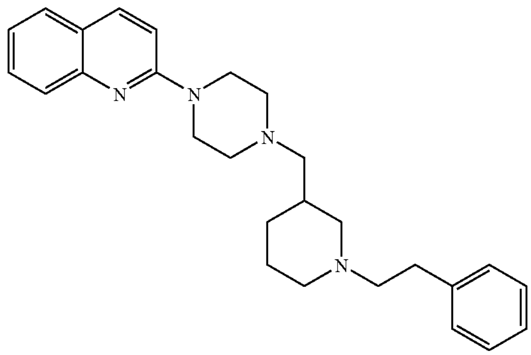 | (3R,S)-1-({1-[2-phenyl]ethyl}piperidin-3-yl methyl)-4-(2-quinolinyl)piperazine LCMS M/z(+) 415.34 (M + H⁺). ¹H NMR (400.132 MHz, DMSO) 1.9 (m, 5H), 2.4-3.4 (m, 14H), 3.7 (m, 4H), 7.2 (m, 7H), 7.5 (m, 2H), 7.7 (d, 1H), 8.0 (d, 1H) | D |
| 49 | 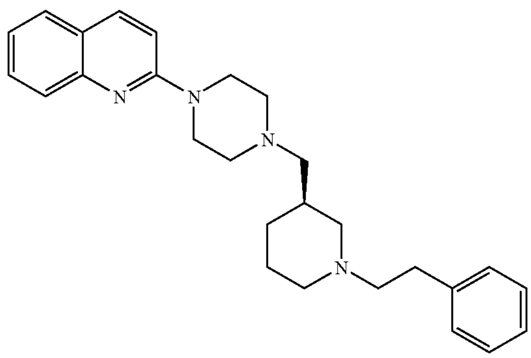 | (3R)-1-({1-[2-phenyl]ethyl}piperidin-3-yl methyl)-4-(2-quinolinyl)piperazine LCMS M/z(+) 414.96 (M + H⁺). ¹H NMR (400.132 MHz, DMSO) 0.9 (m, 1H), 1.6 (m, 4H), 2.0-3.6(m, 18H), 7.2 (m, 7H), 7.5 (m, 2H), 7.65 (d, 1H), 8.0 (d, 1H) | D |
| 50 | 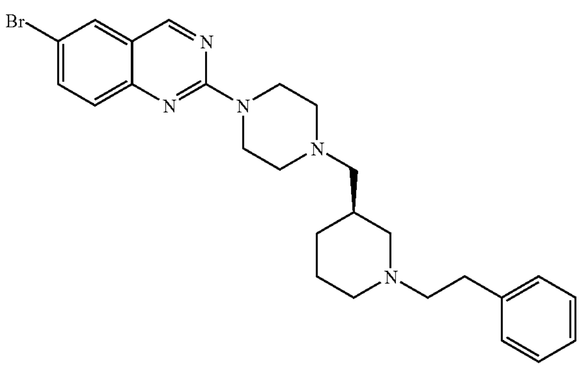 | (3R)-4-(6-bromoquinazolin-2-yl)-1-({1-[2-phenyl]ethyl}piperidin-3-ylmethyl)piperazine LCMS M/z(+) 495.82 (M + H⁺). ¹H NMR (400.132 MHz, DMSO) 0.9 (m, 1H), 1.4 (m, 4H), 1.8-3.5(m, 14H), 3.9 (m, 4H), 7.2 (m, 5H), 7.4 (d, 1H), 7.8 (m, 1H), 8.05 (s, 1H), 9.15 (s, 1H) | D |
| 51 | 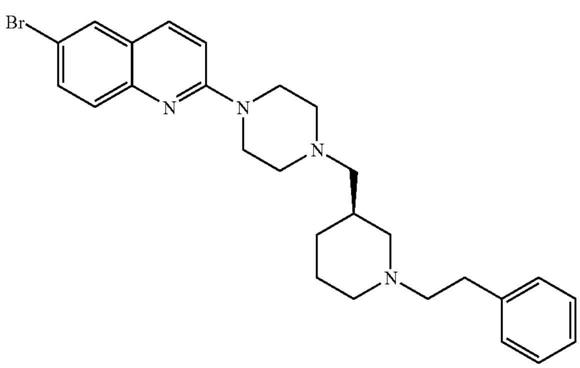 | (3R)-4-(6-bromoquinolin-2-yl)-1-({1-[2-phenyl]ethyl}piperidin-3-ylmethyl)piperazine LCMS M/z(+) 492.94 (M + H⁺). ¹H NMR (400.132 MHz, DMSO) 1.6 (m, 5H), 2.2-3.7 (m, 18H), 7.2(m, 6H), 7.45 (d, 1H), 7.6 (d, 1H), 7.9 (s, 1H), 8.0 (d, 1H) | D |

| Example Number | Structure | Characterisation Data | Route |
|---|---|---|---|
| 52 | 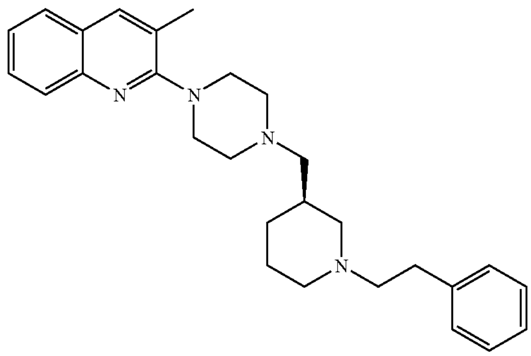 | (3R)-4-(3-methylquinolin-2-yl)-1-({1-[2-phenyl]ethyl}piperidin-3-ylmethyl)piperazine<br>LCMS M/z(+) 429.06 (M + H⁺).<br>$^1$H NMR (400.132 MHz, DMSO) 0.9 (m, 1H), 1.7 (m, 4H), 2.0-3.4(m, 21H), 7.2 (m, 7H), 7.5 (t, 1H), 7.7 (t, 1H), 7.95 (s, 1H) | D |
| 53 | 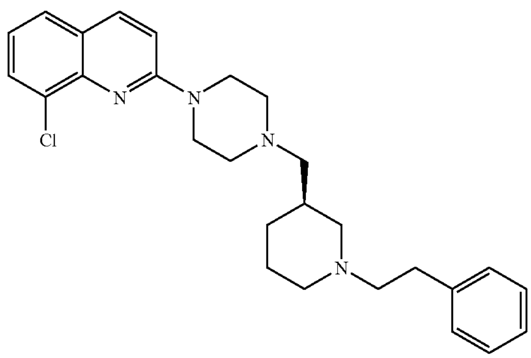 | (3R)-4-(8-chloroquinolin-2-yl)-1-({1-[2-phenyl]ethyl}piperidin-3-ylmethyl)piperazine<br>LCMS M/z(+) 449.00 (M + H⁺).<br>$^1$H NMR (400.132 MHz, DMSO) 1.6 (m, 5H), 2.2-3.4 (m, 14H), 3.85(m, 4H), 7.2 (m, 7H), 7.65 (m, 2H), 8.1 (d, 1H) | D |
| 54 | 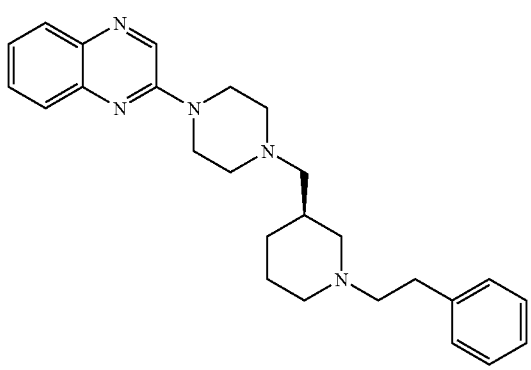 | (3R)-4-(quinoxalin-2-yl)-1-({1-[2-phenyl]ethyl}piperidin-3-ylmethyl)piperazine<br>LCMS M/z(+) 416.07 (M + H⁺).<br>$^1$H NMR (400.132 MHz, DMSO) 0.9 (m, 1H), 1.7 (m, 4H), 2.2(m, 2H), 2.5-3.5 (m, 12H), 3.75 (m, 4H), 7.2 (m, 5H), 7.3 (m, 1H), 7.6 (m, 2H), 7.8 (d, 1H), 8.8 (s, 1H) | D |
| 55 | 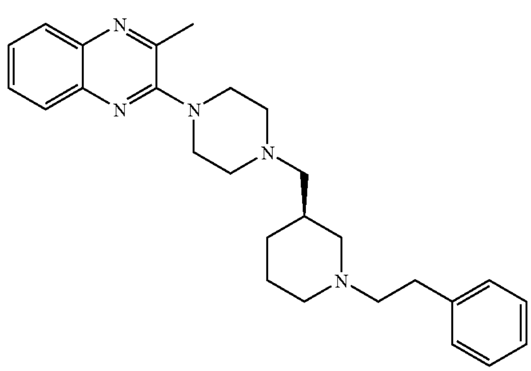 | (3R)-4-(3-methylquinoxalin-2-yl)-1-({1-[2-phenyl]ethyl}piperidin-3-ylmethyl)piperazine<br>LCMS M/z(+) 429.98 (M + H⁺).<br>$^1$H NMR (400.132 MHz, DMSO) 0.9 (m, 1H), 1.7 (m, 4H), 2.2(m, 2H), 2.6 (m, 6H), 2.65 (s, 3H), 2.8 (m, 4H), 3.4 (m, 6H), 7.2 (m, 5H), 7.6 (m, 2H), 7.75 (d, 1H), 7.85 (d, 1H) | D |

| Example Number | Structure | Characterisation Data | Route |
|---|---|---|---|
| 56 | 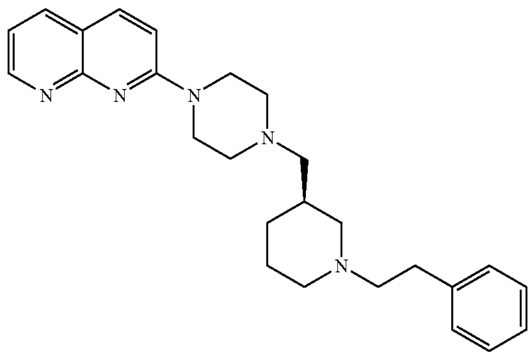 | (3R)-4-(1,8-naphthyridin-2-yl)-1-({1-[2-phenyl]ethyl}piperidin-3-ylmethyl)piperazine<br>LCMS M/z(+) 416.06 (M + H$^+$).<br>$^1$H NMR (400.132 MHz, DMSO) 0.9 (m, 1H), 1.7 (m, 4H), 2.2(m, 3H), 2.5 (m, 4H), 2.8 (m, 4H), 3.4 (m, 3H), 3.75 (m, 4H), 7.2 (m, 7H), 8.1 (m, 2H), 8.7 (m, 1H) | D |
| 57 | 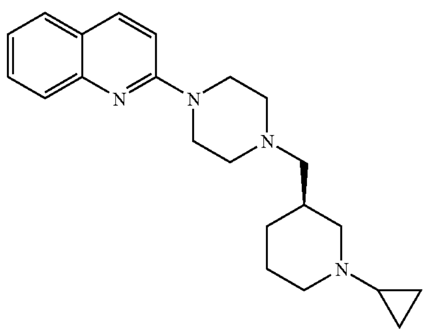 | (3R)-1-({1-cyclopropyl}piperidin-3-yl methyl)-4-(2-quinolinyl)piperazine<br>LCMS M/z(+) 351.42 (M + H$^+$).<br>$^1$H NMR (400.132 MHz, DMSO) 0.0 (m, 2H), 0.1 (m, 2H), 1.5 (m, 5H), 2.1-3.2 (m, 11H), 3.4 (m, 4H), 6.9 (m, 2H), 7.25 (m, 2H), 7.4 (d, 1H), 7.7 (d, 1H) | D |
| 58 | 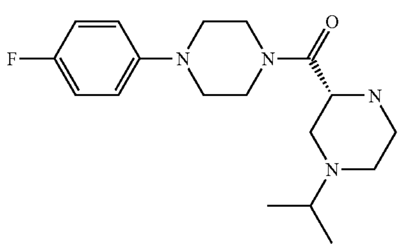 | (3R)-3-{[4-(4-fluorophenyl)piperazin-1-yl]carbonyl}-1-isopropylpiperazine<br>LCMS M/z(+) 335.44 (M + H$^+$) | C1 |
| 59 | 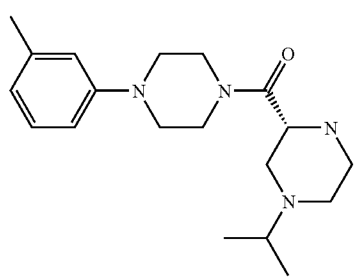 | (3R)-1-isopropyl-3-{[4-(3-methylphenyl)piperazin-1-yl]carbonyl}piperazine<br>LCMS M/z(+) 331.46 (M + H$^+$) | C1 |
| 60 | 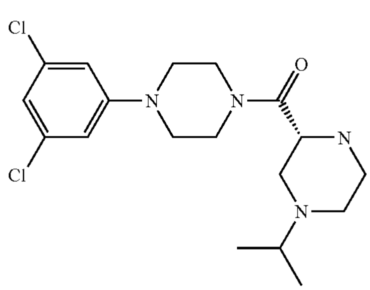 | (3R)-3-{[4-(3,5-dichlorophenyl)piperazin-1-yl]carbonyl}-1-isopropyl piperazine<br>LCMS M/z(+) 385.50 (M + H$^+$) | C1 |

-continued

| Example Number | Structure | Characterisation Data | Route |
|---|---|---|---|
| 61 | 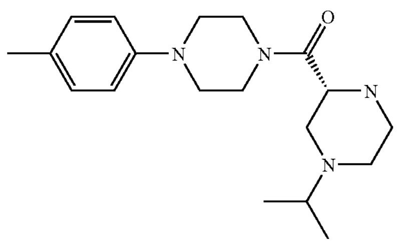 | (3R)-1-isopropyl-3-{[4-(4-methylphenyl)piperazin-1-yl]carbonyl}piperazine<br>LCMS M/z(+) 331.47 (M + H⁺) | C1 |
| 62 | 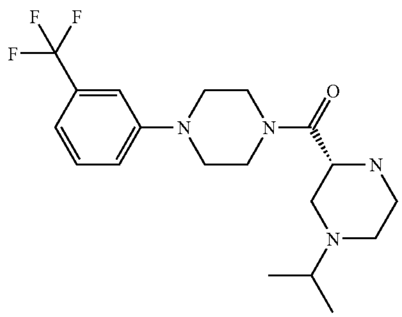 | (3R)-1-isopropyl-3-({4-[3-(trifluoromethyl)phenyl]piperazin-1-yl}carbonyl)piperazine<br>LCMS M/z(+) 385.44 (M + H⁺) | C1 |
| 63 | 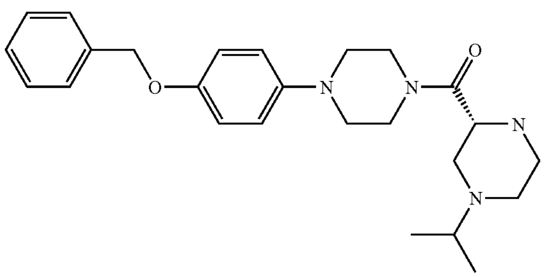 | (3R)-3-({4-[4-(benzyloxy)phenyl]piperazin-1-yl}carbonyl)-1-isopropyl piperazine<br>LCMS M/z(+) 423.71 (M + H⁺) | C1 |
| 64 | 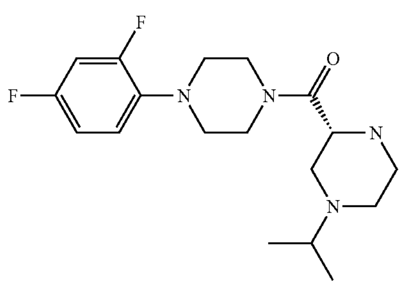 | (3R)-3-{[4-(2,4-difluorophenyl)piperazin-1-yl]carbonyl}-1-isopropylpiperazine<br>LCMS M/z(+) 353.44 (M + H⁺) | C1 |
| 65 | 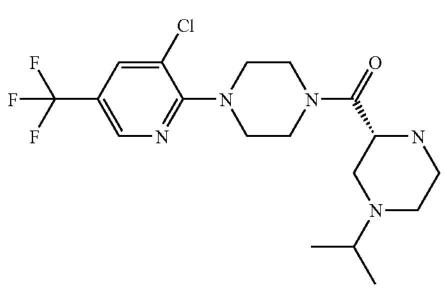 | (3R)-3-({4-[3-chloro-5-(trifluoromethyl) pyridin-2-yl]piperazin-1-yl}carbonyl)-1-isopropylpiperazine<br>LCMS M/z(+) 420.18 (M + H⁺) | C1 |

| Example Number | Structure | Characterisation Data | Route |
|---|---|---|---|
| 66 | 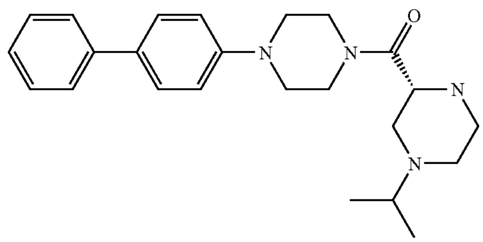 | (3R)-3-[(4-biphenyl-4-ylpiperazin-1-yl)carbonyl]-1-isopropylpiperazine LCMS M/z(+) 393.51 (M + H$^+$) | C1 |
| 67 | 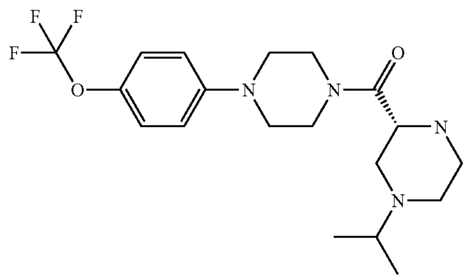 | (3R)-1-isopropyl-3-({4-[4-(trifluoromethoxy)phenyl]piperazin-1-yl}carbonyl)piperazine LCMS M/z(+) 401.48 (M + H$^+$) | C1 |
| 68 | 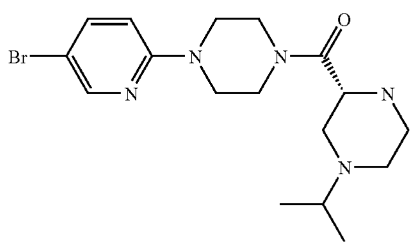 | (3R)-3-{[4-(5-bromopyridin-2-yl)piperazin-1-yl]carbonyl}-1-isopropylpiperazine LCMS M/z(+) 396.33 (M + H$^+$) | C1 |
| 69 | 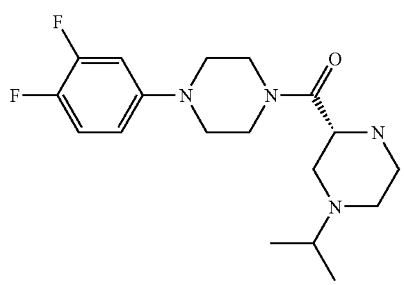 | (3R)-3-{[4-(3,4-difluorophenyl)piperazin-1-yl]carbonyl}-1-isopropylpiperazine LCMS M/z(+) 353.42 (M + H) $^1$H-NMR (CDCl$_3$): δ 1.00-1.10 (6H, m), 2.07-2.23 (2H, m), 2.54-2.98 (4H, m), 3.02-3.16 (5H, m), 3.58-3.89 (5H, m), 6.59 (1H, m), 6.72 (1H, m) and 7.07 (1H, m) | C1 |
| 70 | 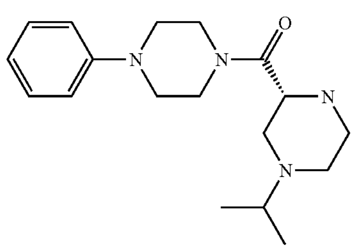 | (3R)-1-isopropyl-3-[(4-phenylpiperazin-1-yl)carbonyl]piperazine LCMS M/z(+) 316.45 (M + H$^+$) | C1 |
| 71 | 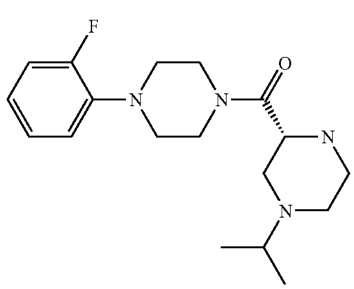 | (3R)-3-{[4-(2-fluorophenyl)piperazin-1-yl]carbonyl}-1-isopropylpiperazine LCMS M/z(+) 335.43 (M + H$^+$) | C1 |

-continued

| Example Number | Structure | Characterisation Data | Route |
|---|---|---|---|
| 72 | 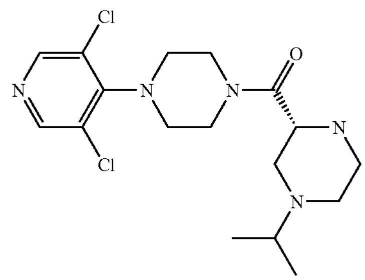 | (3R)-3-{[4-(3,5-dichloropyridin-4-yl)piperazin-1-yl]carbonyl}-1-isopropylpiperazine<br>LCMS M/z(+) 386.26 (M + H$^+$) | C1 |
| 73 | 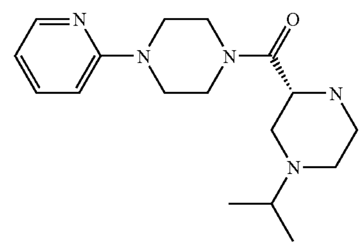 | (3R)-1-isopropyl-3-[(4-pyridin-2-ylpiperazin-1-yl)carbonyl]piperazine<br>LCMS M/z(+) 318.46 (M + H$^+$) | C1 |
| 74 | 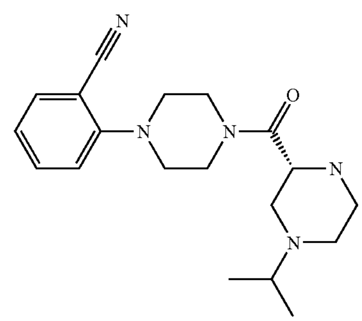 | 2-(4-{[(2R)-4-isopropylpiperazin-2-yl]carbonyl}piperazin-1-yl)benzonitrile<br>LCMS M/z(+) 342.48 (M + H$^+$) | C1 |
| 75 | 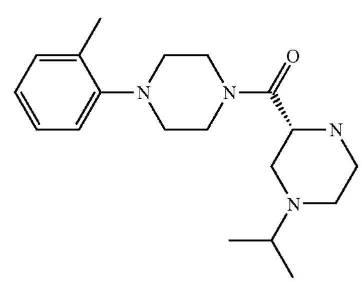 | (3R)-1-isopropyl-3-{[4-(2-methylphenyl)piperazin-1-yl]carbonyl}piperazine<br>LCMS M/z(+) 331.49 (M + H$^+$) | C1 |
| 76 | 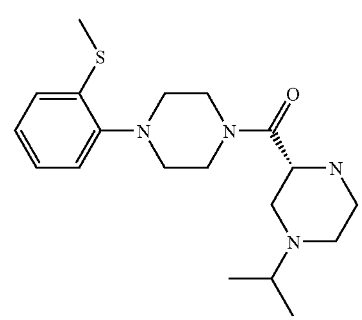 | (3R)-1-isopropyl-3-({4-[2-(methylthio)phenyl]piperazin-1-yl}carbonyl)piperazine<br>LCMS M/z(+) 363.45 (M + H$^+$) | C1 |

-continued

| Example Number | Structure | Characterisation Data | Route |
|---|---|---|---|
| 77 | 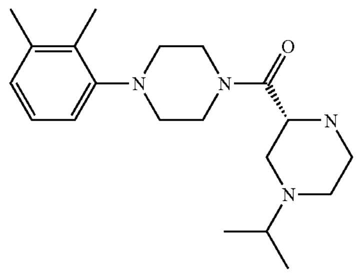 | (3R)-3-{[4-(2,3-dimethylphenyl)piperazin-1-yl]carbonyl}-1-isopropylpiperazine LCMS M/z(+) 345.53 (M + H$^+$) | C1 |
| 78 | 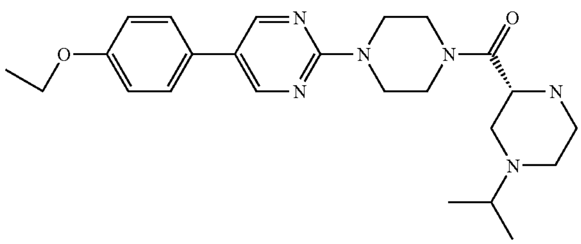 | 5-(4-ethoxyphenyl)-2-(4-{[(2R)-4-isopropylpiperazin-2-yl]carbonyl}piperazin-1-yl)pyrimidine LCMS M/z(+) 439.79 (M + H$^+$) | C1 |
| 79 | 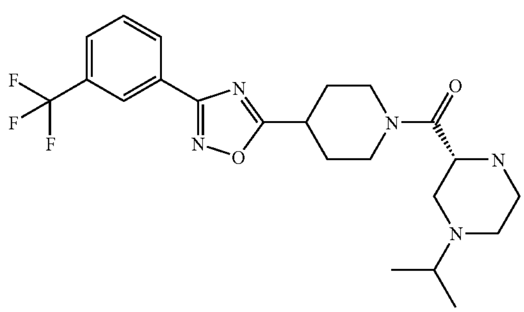 | (3R)-1-isopropyl-3-[(4-{3-[3-(trifluoro methyl)phenyl]-1,2,4-oxadiazol-5-yl}piperidin-1-yl)carbonyl]piperazine LCMS M/z(+) 452.60 (M + H$^+$) | C1 |
| 80 | 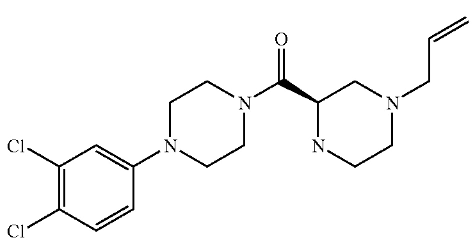 | (3R)-3-{[4-(3,4-dichlorophenyl)piperazin-1-yl]carbonyl}-1-(prop-2-en-1-yl)piperazine LCMS M/z(+) 383.37 (M + H$^+$) $^1$H NMR (500.133 MHz, DMSO-d$_6$): 2.06 (2H, m), 2.73 (1H, m), 2.81 (2H, m), 3.01 (3H, m), 3.23 (4H, m), 3.64 (4H, m), 3.86 (1H, m), 5.17 (2H, m), 5.83 (1H, m), 6.90 (1H, m), 7.08 (1H, m), 7.36 (1H, m) | C1 |
| 81 | 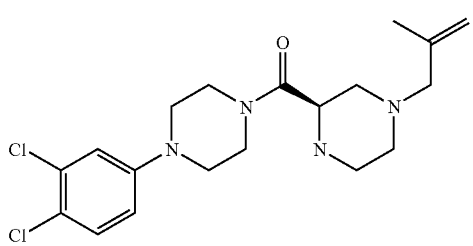 | (3R)-3-{[4-(3,4-dichlorophenyl)piperazin-1-yl]carbonyl}-1-(2-methylprop-2-en-1-yl)piperazine LCMS M/z(+) 397.34 (M + H$^+$) $^1$H NMR (500.133 MHz, DMSO-d$_6$): 1.71 (3H, m), 1.91 (2H, m), 2.63 (1H, m), 2.75 (2H, m), 2.85 (2H, m), 2.95 (1H, m), 3.22 (4H, m), 3.64 (4H, m), 3.70 (1H, m), 4.86 (2H, m), 6.90 (1H, m), 7.08 (1H, m), 7.36 (1H, m), (1H obscured) | C1 |

| Example Number | Structure | Characterisation Data | Route |
|---|---|---|---|
| 82 | 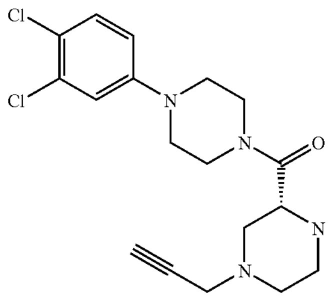 | (3R)-3-{[4-(3,4-dichlorophenyl) piperazin-1-yl]carbonyl}-1-(prop-2-yn-1-yl)piperazine<br>LCMS M/z(+) 381.19 (M + H+)<br>1H NMR (499.803 MHz, DMSO-d6): 2.11 (3H, m), 2.64 (2H, m), 2.75 (3H, m), 3.23 (6H, m), 3.66 (5H, m), 6.90 (1H, m), 7.08 (1H, m), 7.36 (1H, m) | C1 |
| 83 | 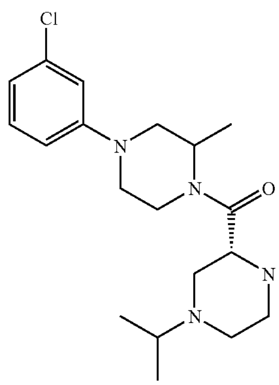 | (3R,)-3-{[4-(3-chlorophenyl)-2-methyl piperazin-1-yl]carbonyl}-1-isopropyl piperazine<br>LCMS M/z(+) 365.26 (M + H+)<br>1H NMR (500.133 MHz, DMSO-d6): 0.98 (9H, m), 2.09 (2H, m), 2.70 (4H, m), 3.08 (1H, m), 3.28 (3H, m), 3.66 (1H, m), 4.00 (3H, m), 6.76 (1H, m), 6.85 (2H, m), 7.20 (1H, m) | C1 |
| 84 | 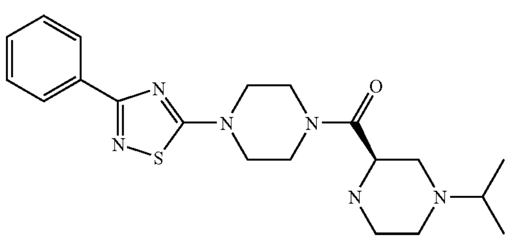 | (3R)-3-{[4-(4-Phenyl-1,2,4-thiadiazol-2-yl)piperazin-1-yl]carbonyl}-1-(isopropyl)piperazine<br>LCMS M/z(+) 401.31 (M + H+)<br>1H NMR (500.130 MHz, DMSO-d6 at 373° K: 0.99 (6H, d)2/06-2.16 (2H, m), 2.62-2.68 (2H, m), 2.72 (1H, dt), 2.78 (1H, td3.60-3.68 (5H, m), 3.73-3.77 (4H, m), 7.46 (3H, m), 8.12 (2H, m). | C1 |
| 85 | 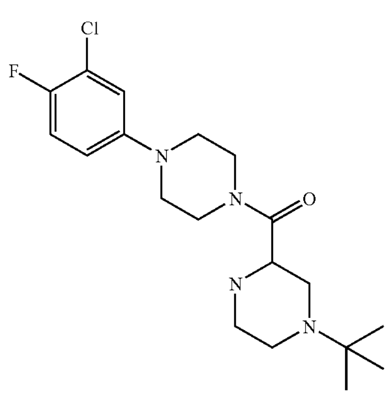 | 3-{[4-(3-Chloro-4-fluorophenyl) piperazin-1-yl]carbonyl}-1-t-butyl piperazine<br>LCMS M/z(+) 383.44 (M + H+).<br>1H-NMR (500.130 MHz, DMSO-d6): 0.97 (9H, s), 1.92 (1H, t), 1.96 (1H, dt), 2.61-2.65 (1H, m), 2.76 (1H, brd), 2.87-2.94 (2H, m), 3.05 (1H, br), 3.09-3.19 (3H, m), 3.53 (1H, br), 3.56-3.65 (3H, m), 3.68 (1H, br), 6.94 (1H, td), 7.09 (1H, dd), 7.24 (1H, t). | C1 |

| Example Number | Structure | Characterisation Data | Route |
|---|---|---|---|
| 86 | 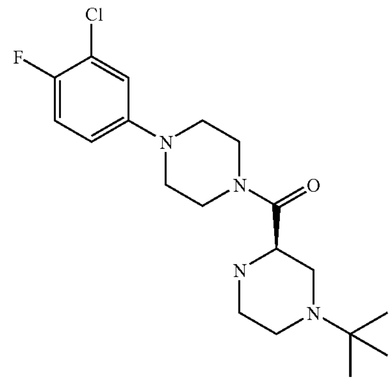 | (3R)-3-{[4-(3-Chloro-4-fluorophenyl)piperazin-1-yl]carbonyl}-1-t-butyl piperazine<br>LCMS M/z(+) 383.29 (M + H+).<br>$^1$H-NMR (500.130 MHz, DMSO-$d_6$ at 373° K): 1.01 (9H, s), 2.03 (2H, t), 2.67 (1H, dt), 2.78 (1H, brd), 2.87-2.98 (obscured), m), 3.11-3.20 (4H, m), 3.61 (1H, dd), 3.62-3.66 (4H, m), 6.91 (1H, m), 7.03 (1H, dd), 7.19 (1H, t). | Chiral separation |
| 87 | 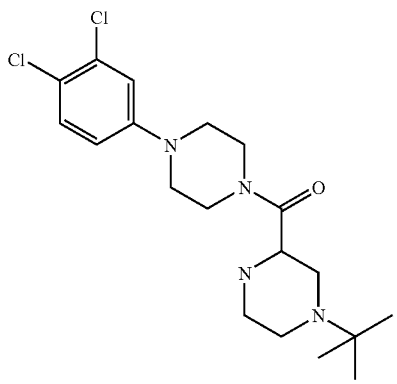 | [4-(3,4-Dichlorophenyl)piperazin-1-yl]-((2R,2S)-4-tert-butylpiperazin-2-yl]methanone<br>LCMS M/z(+) 399 (M + H+).<br>NMR: as for Example 89 | C1 |
| 88 | 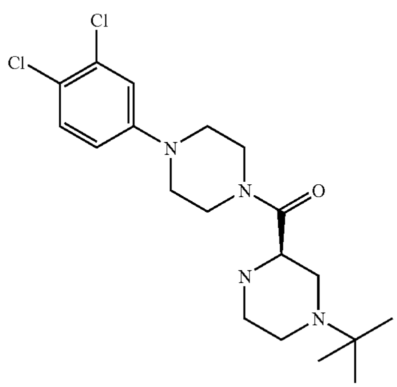 | [4-(3,4-Dichlorophenyl)piperazin-1-yl]-[(2R)-4-tert-butylpiperazin-2-yl]methanone<br>LCMS M/z(+) 399 (M + H+).<br>NMR: as for Example 89<br>First eluted enantiomer | Chiral separation |
| 89 | 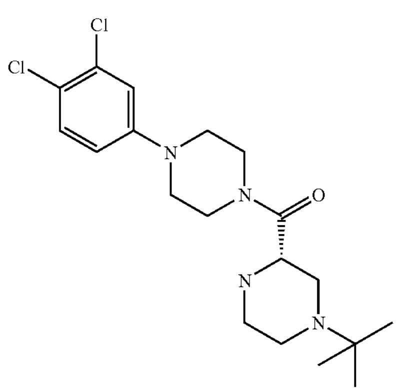 | [4-(3,4-Dichlorophenyl)piperazin-1-yl]-[(2S)-4-tert-butylpiperazin-2-yl]methanone<br>LCMS M/z(+) 399 (M + H+).<br>$^1$H NMR (400.132 MHz, CDCl3) 1.06 (s, 9H), 2.02-2.14 (m, 2H), 2.83-2.92 (m, 2H), 2.98-3.04 (m, 1H), 3.06-3.22 (m, 5H), 3.58-3.89 (m, 5H), 6.74 (dd, 1H), 6.96 (d, 1H), 7.29 (d, 1H)<br>Second eluted enantiomer. | Chiral separation |

| Example Number | Structure | Characterisation Data | Route |
|---|---|---|---|
| 90 | 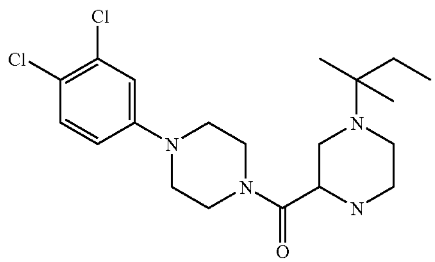 | [4-(3,4-Dichlorophenyl)piperazin-1-yl]-[(2R,2S)-4-(2-methylbutan-2-yl)piperazin-2-yl]methanone<br>LCMS M/z(+) 413 (M + H$^+$).<br>$^1$H NMR (400.132 MHz, CDCl3) 0.86 (t, 3H), 0.99 (s, 6H), 1.44 (q, 2H), 2.05-2.20 (m, 2H), 2.77-2.99 (m, 3H), 3.04-3.24 (m, 5H), 3.58-3.89 (m, 5H), 6.74 (dd, 1H), 6.96 (d, 1H), 7.29 (d, 1H) | C1 |
| 91 | 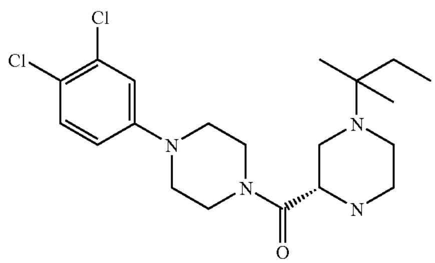 | [4-(3,4-Dichlorophenyl)piperazin-1-yl]-[(2S)-4-(2-methylbutan-2-yl)piperazin-2-yl]methanone<br>LCMS M/z(+) 413 (M + H$^+$).<br>NMR: as Example 90<br>Second eluted enantiomer | Chiral separation |
| 92 | 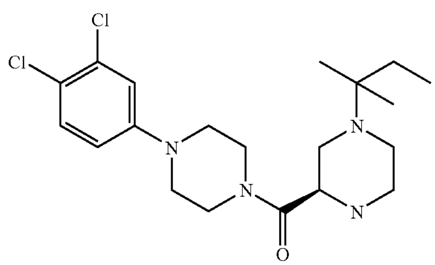 | [4-(3,4-Dichlorophenyl)piperazin-1-yl]-[(2R)-4-(2-methylbutan-2-yl)piperazin-2-yl]methanone<br>LCMS M/z(+) 413 (M + H$^+$).<br>NMR: as Example 90<br>First eluted enantiomer | Chiral separation |
| 93 | 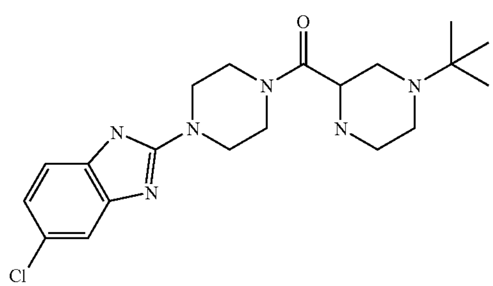 | [4-(5-Chloro-1H-benzoimidazol-2-yl)piperazin-1-yl]-((2R,2S)-4-tert-butylpiperazin-2-yl)methanone<br>LCMS M/z(+) 405, 407 (M + H$^+$).<br>$^1$H NMR (400.132 MHz, CDCl$_3$) 1.02 (s, 9H), 2.05 (m 2H), 2.75 (m, 2H), 2.98 (m, 2H), 3.65 (m, 9H), 6.95 (m, 1H), 7.18 (m, 2H). | C1 |
| 94 | 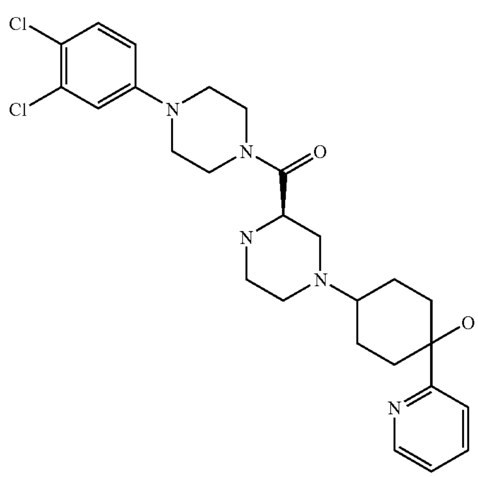 | 4-((3R)-3-{[4-(3,4-dichlorophenyl)piperazin-1-yl]carbonyl}piperazin-1-yl)-1-pyridin-2-ylcyclohexanol<br>LCMS M/z(+) 517.83 (M + H$^+$).<br>$^1$H NMR (400.132 MHz, DMSOd6) 1.4 (m, 2H), 1.6 (m, 2H), 1.8 (m, 4H), 2.2 (m, 1H), 2.35 (t, 2H), 2.7 (m, 2H), 2.9 (t, 2H), 3.2 (m, 6H), 3.6 (m, 4H), 4.95 (s, 1H), 6.9 (d, 1H), 7.1 (s, 1H), 7.2 (m, 1H), 7.4 (d, 1H), 7.6 (d, 1H), 7.75 t, 1H), 8.5 (d, 1H). | TFA deprotection |

Table of Intermediates for Examples

| Example No. | Structure | Characterisation Data | Route |
|---|---|---|---|
| Int1 | 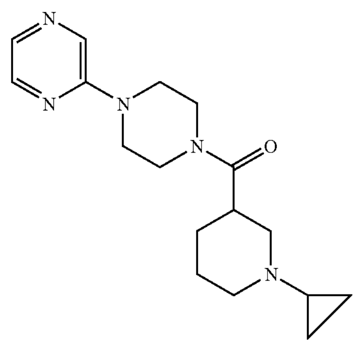 | 2-{4-[(1-cyclopropylpiperidin-3-yl)carbonyl]piperazin-1-yl}pyrazine<br>LCMS M/z(+) 316.34 (M + H$^+$)<br>$^1$H-NMR (CDCl$_3$): 0.30-0.46 (m, 4H), 1.50 (t, 2H), 1.54-1.75 (m, 2H), 2.09 (t, 1H), 2.32 (t, 1H), 2.48-3.00 (m, 5H), 3.47-3.74 (m, 4H), 7.85 (dd, 1H), 8.00 (d, 1H) and 8.08 (d, 1H) | A1 |
| Int2 | 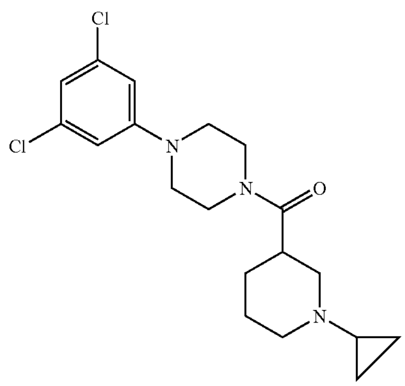 | 1-[(1-cyclopropylpiperidin-3-yl)carbonyl]-4-(3,5-dichlorophenyl)piperazine<br>LCMS M/z(+) 382.23 (M + H$^+$) | A1 |
| Int3 | 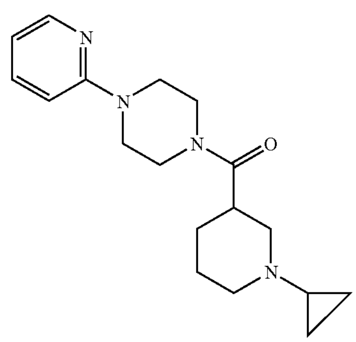 | 1-[(1-cyclopropylpiperidin-3-yl)carbonyl]-4-pyridin-2-ylpiperazine<br>LCMS M/z(+) 328.29 (M + H$^+$) | A1 |
| Int4 | 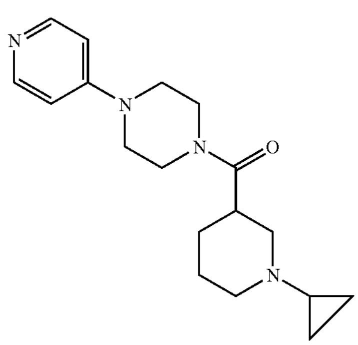 | 1-[(1-cyclopropylpiperidin-3-yl)carbonyl]-4-pyridin-4-ylpiperazine<br>LCMS M/z(+) 328.24 (M + H$^+$) | A1 |

Table of Intermediates for Examples

| Example No. | Structure | Characterisation Data | Route |
|---|---|---|---|
| Int5 | 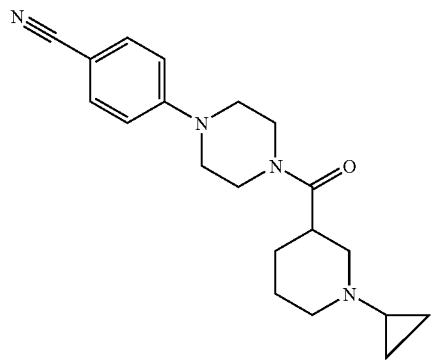 | 4-{4-[(1-cyclopropylpiperidin-3-yl)carbonyl]piperazin-1-yl}benzonitrile<br>LCMS M/z(+) 339.40 (M + H⁺) | A1 |
| Int6 | 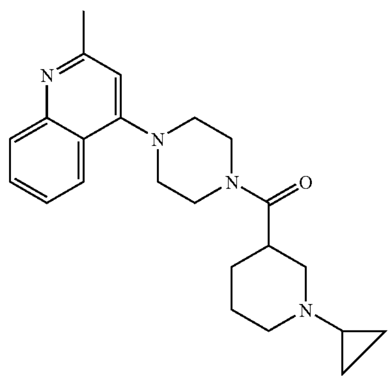 | 4-{4-[(1-cyclopropylpiperidin-3-yl)carbonyl]piperazin-1-yl}-2-methyl quinoline<br>LCMS M/z(+) 379.32 (M + H⁺) | A1 |
| Int7 | 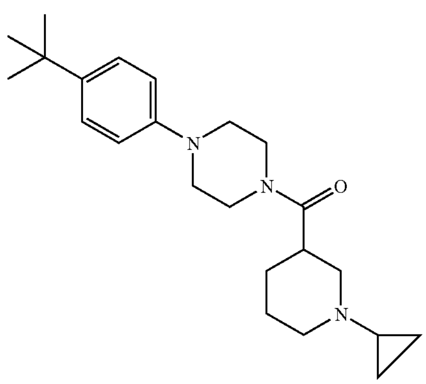 | 1-(4-tert-butylphenyl)-4-[(1-cyclopropylpiperidin-3-yl)carbonyl]piperazine<br>LCMS M/z(+) 370.45 (M + H⁺) | A1 |
| Int8 | 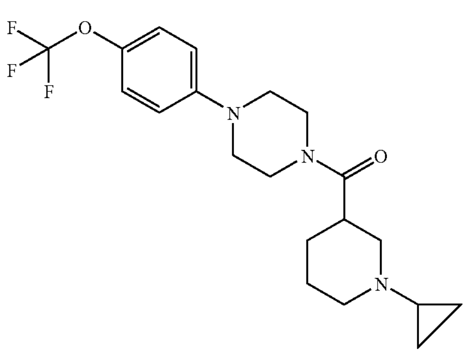 | 1-[(1-cyclopropylpiperidin-3-yl)carbonyl]-4-[4-(trifluoromethoxy)phenyl]piperazine<br>LCMS M/z(+) 398.39 (M + H⁺) | A1 |

Table of Intermediates for Examples

| Example No. | Structure | Characterisation Data | Route |
|---|---|---|---|
| Int9 | 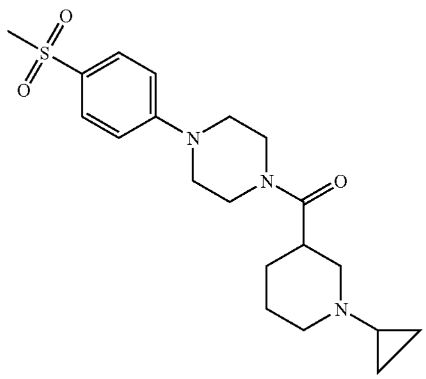 | 1-[(1-cyclopropylpiperidin-3-yl)carbonyl]-4-[4-(methylsulfonyl)phenyl]piperazine<br>LCMS M/z(+) 392.33 (M + H$^+$) | A1 |
| Int10 | 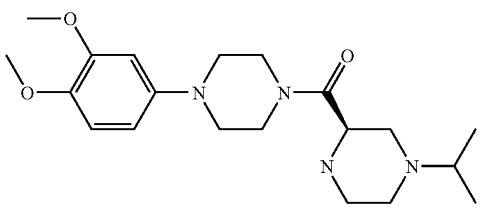 | (3R)-3-{[4-(3,4-dimethoxyphenyl)piperazin-1-yl]carbonyl}-1-isopropyl piperazine<br>LCMS M/z(+) 379 (M + H$^+$).<br>$^1$H NMR (400.132 MHz, DMSO) 0.96-1.06 (m, 6H), 2.06-2.26 (m, 2H), 2.65-2.87 (m, 4H), 2.93-3.21 (m, 5H), 3.46-3.93 (m, 11H), 6.47 (dd, 1H), 6.69 (d, 1H), 6.87 (d, 1H) | C1 |
| Int11 | 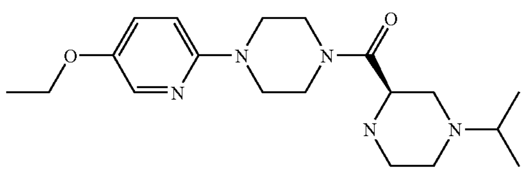 | (3R)-3-{[4-(5-ethoxypyridin-2-yl)piperazin-1-yl]carbonyl}-1-isopropyl piperazine<br>LCMS M/z(+) 362 (M + H$^+$).<br>$^1$H NMR (400.132 MHz, CDCl$_3$) 1.36-1.46 (m, 9H), 3.37-3.93 (m, 13H), 3.95-4.15 (m, 4H), 4.85-4.98 (m, 1H), 6.96-7.01 (m, 1H), 7.58-7.67 (m, 2H) | C1 |
| Int12 | 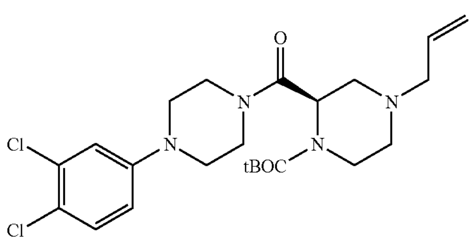 | (3R)-4-tert-butoxycarbonyl-3-{[4-(3,4-dichlorophenyl)piperazin-1-yl]carbonyl}-1-(prop-2-en-1-yl)piperazine<br>LCMS M/z(+) 483.33 (M + H$^+$).<br>$^1$H-NMR (DMSO-d$_6$): 1.38 (9H, brs), 1.95 (1H, dt), 2.02 (1H, brs), 2.7-2.8 (1H, obscured), 2.9-3.05 (2H, m), 3.1-3.25 (4H, m), 3.4-3.7 (7H, m), 4.83 (1H, bd), 5.11 (1H, d), 5.18 (1H, d), 5.7-5.8 (1H, m), 6.98 (1H, dd), 7.19 (1H, d), 7.43 (1H, d) | C1 |
| Int13 | 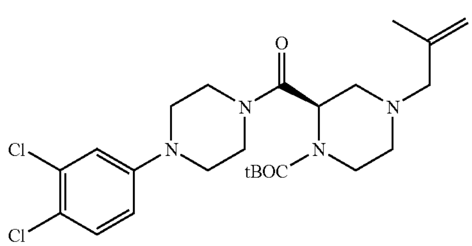 | (3R)-4-tert-butoxycarbonyl-3-{[4-(3,4-dichlorophenyl)piperazin-1-yl]carbonyl}-1-(2-methylprop-2-en-1-yl)piperazine<br>LCMS M/z(+) 497.36 (M + H$^+$).<br>$^1$H-NMR (DMSO-d$_6$): 1.36, 1.41 (9H, 2 x s), 1.60 (3H, s), 1.99 (1H, dt), 2.09 (1H, brs), 2.6-2.8 (2H, m), 2.86-3.0 (2H, m), 3.0-3.25 (3H, br), 3.4-3.7 (7H, br), 4.8-4.92 (1H + 2H, m + d), 6.97 (1H, dd), 7.18 (1H, d), 7.43 (1H, d) | C1 |

Table of Intermediates for Examples

| Example No. | Structure | Characterisation Data | Route |
|---|---|---|---|
| Int14 | 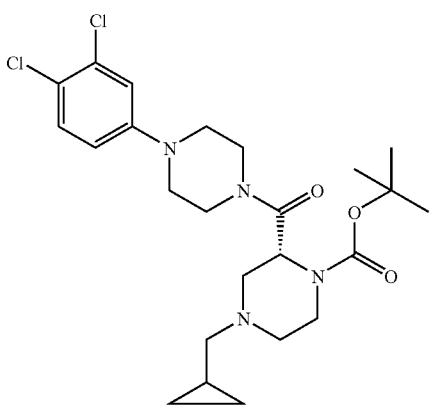 | tert-butyl (2R)-4-(cyclopropylmethyl)-2-{[4-(3,4-dichlorophenyl)piperazin-1-yl]carbonyl}piperazine-1-carboxylate<br>LCMS M/z(+) 499.40 (M + H⁺)<br>¹H NMR (500.133 MHz, DMSO-d₆): 0.16 (2H, m), 0.50 (2H, m), 0.87 (1H, m), 1.39 (9H, m), 1.89 (1H, m), 2.35 (1H, m), 2.43 (1H, m), 2.60 (1H, m), 2.97 (1H, m), 3.21 (4H, m), 3.31 (1H, m), 3.46 (1H, m), 3.62 (4H, m), 3.75 (1H, m), 4.93 (1H, m), 6.88 (1H, m), 7.06 (1H, m), 7.34 (1H, m) | A1 |
| Int15 | 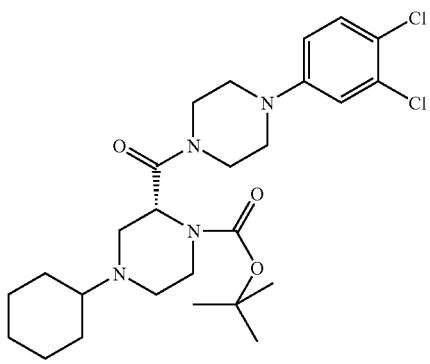 | tert-butyl (2R)-4-cyclohexyl-2-{[4-(3,4-dichlorophenyl)piperazin-1-yl]carbonyl}piperazine-1-carboxylate<br>LCMS M/z(+) 525.39 (M + H)+<br>¹H NMR (400.132 MHz, DMSO-d₆): 1.12 (4H, m), 1.35 (9H, m), 1.62 (4H, m), 1.91 (4H, m), 2.19 (2H, m), 2.73 (1H, m), 3.09 (4H, m), 3.31 (2H, m), 3.59 (4H, m), 4.79 (1H, m), 6.97 (1H, m), 7.18 (1H, m), 7.43 (1H, m) | A1 |
| Int16 | 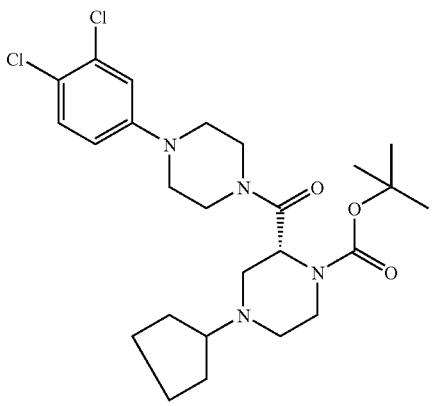 | tert-butyl (2R)-4-cyclopentyl-2-{[4-(3,4-dichlorophenyl)piperazin-1-yl]carbonyl}piperazine-1-carboxylate<br>LCMS M/z(+) 511.44 (M + H⁺)<br>¹H NMR (400.132 MHz, DMSO-d₆): 0.84 (1H, m), 1.44 (13H, m), 1.75 (1H, m), 1.89 (1H, m), 2.23 (1H, m), 2.42 (1H, m), 2.84 (1H, m), 3.02 (1H, m), 3.17 (2H, m), 3.34 (7H, m), 3.59 (3H, m), 4.80 (1H, m), 6.97 (1H, m), 7.19 (1H, m), 7.43 (1H, m) | A1 |

Table of Intermediates for Examples

| Example No. | Structure | Characterisation Data | Route |
|---|---|---|---|
| Int17 | 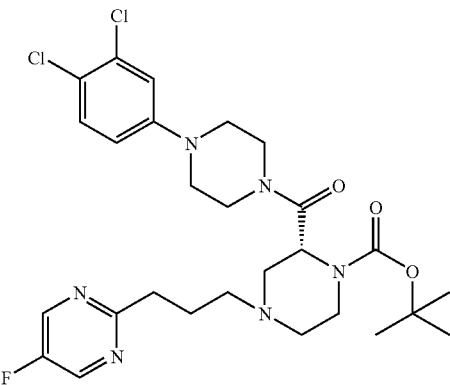 | tert-butyl (2R)-2-{[4-(3,4-dichlorophenyl)piperazin-1-yl]carbonyl}-4-[3-(5-fluoro pyrimidin-2-yl)propyl]piperazine-1-carboxylate<br>LCMS M/z(+) 581.43 (M + H)+<br>$^1$H NMR (399.902 MHz, DMSO-$d_6$): 1.38 (9H, m), 1.88 (3H, m), 2.02 (1H, m), 2.34 (2H, m), 2.84 (3H, m), 3.01 (1H, m), 3.19 (4H, m), 3.55 (6H, m), 4.78 (1H, m), 6.89 (1H, m), 7.06 (1H, m), 7.37 (1H, m), 8.57 (2H, m) | A1 |
| Int18 | 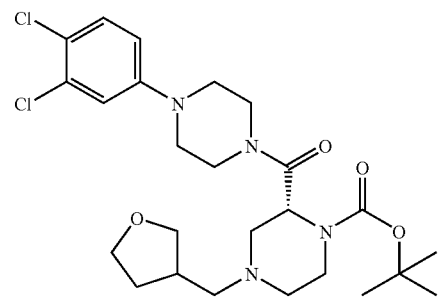 | tert-butyl (2R)-2-{[4-(3,4-dichlorophenyl)piperazin-1-yl]carbonyl}-4-(tetrahydro furan-3-ylmethyl)piperazine-1-carboxylate<br>LCMS M/z(+) 527.33 (M + H)+<br>$^1$H NMR (400.132 MHz, DMSO-$d_6$): 1.40 (10H, m), 1.89 (2H, m), 2.22 (2H, m), 2.36 (1H, m), 2.76 (1H, m), 3.14 (6H, m), 3.42 (1H, m), 3.60 (9H, m), 4.83 (1H, m), 6.97 (1H, m), 7.19 (1H, m), 7.43 (1H, m) | A1 |
| Int19 | 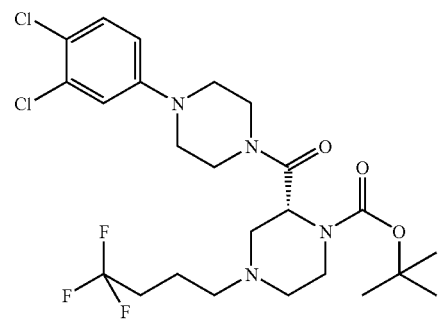 | tert-butyl (2R)-2-{[4-(3,4-dichlorophenyl)piperazin-1-yl]carbonyl}-4-(4,4,4-trifluorobutyl)piperazine-1-carboxylate<br>LCMS M/z(+) 553.29<br>$^1$H NMR (400.132 MHz, DMSO-$d_6$): 1.36 (9H, m), 1.59 (2H, m), 1.97 (1H, m), 2.25 (6H, m), 2.73 (1H, m), 3.17 (5H, m), 3.64 (5H, m), 4.84 (1H, m), 6.97 (1H, m), 7.18 (1H, m), 7.43 (1H, m) | A1 |
| Int20 | 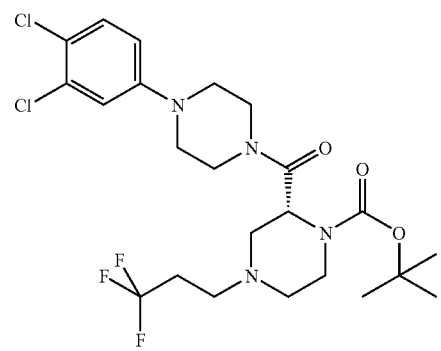 | tert-butyl (2R)-2-{[4-(3,4-dichlorophenyl)piperazin-1-yl]carbonyl}-4-(3,3,3-trifluoropropyl)piperazine-1-carboxylate<br>LCMS M/z(+) 539.37 (M + H)+<br>$^1$H NMR (400.132 MHz, DMSO-$d_6$): 1.35 (9H, m), 1.94 (4H, m), 2.35 (3H, m), 2.99 (5H, m), 3.59 (6H, m), 4.85 (1H, m), 6.98 (1H, m), 7.18 (1H, m), 7.43 (1H, m) | A1 |

| Example No. | Structure | Characterisation Data | Route |
|---|---|---|---|
| Int21 | 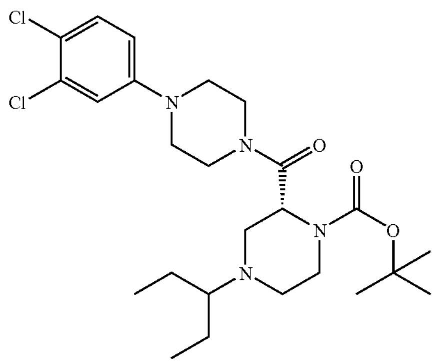 | tert-butyl (2R)-2-{[4-(3,4-dichlorophenyl)piperazin-1-yl]carbonyl}-4-(1-ethylpropyl)piperazine-1-carboxylate<br>LCMS M/z(+) 513.42 (M + H)+<br>$^1$H NMR (300.074 MHz, DMSO-$d_6$): 0.77 (6H, m), 1.13 (1H, m), 1.34 (9H, m), 1.90 (4H, m), 2.13 (1H, m), 2.34 (1H, m), 2.88 (1H, m), 3.13 (6H, m), 3.57 (6H, m), 6.96 (1H, m), 7.16 (1H, m), 7.40 (1H, m) | A1 |
| Int22 | 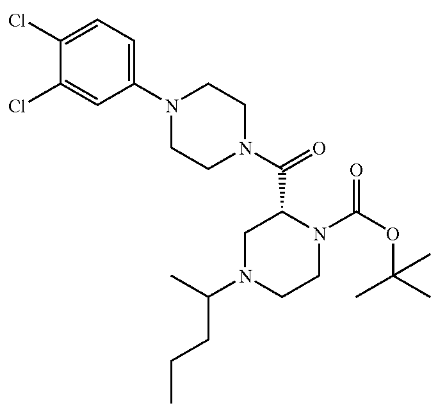 | tert-butyl (2R)-2-{[4-(3,4-dichlorophenyl)piperazin-1-yl]carbonyl}-(1,R,S)-4-(1-methylbutyl)piperazine-1-carboxylate<br>LCMS M/z(+) 513.38 (M + H)+<br>$^1$H NMR (300.074 MHz, DMSO-$d_6$): 0.80 (6H, m), 1.35 (14H, m), 2.31 (2H, m), 2.56 (1H, m), 2.85 (1H, m), 2.99 (5H, m), 3.55 (6H, m), 6.94 (1H, m), 7.15 (1H, m), 7.40 (1H, m) | A1 |
| Int23 | 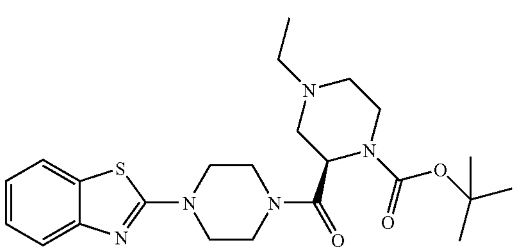 | tert-butyl (2R)-2-{[4-(1,3-benzothiazol-2-yl)piperazin-1-yl]carbonyl}-4-ethyl piperazine-1-carboxylate<br>LCMS M/z(+) 460.33<br>$^1$H NMR (400.132 MHz, DMSO-$d_6$): 0.96 (3H, m), 1.36 (9H, m), 1.85 (1H, m), 2.22 (3H, m), 2.79 (1H, m), 2.97 (2H, m), 3.77 (1H, m), 7.09 (1H, m), 7.29 (1H, m), 7.48 (1H, m), 7.80 (1H, m)<br>(further 8H obscured) | C1 |
| Int24 | 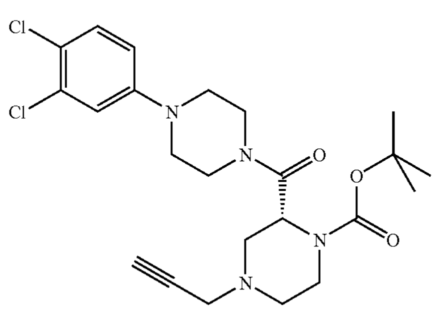 | tert-butyl (2R)-2-{[4-(3,4-dichlorophenyl)piperazin-1-yl]carbonyl}-4-(prop-2-yn-1-yl)piperazine-1-carboxylate<br>LCMS M/z(+)<br>$^1$H NMR (400.132 MHz, DMSO-$d_6$): | C1 |

Table of Intermediates for Examples

| Example No. | Structure | Characterisation Data | Route |
|---|---|---|---|
| Int25 | 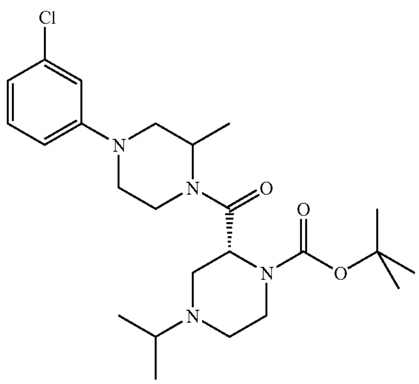 | tert-butyl (2R)-2-{[4-(3-chlorophenyl)-2'-methylpiperazin-1-yl]carbonyl}-4-isopropylpiperazine-1-carboxylate<br>LCMS M/z(+) 465.46 (M + H$^+$)<br>$^1$H NMR (300.074 MHz, DMSO-d$_6$): 0.82 (8H, m), 1.27 (9H, m), 2.03 (1H, m), 2.35 (2H, m), 2.57 (2H, m), 2.86 (2H, m), 3.30 (H, m), 3.51 (1H, m), 3.96 (1H, m), 4.75 (1H, m), 6.77 (3H, m), 7.14 (1H, m) (remaining protons obscured) | C1 |
| Int26 | 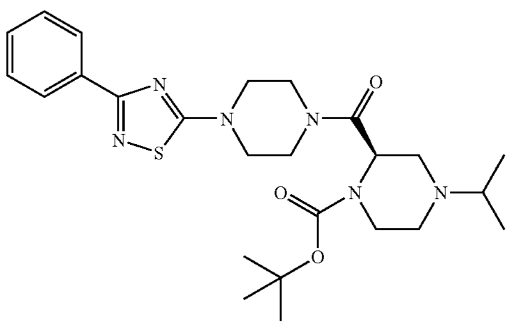 | tert-Butyl (2R)-2-{[4-(4-phenyl-1,2,4-thiadiazol-2-yl)piperazin-1-yl]carbonyl}-4-isopropyl piperazine-1-carboxylate<br>LCMS M/z(+) 501.37 (M + H$^+$)<br>$^1$H-NMR (500.133 MHz, DMSO-d$_6$): 0.95 (6H, t), 1.39 (9H, s), 2.21 (1H, dt), 2.41-2.58 (1H ?, m, obscured), 2.63-2.72 (2H, m), 2.97 (1H, d), 3.49 91h, DT), 3.55-3.76 (9H, m), 4.81 (1H, brt), 7.46 (3H, m), 8.13 (2H, m). | C1 |
| Int27 | 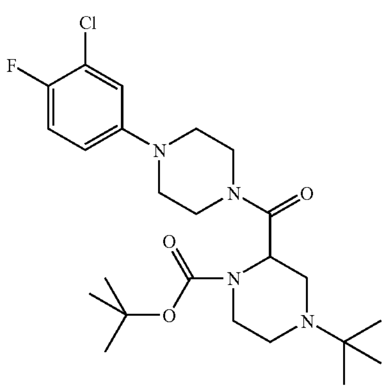 | tert-Butyl (2R, 2S)-2-{[4-(4-fluoro-3-chlorophenyl)piperazin-1-yl]carbonyl}-4-t-butyl piperazine-1-carboxylate<br>LCMS M/z(+) 482.94 (M + H$^+$).<br>$^1$H-NMR (400.130 MHz, CDCl$_3$): 0.88 (1H, m), 1.08 (9H, br), 1.45 (9H, s), 1.5-1.7 (3H, br), 3.11 (4H, br), 3.58 (H, brm), 3.72 (3H, br), 5.85 (1H, br), 6.77 (1H, m), 6.91 (1H, m), 7.05 (1H, t). | C1 |
| Int28 | 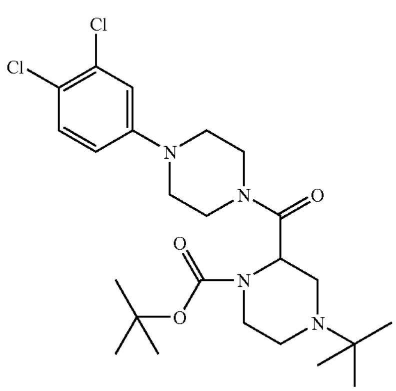 | tert-Butyl (2R, 2S)-2-[4-(3,4-dichlorophenyl)piperazine-1-carbonyl]-4-tert-butyl-piperazine-1-carboxylate<br>LCMS M/z(+) 499 (M + H$^+$). | C1 |

-continued

Table of Intermediates for Examples

| Example No. | Structure | Characterisation Data | Route |
|---|---|---|---|
| Int29 | 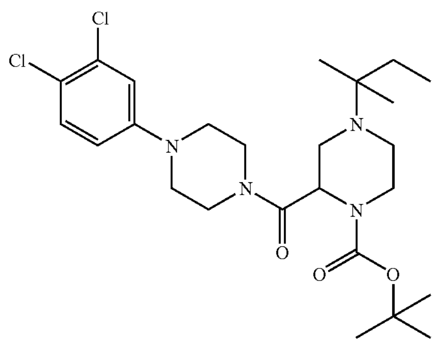 | tert-Butyl (2R, 2S)-2-[4-(3,4-dichlorophenyl)piperazine-1-carbonyl]-4-(2-methylbutan-2-yl)piperazine-1-carboxylate LCMS M/z(+) 513 (M + H⁺). | |
| Int30 | 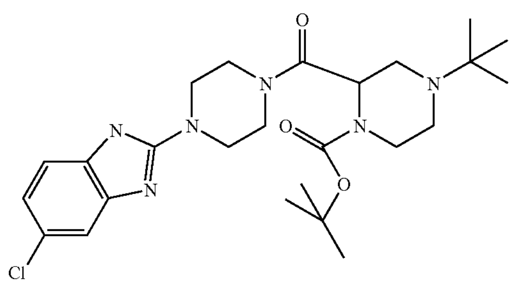 | tert-Butyl (2R, 2S)-2-[4-(5-chloro-1H-benzoimidazol-2-yl)piperazine-1-carbonyl]-4-tert-butyl-piperazine-1-carboxylate LCMS M/z(+) 505, 507 (M + H⁺). | C1 (but EDCI/ HOBT instead of HATU) |
| Int31 | 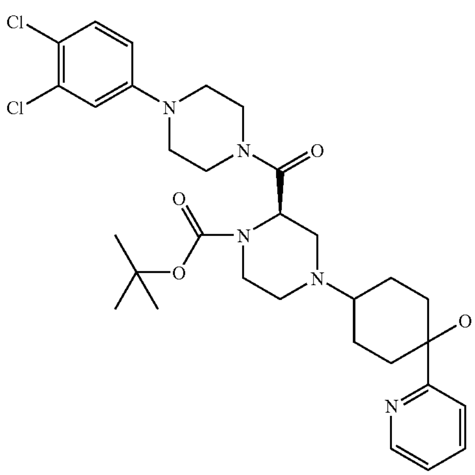 | tert-Butyl (2R)-2-{[4-(3,4-dichlorophenyl)piperazin-1-yl]carbonyl}-4-(4-hydroxy-4-pyridin-2-ylcyclohexyl) piperazine-1-carboxylate LCMS M/z(+) 617.82 (M + H⁺). ¹H NMR (400.132 MHz, DMSOd6) 1.3 (s, 9H), 1.8 (m, 8H), 2.2-3.7 (m, 16H), 4.8 (m, 1H), 6.9 (d, 1H), 7.1 (s, 1H), 7.25 (m, 1H), 7.4 (d, 1H), 7.5 (d, 1H), 7.8 (m, 1H), 8.5 (m, 1H). Faster running isomer | A1 |

The chemical routes used to synthesise the Examples and certain intermediates in their preparation are further illustrated hereinafter.

Route A1

EXPERIMENTAL

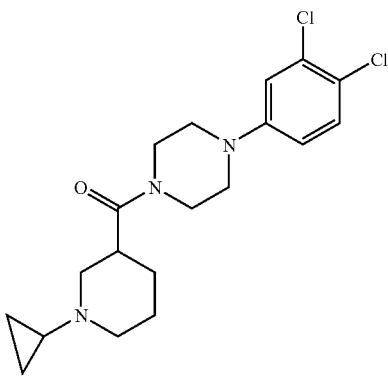

(3R,S)-1-[(1-Cyclopropylpiperidin-3-yl)carbonyl]-4-(3,4-dichlorophenyl)piperazine 1-(3,4-Dichlorophenyl)-4-(piperidin-3-ylcarbonyl)piperazine (0.703 g) was dissolved in methanol (10 ml). Freshly dried 3 Å molecular sieves (0.7 g) were then added, followed by glacial acetic acid (0.41 ml) and 1-ethoxycyclopropoxytrimethylsilane (2.46 ml). To this solution was added 1M sodium cyanoborohydride solution in THF (9.24 ml), the reaction heated to reflux for 2 hours and allowed to cool to room temperature. The resulting suspension was filtered through Celite and washed with 1:1 THF:MeOH solution and filtrate evaporated to dryness to give an off white gum. This was then dissolved in 2M NaOH, extracted twice with DCM and the combined organics dried (Na$_2$SO$_4$), filtered and evaporated to give an off white gum which was purified on Isco™ Companion (40 g column: 10% MeOH/DCM) to give the title compound, as an off white foam (579 mg).

LCMS M/z(+) 383.07 (M+H$^+$)

$^1$H-NMR (CDCl$_3$): 0.33-0.52 (m, 4H), 1.53 (t, 2H), 1.71-1.84 (m, 2H), 2.18 (t, 1H), 2.40 (t, 1H), 2.69-2.78 (m, 1H), 3.00-3.29 (m, 4H), 3.60-3.80 (m, 4H), 6.72 (dd, 1H), 6.95 (d, 1H) and 7.29 (d, 1H).

The 1-(3,4-dichlorophenyl)-4-(piperidin-3-ylcarbonyl)piperazine used to make the above molecule through Route A was prepared using the following procedure.

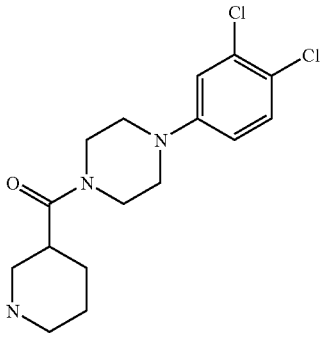

(3R,S)-1-(3,4-Dichlorophenyl)-4-(piperidin-3-ylcarbonyl)piperazine

To a stirred solution of tert-butyl 3-{[4-(3,4-dichlorophenyl)piperazin-1-yl]carbonyl}piperidine-1-carboxylate (1.002 g) in DCM (10 ml) was added TFA (10 ml). The reaction was allowed to stir at ambient temperature for 2 hours. The solvents were removed in vacuo, the residue partitioned between DCM and 2M NaOH, extracted twice and the combined organics dried (Na$_2$SO$_4$), filtered and evaporated to give the product, 1-(3,4-dichlorophenyl)-4-(piperidin-3-ylcarbonyl)piperazine, as a yellow foam (703 mg).

LCMS M/z(+) 343.00 (M+H$^+$)

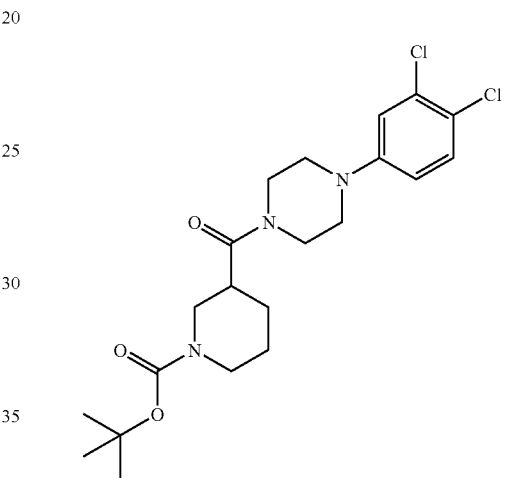

(3R,S)-tert-Butyl 3-{[4-(3,4-dichlorophenyl)piperazin-1-yl]carbonyl}piperidine-1-carboxylate To a stirred solution of N-(3,4-dichlorophenyl)piperazine (1.00 g) in DMF (50 ml) was added N,N-diisopropylethylamine (2.26 ml), 1-(t-butoxycarbonyl)-3-piperidine carboxylic acid (1.091 g) and HATU (1.810 g) and the reaction stirred at ambient temperature for 2 hours. The solvents were then removed under reduced pressure. The resulting gum was partitioned between EtOAc and water, the organic phase washed with saturated sodium bicarbonate solution and evaporated. The resulting gum was purified on Isco™ Companion (40 g column: 50% EtOAc/hexanes) to give the product as an amber gum (2.099 g, contains solvent!).

LCMS M/z(+) 342.38 (M+H$^+$-Boc).

$^1$H-NMR (CDCl$_3$): 1.47 (s, 9H), 1.73 (m, 3H), 1.89 (m, 1H), 2.67 (m, 2H), 2.85 (bs, 1H), 3.16 (m, 4H), 3.75 (bs, 4H), 4.12 (m, 2H), 6.74 (dd, 1H), 6.96 (s, 1H) and 7.29 (d, 1H).

1-(t-Butoxycarbonyl)-3-piperidine carboxylic acid is available commercially and was purchased from Aldrich Chemical Company Inc.

Route A1

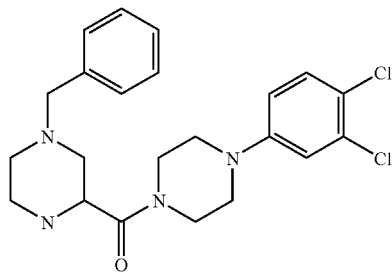

1-Benzyl-3-{[4-(3,4-dichlorophenyl)piperazin-1-yl]carbonyl}piperazine

A mixture of 1-(3,4-dichlorophenyl)-4-(piperazin-2-ylcarbonyl)piperazine dihydrochloride (150 mg), N,N-di-iso-propylethylamine (0.189 mL) and dichloromethane (10 ml) was stirred at room temperature under argon. After 5 minutes benzaldehyde (0.04 ml) was added followed by sodium triacetoxyborohydride (153 mg). The mixture was stirred overnight at room temperature and then filtered through a SCX-2 column eluting with methanol and then a 7M solution $NH_3$ in methanol. The basic fraction was concentrated at reduced pressure. The residue was purified using reverse phase HPLC eluting with a mixture of 5-95% acetonitrile in water and then was filtered through a SCX-2 column eluting with methanol and then a 7M solution $NH_3$ in methanol. The basic fraction was concentrated at reduced pressure. This gave 1-benzyl-3-{[4-(3,4-dichlorophenyl)piperazin-1-yl]carbonyl}piperazine as a colourless gum (125 mg).

LCMS M/z(+) 432.83 (M+H$^+$).

$^1$H NMR (400.132 MHz, CDCl$_3$) 1.95-2.04 (m, 2H), 2.78 (d, 1H), 2.84 (d, 1H), 2.88-3.00 (m, 2H), 3.04-3.16 (m, 4H), 3.46-3.59 (m, 3H), 3.63-3.78 (m, 3H), 3.82 (dd, 1H), 6.69-6.74 (m, 1H), 6.92 (d, 1H), 7.24-7.37 (m, 6H)

Route B

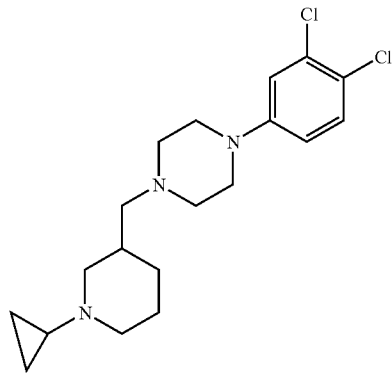

(3R,S)-1-[(1-Cyclopropylpiperidin-3-yl)methyl]-4-(3,4-dichlorophenyl)piperazine

To a stirred solution of (3R,S)-1-[(1-cyclopropylpiperidin-3-yl)carbonyl]-4-(3,4-dichlorophenyl)piperazine (0.555 g) in THF (10 ml) was added a 1M solution of borane in THF (8.71 ml) and the reaction heated to reflux for 4 hours. The cooled reaction mixture was cautiously quenched by addition of methanol and solvents removed in vacuo to give a white solid. To this was added saturated HCl in methanol (20 ml) and the solution heated to reflux for 1 hour. The reaction mixture was evaporated, partitioned between 2M NaOH and DCM, extracted twice, the combined organics dried (Na$_2$SO$_4$), filtered and evaporated to a colorless oil which was purified on Isco™ Companion (12 g column: 7.5% MeOH/DCM) to give the title compound, as a white solid (425 mg).

LCMS M/z(+) 370.38 (M+H$^+$)

$^1$H-NMR (CDCl$_3$): 0.41 (m, 4H), 0.91 (m, 1H), 1.46-1.82 (m, 6H), 2.11 (m, 1H), 2.19 (m, 2H), 2.54 (m, 4H), 2.96 (d, 1H), 3.09 (d, 1H), 3.15 (t, 4H), 6.71 (dd, 1H), 6.94 (d, 1H), and 7.24 (s, 1H).

Route C1

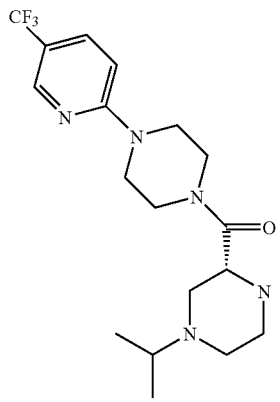

(3R)-1-Isopropyl-3-({4-[5-(trifluoromethyl)pyridin-2-yl]piperazin-1-yl}carbonyl)piperazine 1-[5-(Trifluoromethyl)pyridin-2-yl]piperazine (170 mg) and (2R)-1-(tert-butoxycarbonyl)-4-isopropylpiperazine-2-carboxylic acid (200 mg) were dissolved in dry THF (10 ml) followed by addition of N'N-di-isopropylethylamine (0.15 ml) and O-(7-Azabenzotriazol-1-yl)-N,N,N',N'-Tetramethyl-lUronium Hexafluorophosphate (307 mg) and the reaction was stirred for 4 hours. The solvent was evaporated under reduced pressure, redissolved in DCM (50 ml) and washed with saturated aqueous NaHCO$_3$ (20 ml). The organic layer was separated on a phase separation cartridge and evaporated. Purification by chromatography (3-10% MeOH:DCM) afforded the crude product (231 mg) as a foam which was then dissolved in TFA/DCM (1:1, 10 ml) and stirred for 30 minutes. The solvents were removed under reduced pressure, the residue taken up in 1M aqueous NaOH (30 ml) and extracted with DCM (2×30 ml). The organic layer was separated on a phase separation cartridge and evaporated. Purification by chromatography (5-25% MeOH:DCM) afforded the title compound (100 mg) as a white foam.

LCMS M/z(+) 386 (M+H$^+$).

$^1$H NMR (400.132 MHz, CDCl$_3$) 1.00 (m, 6H), 2.08 (m, 2H,), 2.66 (m, 3H), 2.77 (d, 1H), 2.95 (d, 1H), 3.70 (m, 11H), 6.98 (d, 1H), 7.82 (dd, 1H,), 8.42 (d, 1H).

Other compounds (see Table) were prepared using a similar 2-step procedure starting from the respective (2R)-1-(tert-butoxycarbonyl)-4-alkylpiperazine-2-carboxylic acid and the corresponding aryl piperazine. (Where the aryl piperazine used was a salt, an extra equivalent of N'N-di-isopropylethylamine was used to keep the reaction basic). 5-Chloro-2-piperazin-1-yl-1H-benzimidazole trifluoroacete salt was prepared as described later below by a variation on Route A2 but applied to the preparation of these intermediates.

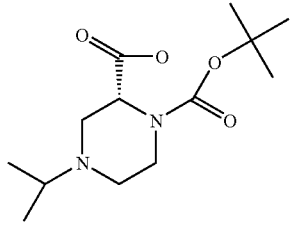

(2R)-1-(tert-Butoxycarbonyl)-4-isopropylpiperazine-2-carboxylic Acid

To (2R)-1-(tert-butoxycarbonyl)piperazine-2-carboxylic acid (4.5 g) and Na₂CO₃ (8.32 g) was added dry EtOH (135 ml) and isopropyl iodide (2.16 ml) and the mixture heated at reflux for 18 hours under argon. The solvent was then removed under reduced pressure, 5% MeOH/DCM (50 ml) added, the mixture stirred for 1 hour in a stoppered flask, filtered and washed through with DCM (2×10 ml). The filtrate was applied directly to a 120 g-silica Redisep® cartridge and purified using 10-70% MeOH/DCM. After evaporation, the product was isolated as a white foam (4.50 g), which was used without further purification.

$^1$H NMR (400.132 MHz, DMSO) 0.95 (m, 6H), 1.40 (2×s, 9H), 2.30 (m, 2H), 2.75 (m, 2H), 2.95 (t, 1H), 3.12 (t, 1H,), 3.70 (m, 1H), 4.48 (d, 1H), 12.60 (br. s, 1H).

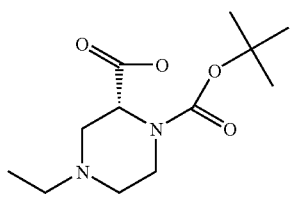

(2R)-1-(tert-Butoxycarbonyl)-4-ethylpiperazine-2-carboxylic Acid

In a similar manner to the above, (2R)-1-(tert-butoxycarbonyl)piperazine-2-carboxylic acid (1.406 g) gave the title compound as a white foam (1.00 g), which was used without further purification.

$^1$H NMR (400.132 MHz, DMSO) 0.95 (3H, t), 1.35+1.42 (2×s (rotameric), 9H), 1.81 (m, 1H), 2.03 (m, 1H), 2.29 (m, 2H), 2.78 (m, 1H), 3.02+3.16 (2×t, rotameric 1H,), 3.28 (m, 1H), 3.63 (appt. d, 1H,), 4.35+4.42 (2× appt. s., rotameric, 1H,), 13.00 (br. s, 1H)

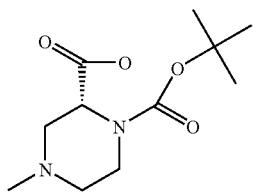

(2R)-1-(tert-Butoxycarbonyl)-4-methylpiperazine-2-carboxylic Acid

In a similar manner to the above, (2R)-1-(tert-butoxycarbonyl)piperazine-2-carboxylic acid (0.46 g) gave the title compound as a white foam (1.00 g), which was used without further purification.

LCMS M/z(−) 243.32 (M−H⁻).

$^1$H-NMR (DMSO-d₆): 1.43 (9H, 2×s), 1.83 (1H, dt), 2.07 (1H, m), 2.16 (3H, s), 2.70 (1H, t), 3.01 (1H, t), 3.16 (2H, obscured), 3.65 (1H, d), 4.41 (1H, d)

The (2R)-1-(tert-butoxycarbonyl)piperazine-2-carboxylic acid was purchased from Ennova MedChem Group Inc., New Jersey, USA.

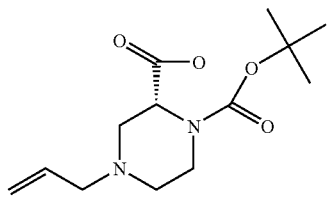

(2R)-1-(tert-Butoxycarbonyl)-4-(prop-2-en-1-yl) piperazine-2-carboxylic Acid

In a similar manner to the above, (2R)-1-(tert-butoxycarbonyl)piperazine-2-carboxylic acid (0.92 g) gave the title compound as a white foam (1.08 g), which was used without further purification.

LCMS M/z(−) 269.38 (M−H⁻).

$^1$H-NMR (DMSO-d₆): 1.34, 1.38 (9H, 2×s), 1.83 (1H, dt), 1.97 (1H, m), 2.71 (1H, brt), 2.88 (2H, m), 3.05, 3.22, 3.31 (2H, rotamers, obscured), 3.62 (1H, d), 4.28 (1H, brd), 5.11 (1H, dd), 5.17 (1H, dd), 5.73 (1H, m).

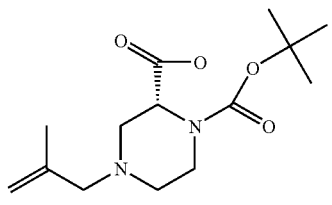

(2R)-1-(tert-Butoxycarbonyl)-4-(2-methylprop-2-en-1-yl)piperazine-2-carboxylic Acid In a similar manner to the above, (2R)-1-(tert-butoxycarbonyl)piperazine-2-carboxylic acid (0.92 g) gave the title compound as a grey foam (0.91 g), which was used without further purification.

LCMS M/z(−) 283.39 (M−H⁻).

$^1$H-NMR (DMSO-d₆): 1.38, 1.42 (9H, 2×s), 1.66 (3H, s), 1.95 (2H, m), 2.72 (2H, m), 2.93 (1H, dd), 3.03 (1H, dt), 3.2 (obscured), 3.67 (1H, d), 4.43 (1H, d), 4.85 (2H, d).

The Following Aryl Piperazine Intermediate was not Available Commercially and was Synthesised by a Variation of Route D

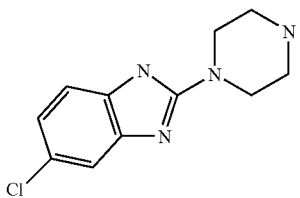

5-Chloro-2-piperazin-1-yl-1H-benzimidazole Trifluoroacete Salt

TFA (2 mL) was added to a solution of tert-butyl 4-(5-chloro-1H-benzimidazol-2-yl)piperazine-1-carboxylate (72 mg) in DCM (2 mL) and the reaction was stirred for 1 h. The solvent was then evaporated under high vacuum for 1 h to afford the title compound as a gum which was used without further analysis.

LCMS M/z(+) 237, 239 (M+H$^+$).

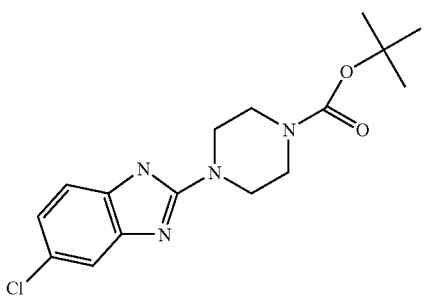

tert-Butyl 4-(5-chloro-1H-benzimidazol-2-yl)piperazine-1-carboxylate

To 2,5-dichloro-1H-benzimidazole (100 mg, Synth. Commun, 1998, 28, 9, 1703-12) and Boc-piperazine (150 mg) was added dry EtOH (5 mL) and then triethylamine (0.112 mL) and the reaction was heated in a microwave at 150° C. for 1 h. The reaction was then heated further for 2.5 h at 170° C. The solvent was then evaporated in vacuo and the residue purified by column chromatography 30-100% EtOAC:hexanes to afford the title compound (72 mg) as a colourless oil.

LCMS M/z(+) 337, 339 (M+H$^+$).

$^1$H NMR (400.132 MHz, CDCl$_3$) 1.48 (s, 9H), 3.52 (brs, 8H), 7.02 (d, 1H), 7.18 (d, 1H), 7.27 (s, 1H).

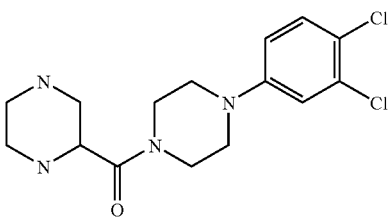

Deprotection Following Route C1, See Below (2R,S)-1-(3,4-dichlorophenyl)-4-(piperazin-2-ylcarbonyl)piperazine A solution of (2R,S)-di-tert-butyl 2-{[4-(3,4-dichlorophenyl)piperazin-1-yl]carbonyl}piperazine-1,4-dicarboxylate (300 mg) in dichloromethane (10 ml) was stirred at room temperature. A 4M solution HCl in dioxane (5 ml) was added and the mixture was stirred overnight. The mixture was concentrated at reduced pressure and the residue dissolved in methanol and filtered through a SCX-2 column eluting with methanol and then a 7M solution NH$_3$ in methanol. The basic fraction was concentrated at reduced pressure. This gave the title compound as a white gum (190 mg).

LCMS M/z(+) 342.87 (M+H$^+$).

$^1$H NMR (400.132 MHz, DMSO) 2.39-2.49 (m, 2H), 2.54-2.71 (m, 3H), 2.76-2.88 (m, 2H), 3.49-3.76 (m, 5H), 3.10-3.38 (m, 5H), 6.96 (dd, 1H), 7.16 (d, 1H), 7.41 (d, 1H).

The di-tert-butyl 2-{[4-(3,4-dichlorophenyl)piperazin-1-yl]carbonyl}piperazine-1,4-dicarboxylate used to make the above molecule was prepared using the following procedure.

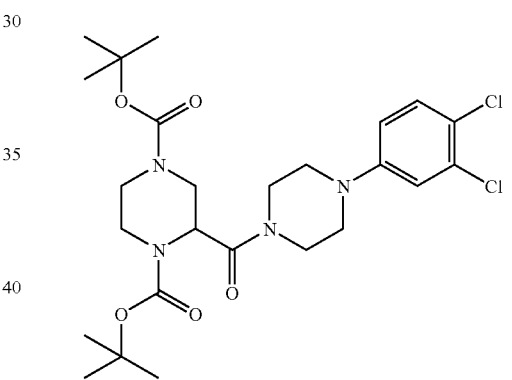

(2R,S)-Di-tert-butyl 2-{[4-(3,4-dichlorophenyl)piperazin-1-yl]carbonyl}piperazine-1,4-dicarboxylate A solution of 1-(3,4-dichlorophenyl)piperazine (3.0 g), 1,4-bis(tert-butoxycarbonyl)piperazine-2-carboxylic acid (available from Arch Corporation (Ennova MedChem Group, Inc.), 4.3 g) and N,N-di-iso-propylethylamine (4.5 ml) in N,N-dimethylformamide (200 ml) was stirred at room temperature. O-(7-Azabenzotriazol-1-yl)-N,N',N'-TetramethylUronium Hexafluorophosphate (5.4 g) was added and the mixture was stirred overnight. The mixture was partitioned between ethyl acetate and brine. The organic layer was washed three times with brine, dried (MgSO$_4$), filtered and concentrated at reduced pressure. The residue was purified by recrystallisation from ethyl acetate (120 ml). This gave di-tert-butyl 2-{[4-(3,4-dichlorophenyl)piperazin-1-yl]carbonyl}piperazine-1,4-dicarboxylate as a white solid (5.37 g).

LCMS M/z(+) 542.85 (M+H$^+$).

tert-Butyl (2R)-4-cyclopropyl-2-{[4-(3,4-dichlorophenyl)piperazin-1-yl]carbonyl}piperazine-1-carboxylate used to make (3R)-1-cyclopropyl-3-{[4-(3,4-dichlorophenyl)piperazin-1-yl]carbonyl}piperazine was made by the following procedure:

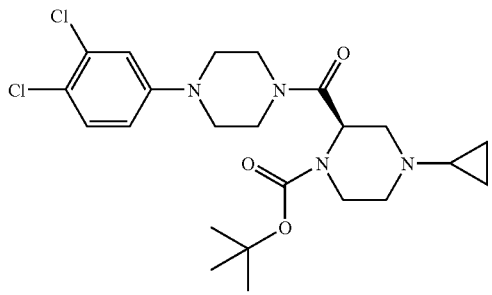

tert-Butyl (2R)-4-cyclopropyl-2-{[4-(3,4-dichlorophenyl)piperazin-1-yl]carbonyl}piperazine-1-carboxylate Using Route A1 and tert-butyl (2R)-2-{[4-(3,4-dichlorophenyl)piperazin-1-yl]carbonyl}piperazine-1-carboxylate (195 mg) gave, after chromatographic purification on SiO₂, eluting with 0-20% MeOH/CH₂Cl₂, the title intermediate (55 mg).
LCMS M/z(+) 483.36 (M+H⁺)
¹H NMR (399.902 MHz, DMSO): 0.19 (1H, m), 0.32 (1H, m), 0.41 (2H, m), 1.37 (9H, m), 1.66 (1H, m), 2.56 (1H, m), 2.82 (1H, m), 3.04 (1H, m), 3.21 (4H, m), 3.45 (1H, m), 3.59 (6H, m), 4.76 (1H, m), 6.92 (1H, m), 7.10 (1H, m), 7.38 (1H, d)

Mono-Deprotection Route to Intermediate for eg Route A

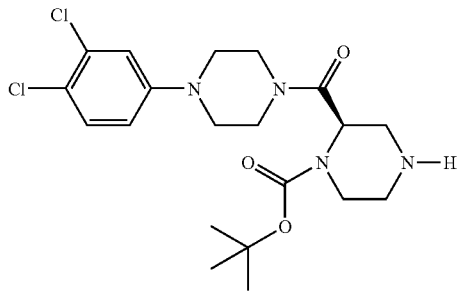

tert-Butyl (2R)-2-{[4-(3,4-dichlorophenyl)piperazin-1-yl]carbonyl}piperazine-1-carboxylate To a solution of di-tert-butyl (2R)-2-{[4-(3,4-dichlorophenyl)piperazin-1-yl]carbonyl}piperazine-1,4-dicarboxylate and 2,6-lutidine in dichloromethane at ice bath temperature under argon was added TBDMSOTf (total of 0.4 mL added following the reaction by tlc and lc-ms until complete. The ice-bath was removed and the reaction quenched with saturated aqueous ammonium chloride at ambient temperature. The mixture was partitioned between water and dichloromethane and the organic layer washed with brine and concentrated at reduced pressure. The residue was dissolved in THF and cooled to ice bath temperature. Water (0.5 mL) was added, followed by TBAF (1M in THF) drop-wise. The mixture was again warmed to ambient temperature and partitioned between dichloromethane and water. The organic phase was dried (MgSO₄), filtered and concentrated. The residue (647 mg) was purified by silica gel chromatography on an Isco Companion (40 g column), eluting with 0-10% methanol in dichloromethane to give the title intermediate (204 mg). A further amount of impure compound (48 mg) was also isolated.
LCMS M/z(+) Mass ion not seen
¹H NMR (399.902 MHz, DMSO): 1.40 (9H, s), 2.51 (1H, m), 2.91 (2H, m), 3.09 (1H, m), 3.28 (5H, m), 3.62 (5H, m), 4.71 (1H, m), 6.91 (1H, m), 7.11 (1H, s), 7.37 (1H, m) (1H obscured).

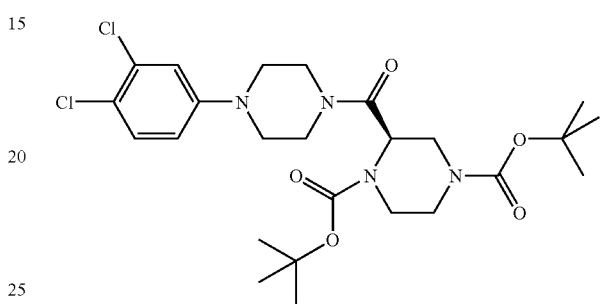

Di-tert-butyl (2R)-2-{[4-(3,4-dichlorophenyl)piperazin-1-yl]carbonyl}piperazine-1,4-dicarboxylate The di-tert-butyl (2R)-2-{[4-(3,4-dichlorophenyl)piperazin-1-yl]carbonyl}piperazine-1,4-dicarboxylate used to prepare tert-butyl (2R)-2-{[4-(3,4-dichlorophenyl)piperazin-1-yl]carbonyl}piperazine-1-carboxylate was prepared from (2R)-piperazine-2-carboxylic acid (500 mg) via the di-t-BOC derivative using route C1 as for the racemic material (see the precursors described for Example 32). This gave the title intermediate (499 mg).
¹H NMR (400.132 MHz, DMSO): 1.36 (19H, m), 2.97 (5H, m), 3.67 (7H, m), 4.07 (1H, m), 4.88 (1H, m), 6.98 (1H, m), 7.23 (1H, s), 7.43 (1H, d)
LCMS M/z(+) Mass ion not seen
(2R)-piperazine-2-carboxylic acid is available from 3b Medical Systems Inc.

1-[(1-Ethylpiperidin-3-yl)carbonyl]-4-[3-(trifluoromethyl)phenyl]piperazine used to make 1-[(1-ethylpiperidin-3-yl)methyl]-4-[3-(trifluoromethyl)phenyl]piperazine was made via the following procedures (starting with Route A2).

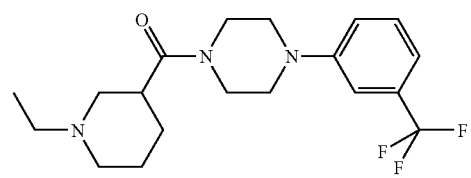

1-[(1-Ethylpiperidin-3-yl)carbonyl]-4-[3-(trifluoromethyl)phenyl]piperazine

A mixture of 1-(piperidin-3-ylcarbonyl)-4-[3-(trifluoromethyl)phenyl]piperazine hydrochloride (600 mg) in N,N- dimethylformamide (10 ml) was stirred at room temperature. Potassium carbonate (800 mg) was added followed by ethyl bromide (158 mg) and the mixture was stirred overnight. The mixture was filtered through a sinter and then through a SCX-2 column eluting with methanol and then a 7M solution NH$_3$ in methanol. The basic fraction was concentrated at reduced pressure. This gave 1-[(1-ethylpiperidin-3-yl)carbonyl]-4-[3-(trifluoromethyl)phenyl]piperazine as a colourless oil (420 mg).

LCMS M/z(+) 369.91 (M+H$^+$).

$^1$H NMR (400.132 MHz, CDCl$_3$) 1.09 (t, 3H), 1.47-1.86 (m, 4H), 1.92 (dt, 1H), 2.17 (t, 1H), 2.45 (sextet, 2H), 2.83 (tt, 1H), 2.92-2.99 (m, 2H), 3.21 (bs, 4H), 3.74 (d, 4H), 7.04-7.08 (m, 1H), 7.10-7.15 (m, 2H), 7.37 (t, 1H)

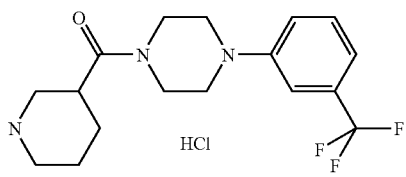

1-(Piperidin-3-ylcarbonyl)-4-[3-(trifluoromethyl) phenyl]piperazine Hydrochloride A solution of tert-butyl 3-({4-[3-(trifluoromethyl)phenyl] piperazin-1-yl}carbonyl)piperidine-1-carboxylate (1.5 g) in dichloromethane (10 ml) was stirred at room temperature. A 4M solution HCl in dioxane (20 ml) was added and the mixture was stirred for 30 minutes. The mixture was filtered and washed with dichloromethane and then diethyl ether. This gave 1-(piperidin-3-ylcarbonyl)-4-[3-(trifluoromethyl) phenyl]piperazine hydrochloride
as a white solid (1.3 g).

LCMS M/z(+) 341.97 (M+H$^+$).

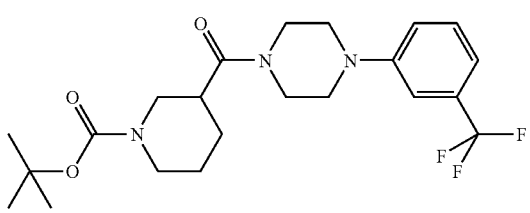

tert-Butyl 3-({4-[3-(trifluoromethyl)phenyl]piperazin-1-yl}carbonyl)piperidine-1-carboxylate A solution of 1-(3,4-dichlorophenyl)piperazine (1 g) (available from Aldrich Chemical Company, Inc.), 1-(tert-butoxycarbonyl)piperidine-3-carboxylic acid (909 mg) (available from Aldrich Chemical Company, Inc.) and N,N-di-iso-propylethylamine (1.38 ml) in N,N-dimethylformamide (25 ml) was stirred at room temperature. O-(7-Azabenzotriazol-1-yl)-N,N,N',N'-TetramethylUronium Hexafluorophosphate (1.66 g) was added and the mixture was stirred overnight. The mixture was partitioned between ethyl acetate and water. The organic layer was washed three times with water and then once with brine, dried (MgSO$_4$), filtered and concentrated at reduced pressure. The residue was purified by silica chromatography on the Isco™ Companion (0-50% ethyl acetate in hexane). This gave tert-butyl 3-({4-[3-(trifluoromethyl)phenyl]piperazin-1-yl}carbonyl)piperidine-1-carboxylate as a light yellow oil (1.74 g).

LCMS M/z(+) 385.73 (M-$^t$Bu+H$^+$).

Route D

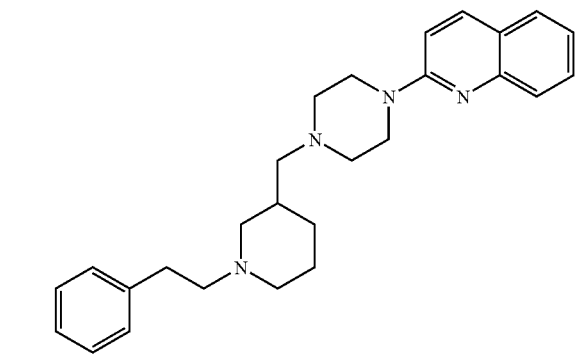

(3R,S)-1-({1-[2-phenyl]ethyl}piperidin-3-ylmethyl)-4-(2-quinolinyl)piperazine

1-{[(3R,S)-1-Phenylethylpiperidin-3-yl]methyl}piperazine (60 mg), 2-chloroquinoline (38 mg), methanol (5 ml) and concentrated hydrochloric acid (5 drops from a glass pipette) were sealed in a microwave vessel and microwaved at 200° C. for 60 minutes. The solvent was removed in vacuo and the residue partitioned between saturated aqueous sodium bicarbonate (20 ml) and ethyl acetate (2×35 ml). The combined organic extracts were concentrated in vacuo and adsorbed onto silica for purification by chromatography eluting with 0-7.5% methanol/dichloromethane. This gave the title compound as a white solid (9 mg).

LCMS M/z(+) 415.34 (M+H$^+$).

$^1$H NMR (400.132 MHz, DMSO) 1.9 (m, 5H), 2.4-3.4 (m, 14H), 3.7 (m, 4H), 7.2 (m, 7H), 7.5 (m, 2H), 7.7 (d, 1H), 8.0 (d, 1H).

Other compounds (see table of Examples hereinbefore) were prepared using a similar procedure starting from the corresponding 1-(piperidin-3-ylmethyl)piperazine.

For example, 1-{[(3R)-1-({2-phenyl}ethylpiperidin-3-yl] methyl}piperazine used to make the (3R)-enantiomer of the above molecule through Route D was prepared using the following procedure.

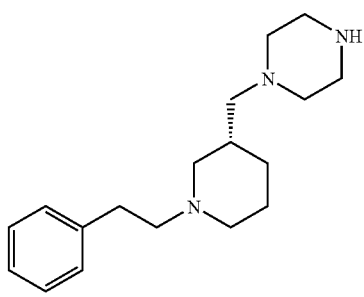

1-{[(3R)-1-({2-Phenyl}ethyl)piperidin-3-yl] methyl}piperazine

Water (5 ml), 10% palladium on carbon (900 mg) and ethanol (50 ml) were added to benzyl 4-{[(3R)-1-(2-phenyl)ethylpiperidin-3-yl]methyl}piperazine-1-carboxylate (950 mg) under an argon atmosphere. The mixture was stirred overnight under a hydrogen filled balloon. The catalyst was remove by filtration through celite and the filtrate concentrated in vacuo and azeotroped once with toluene to give the title intermediate as a yellow oil (650 mg).

$^1$H-NMR (400.132 MHz, DMSO-$d_6$) 1.4 (5H, m), 2.0 to 4.0 (18H, m), 7.2 (5H, m).

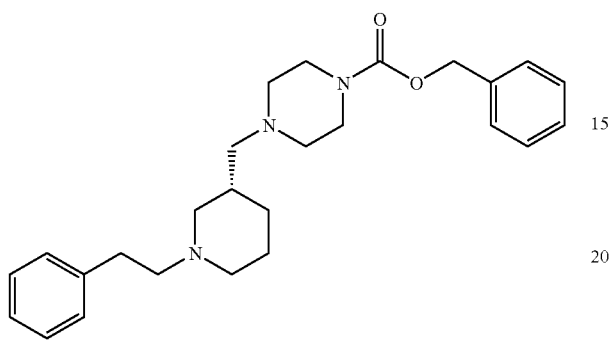

Benzyl 4-{[(3R)-1-(2-phenyl)ethylpiperidin-3-yl]methyl}piperazine-1-carboxylate

Benzyl 4-[(3R)-piperidin-3-ylmethyl]piperazine-1-carboxylate dihydrochloride (1.5 g) was suspended in THF (45 ml) and stirred at room temperature. Di-isopropylethylamine (3.3 ml) was added, followed by phenylacetaldehyde (0.9 ml) and magnesium sulphate (300 mg). After 20 minutes, sodium triacetoxyborohydride (1.6 g) was added and stirring continued overnight. Inorganic residues were removed by filtration and the filtrate was adsorbed onto silica for purification by chromatography eluting with 0-7% methanol/dichloromethane. This gave the title intermediate as a pale yellow gum (960 mg).

LCMS M/z(+) 422.02 (M+H$^+$).

$^1$H-NMR (400.132 MHz, DMSO-$d_6$) 1.1 (1H, m), 2.3 (7H, m), 2.5 to 3.5 (11H, m), 5.05 (2H, s), 7.3 (100H, m).

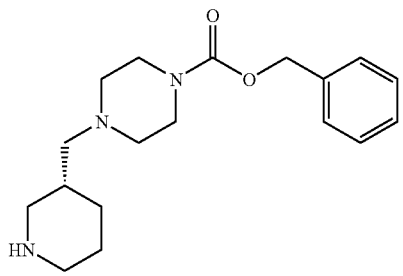

Benzyl 4-[(3R)-piperidin-3-ylmethyl]piperazine-1-carboxylate

Benzyl 4-{[(3S)-1-(tert-butoxycarbonyl)piperidin-3-yl]methyl}piperazine-1-carboxylate (4.46 g) was stirred in a mixture of trifluoroacetic acid (20 ml) and dichloromethane (200 ml) for two hours at room temperature. The reaction mixture was concentrated in vacuo and the resulting oil separated between ethyl acetate (200 ml) and saturated aqueous sodium bicarbonate solution (500 ml). The ethyl acetate layer was separated, dried over magnesium sulphate, filtered then concentrated in vacuo to give the title compound (3.6 g).

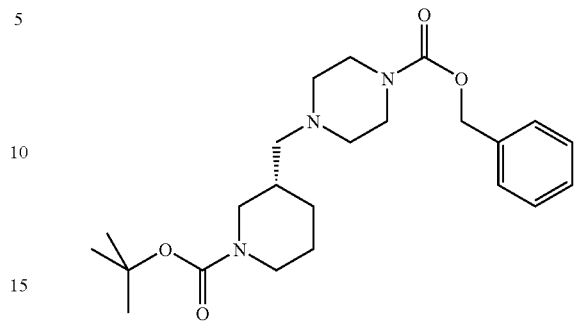

Benzyl 4-{[(3S)-1-(tert-butoxycarbonyl)piperidin-3-yl]methyl}piperazine-1-carboxylate tert-Butyl (3R)-3-(hydroxymethyl)piperidine-1-carboxylate (2.31 g) and Dess-Martin periodinane (5.0 g) were stirred in dichloromethane (30 ml) for 2 hours at room temperature. 2N aqueous sodium hydroxide (100 ml) was added and the mixture stirred for 10 minutes. The dichloromethane layer was separated, dried over magnesium sulphate then filtered. This solution of tert-butyl (3R)-3-formylpiperidine-1-carboxylate was added to a solution of benzyl piperazine-1-carboxylate (2.36 g) in dichloromethane (70 ml). Sodium triacetoxyborohydride (5.67 g) was added and the reaction left to stir at room temperature for 18 hours. Saturated aqueous sodium bicarbonate solution (500 ml). The dichloromethane layer was separated, dried over magnesium sulphate, filtered then concentrated in vacuo to give the title compound (4.46 g).

LCMS M/z(+) 418.33 (M+H$^+$).

The tert-Butyl (3R)-3-(hydroxymethyl)piperidine-1-carboxylate used in the above procedure was commercially available and purchased from Arch Chemical Corporation, New Jersey, The 1-{[(3R)-1-cyclopropylpiperidin-3-yl]methyl}piperazine used in Route D was prepared using the following procedure.

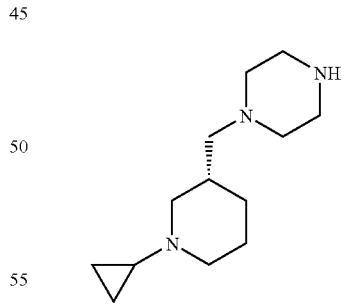

1-{[(3R)-1-Cyclopropylpiperidin-3-yl]methyl}piperazine

Benzyl 4-{[(3R)-1-cyclopropylpiperidin-3-yl]methyl}piperazine-1-carboxylate (45 mg) was dissolved in ethanol (6 ml). 10% Palladium on carbon (Degussa) (72 mg) was added and the mixture stirred for 60 hours at room temperature under an atmosphere of hydrogen. A further amount of catalyst (60 mg) was added and the mixture stirred for 40 hours at room temperature under an atmosphere of hydrogen. The reaction mixture was filtered through a pad of Celite, washed with ethanol and the filtrate concentrated in vacuo to give the title compound as a white solid (27.5 mg).

LCMS M/z(+) 224.41 (M+H$^+$).

$^1$H-NMR (400.132 MHz, CDCl$_3$) 0.45 (4H, m), 0.9 (1H obscured, m), 1.45-1.58 (2H, m), 1.68 (1H, m), 1.74-1.85 (3H, m), 2.07-2.55 (10H, m), 2.89 (2H, m), 2.99 (1H, d), 3.09 (1H,

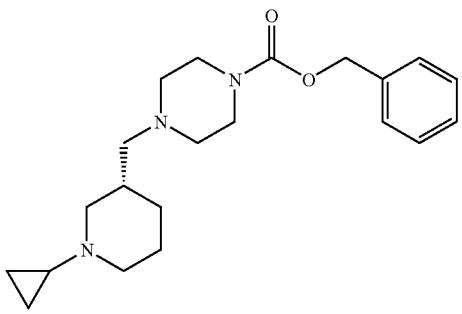

Benzyl 4-{[(3R)-1-cyclopropylpiperidin-3-yl]methyl}piperazine-1-carboxylate

Benzyl 4-[(3R)-piperidin-3-ylmethyl]piperazine-1-carboxylate dihydrochloride (389 mg) was dissolved in MeOH (5 mL) and di-isopropylethylamine (0.52 mL) added under argon. Freshly dried 3 Å molecular sieves (413 mg) were added, followed sequentially by glacial acetic acid (0.2 mL), 1-ethoxy-1-trimethylsilyloxycyclopropane (1.2 mL) and sodium cyanoborohydride as a 1M solution in THF (4.5 mL). The mixture was heated at 81° C. for 2 hours, allowed to cool, filtered through Celite, washed through with 1:1 MeOH-THF (10 mL) and evaporated. The residue was partitioned between ethyl acetate and 1M aqueous sodium hydroxide solution, the organic extract washed with brine, dried over MgSO$_4$ and evaporated. The residue was purified by silica column chromatography, eluting with a gradient of 0 to 10% MeOH in dichloromethane to give the title compound as a white solid (222 mg, 62%).

LCMS M/z(+) 358.41 (M+H$^+$).

$^1$H-NMR (400.132 MHz, CDCl$_3$) 0.46 (4H, m), 0.9-1.1 (1H obscured, m), 1.5-1.7 (4H, m), 1.7-1.8 (3H, m), 2.14 (2H, d), 2.23-2.43 (4H, m), 3.02 (1H, d), 3.12 (1H, d), 3.50 (4H, m), 5.13 (2H, s), 7.28-7.38 (5H, m).

Route C1

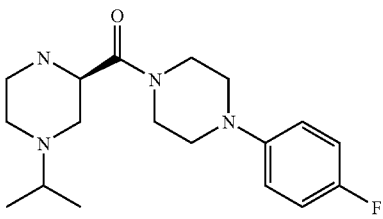

(3R)-3-{[4-(4-Fluorophenyl)piperazin-1-yl]carbonyl}-1-isopropylpiperazine

To a stirred solution of (2R)-1-(tert-butoxycarbonyl)-4-isopropylpiperazine-2-carboxylic acid (0.078 g, 0.29 mmol, 50% strength by NMR), 1-(4-fluorophenyl)-piperazine (0.031 g, 0.174 mmol), HOBT (0.024 g, 0.174 mmol) and DIPEA (0.091 ml, 0.52 mmol) in DMF (2 ml) was added EDCI (0.033 g, 0.174 mmol) and the reaction allowed to stir at room temperature over weekend. The solvents were then removed in vacuo and the residue partitioned between DCM/water, extracted twice with DCM, the organics passed through phase separating cartridge and concentrated under reduced pressure to give a colourless gum. This was then purified by prep HPLC (basic, high throughput machine) to give a white solid. This was then dissolved in DCM (2 ml), TFA (2 ml) added and reaction allowed to stir overnight at room temperature. The solvents were then removed under reduced pressure to give a brown gum. This was partitioned between DCM and 2M NaOH, extracted twice with DCM, the combined organics passed through a phase separating cartridge and concentrated in vacuo to give the title compound, as a yellow gum (12 mg, 0.036 mmol, 12% over 2 steps).

LCMS M/z(+) 335.44 (M+H$^+$).

Other compounds (see Table) were prepared using a similar 2-step procedure starting from the corresponding, commercially available aryl piperazine.

Chiral Separation for Example 87

| Instrument | Gilson Prep (200 ml heads) |
|---|---|
| Column | Merck 50 mm 20 µm Chiralpak AD - No AD00SC A1003 Packed 28-08-03 |
| Eluent | MeCN/MeOH 90/10 |
| Flow | 60 ml/min |
| Wavelength | 250.225 nm |
| Sample Conc | 11 mg/ml (mobile phase) |
| Injection volume | 12 ml (134 mg) |
| Pressure | 28 bar |
| Run Time | 30 min |

Chiral Separation for Example 90

Chiral AD Column Using 10% Methanol in Acetonitrile

As with other N-alkyl-piperazine amides (see Table), Examples 87 and 90 were prepared in a similar 2-step procedure from the respective 1-(tert-butoxycarbonyl-4-alkyl-piperazine-2-carboxylic acids and 1-(3,4-dichlorophenyl)piperazine

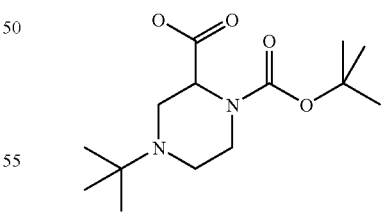

1-(tert-Butoxycarbonyl)-4-tert-butylpiperazine-2-carboxylic Acid

The title compound was synthesised from 1-(tert-butoxycarbonyl)-4-tert-butylpiperazine as described in our published patent application WO-2006/067401. The preparation of the latter in 3 steps from the commercially available 1-benzylpiperazine is also described therein.

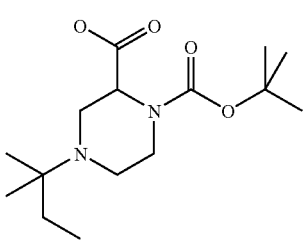

1-(tert-Butoxycarbonyl)-4-(2-methylbutan-2-yl)piperazine-2-carboxylic Acid

The title compound was synthesised from 1-(tert-butoxycarbonyl)-4-(2-methylbutan-2-yl)piperazine in a similar manner to that described for the above compound in our published patent application WO-2006/067401.

The preparation of 1-(tert-butoxycarbonyl)-4-(2-methylbutan-2-yl)piperazine is described in *J. Med. Chem.*, 2004. 47 (11), 2833-2838.

Example 94

4-((3R)-3-{[4-(3,4-dichlorophenyl)piperazin-1-yl]carbonyl}piperazin-1-yl)-1-pyridin-2-ylcyclohexanol

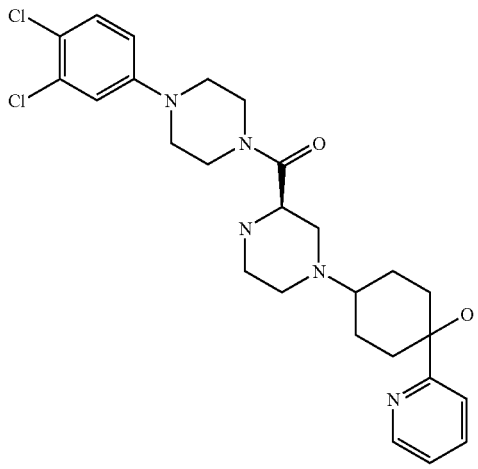

The faster running isomer of tert-butyl (2R)-2-{[4-(3,4-dichlorophenyl)piperazin-1-yl]carbonyl}-4-(4-hydroxy-4-pyridin-2-ylcyclohexyl)piperazine-1-carboxylate (45 mg) was dissolved in dichloromethane (6 ml). Trifluoroacetic acid (1 ml) was added and the solution stirred at room temperature for 2 hours and allowed to stand over the weekend. The mixture was partitioned between saturated aqueous sodium bicarbonate (10 ml) and dichloromethane (2×100 ml) and combined organics were concentrated in vacuo and adsorbed onto silica for purification by chromatography eluting with 0-15% methanol/dichloromethane. This gave one isomer of 4-((3R)-3-{[4-(3,4-dichlorophenyl)piperazin-1-yl]carbonyl}piperazin-1-yl)-1-pyridin-2-ylcyclohexanol as a light brown solid (31%, 85%).

LCMS M/z(+) 517.83 (M+H⁺).

¹H NMR (400.132 MHz, DMSO-d₆) 1.4 (m, 2H), 1.6 (m, 2H), 1.8 (m, 4H), 2.2 (m, 1H), 2.35 (t, 2H), 2.7 (m, 2H), 2.9 (t, 2H), 3.2 (m, 6H), 3.6 (m, 4H), 4.95 (s, 1H), 6.9 (d, 1H), 7.1 (s, 1H), 7.2 (m, 1H), 7.4 (d, 1H), 7.6 (d, 1H), 7.75 t, 1H), 8.5 (d, 1H).

The preparation of 4-hydroxy-4-pyridin-2-ylcyclohexanone

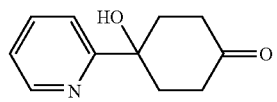

used for the synthesis of Example 94 is described in WO2004050024 (Incyte).

Intermediate 31 tert-butyl (2R)-2-{[4-(3,4-dichlorophenyl)piperazin-1-yl]carbonyl}-4-(4-hydroxy-4-pyridin-2-ylcyclohexyl)piperazine-1-carboxylate

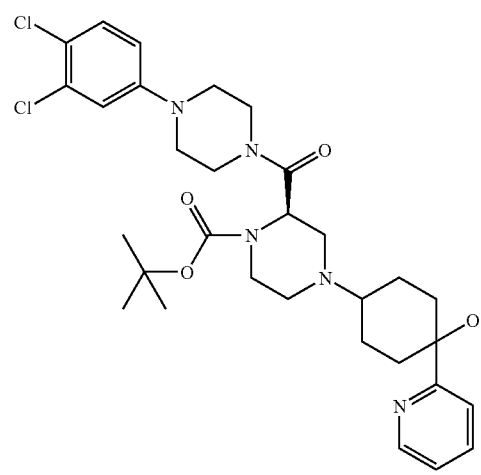

tert-Butyl (2R)-2-{[4-(3,4-dichlorophenyl)piperazin-1-yl]carbonyl}piperazine-1-carboxylate (278 mg) was dissolved in THF (25 ml) and stirred at room temperature. DIPEA (0.32 ml) was added followed by 4-hydroxy-4-pyridin-2-ylcyclohexanone (120 mg) and magnesium sulphate (30 mg). After 45 minutes, sodium triacetoxyborohydride (266 mg) was added and stirring continued overnight. Methanol (10 ml) was added and the mixture adsorbed onto silica for purification by chromatography eluting with 0-10% methanol/dichloromethane. This gave the faster running isomer of tert-butyl (2R)-2-{[4-(3,4-dichlorophenyl)piperazin-1-yl]carbonyl}-4-(4-hydroxy-4-pyridin-2-ylcyclohexyl)piperazine-1-carboxylate as a colourless glass (PH16781-089-01, 50 mg, 13%) and the slower running isomer also as a colourless glass (PH16781-089-02, 80 mg, 21%). For PH16781-089-01:

LCMS M/z(+) 617.82 (M+H⁺).

¹H NMR (400.132 MHz, DMSO-d₆) 1.3 (s, 9H), 1.8 (m, 8H), 2.2-3.7 (m, 16H), 4.8 (m, 1H), 6.9 (d, 1H), 7.1 (s, 1H), 7.25 (m, 1H), 7.4 (d, 1H), 7.5 (d, 1H), 7.8 (m, 1H), 8.5 (m, 1H).

4-Hydroxy-4-pyridin-2-ylcyclohexanone

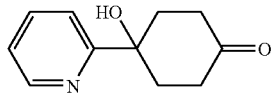

8-Pyridin-2-yl-1,4-dioxaspiro[4.5]decan-8-ol (1.44 g) was dissolved in tetrahydrofuran (25 ml). 2M hydrochloric acid (25 ml) was added and the solution stirred at room temperature overnight. The THF was removed in vacuo and remaining solution made basic with 2M aqueous sodium hydroxide and partitioned with dichloromethane (2×100 ml). Combined organics were dried (sodium sulphate) and concentrated in vacuo to give 4-hydroxy-4-pyridin-2-ylcyclohexanone as an off-white solid (1.07 g, 92%).

LCMS M/z(+) 192.04 (M+H⁺).

¹H NMR (400.132 MHz, DMSO-d₆) 1.9 (m, 2H), 2.15 (m, 2H), 2.3 (m, 2H), 2.7 (m, 2H), 5.6 (s, 1H), 7.25 (m, 1H), 7.8 (m, 2H), 8.5 (d, 1H).

8-Pyridin-2-yl-1,4-dioxaspiro[4.5]decan-8-ol

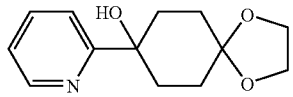

A mixture of n-butyllithium (1.6 M in hexanes, 8.8 ml) and anhydrous ether (20 ml) was stirred at −78° C. under argon and a solution of 2-bromopyridine (1.22 ml) in anhydrous ether (20 ml) added dropwise over 10 minutes. The resulting deep red solution was stirred for 10 minutes and a solution of cyclohexanedione monoethylene ketal (2 g) in tetrahydrofuran (20 ml) then introduced dropwise over 10 minutes. The resulting green suspension was maintained at −78° C. for one hour then warmed to −20° C. and stirred for a further hour, after which a yellow solution had formed. The reaction was quenched with saturated aqueous ammonium chloride (60 ml) and the layers separated. The aqueous was partitioned with dichloromethane (2×80 ml) and combined organics were dried (sodium sulphate) and concentrated in vacuo to give a yellow oil. This was adsorbed onto silica for purification by chromatography eluting with 0-100% ethyl acetate/isohexane to give 8-pyridin-2-yl-1,4-dioxaspiro[4.5]decan-8-ol as a pale yellow solid (1.45 g, 48%).

LCMS M/z(+) 236.04 (M+H⁺).

¹H NMR (400.132 MHz, DMSO-d₆) 1.55 (d, 4H), 1.9 (m, 2H), 2.2 (m, 2H), 3.85 (s, 4H), 5.05 (s, 1H), 7.2 (m, 1H), 7.65 (d, 1H), 7.75 (t, 1H), 8.45 (d, 1H).

Particular Compounds of the Invention Are:

1-[(1-cyclopropylpiperidin-3-yl)carbonyl]-4-(3,4-dichlorophenyl)piperazine
1-[(1-cyclopropylpiperidin-3-yl)carbonyl]-4-[4-(trifluoromethyl)phenyl]piperazine
1-[(1-cyclopropylpiperidin-3-yl)carbonyl]-4-[5-(trifluoromethyl)pyridin-2-yl]piperazine
4-{4-[(1-cyclopropylpiperidin-3-yl)carbonyl]piperazin-1-yl}-2-methylpyrimidine
1-(5-chloropyridin-2-yl)-4-[(1-cyclopropylpiperidin-3-yl)carbonyl]piperazine
1-[(1-cyclopropylpiperidin-3-yl)methyl]-4-(3,4-dichlorophenyl)piperazine
1-[(1-cyclopropylpiperidin-3-yl)methyl]-4-(3,5-dichlorophenyl)piperazine
1-[(1-cyclopropylpiperidin-3-yl)methyl]-4-pyridin-4-ylpiperazine
1-[(1-cyclopropylpiperidin-3-yl)methyl]-4-[4-(trifluoromethyl)phenyl]piperazine
1-[(1-cyclopropylpiperidin-3-yl)methyl]-4-[5-(trifluoromethyl)pyridin-2-yl]piperazine
1-(5-chloropyridin-2-yl)-4-[(1-cyclopropylpiperidin-3-yl)methyl]piperazine
1-(4-tert-butylphenyl)-4-[(1-cyclopropylpiperidin-3-yl)methyl]piperazine
1-[(1-cyclopropylpiperidin-3-yl)methyl]-4-[4-(trifluoromethoxy)phenyl]piperazine
(3R)-1-isopropyl-3-({4-[5-(trifluoromethyl)pyridin-2-yl]piperazin-1-yl}carbonyl)piperazine
(3R)-3-{[4-(4-tert-butylphenyl)piperazin-1-yl]carbonyl}-1-isopropyl piperazine
(3R)-3-{[4-(2,3-dichlorophenyl)piperazin-1-yl]carbonyl}-1-isopropyl piperazine
(3R)-3-{[4-(3,4-dimethylphenyl)piperazin-1-yl]carbonyl}-1-isopropyl piperazine
(3R)-3-{[4-(3-chloro-4-fluorophenyl)piperazin-1-yl]carbonyl}-1-isopropyl piperazine
(3R)-3-{[4-(5-chloropyridin-2-yl)piperazin-1-yl]carbonyl}-1-isopropyl piperazine
2-(4-{[(2R)-4-isopropylpiperazin-2-yl]carbonyl}piperazin-1-yl)-4-(trifluoromethyl)pyrimidine
(3R)-3-{[4-(3-chlorophenyl)piperazin-1-yl]carbonyl}-1-isopropylpiperazine
(3R)-3-{[4-(3,4-dichlorophenyl)piperazin-1-yl]carbonyl}-1-isopropyl piperazine
2-(4-{[(2R)-4-ethylpiperazin-2-yl]carbonyl}piperazin-1-yl)quinoline
(3R)-1-isopropyl-3-({4-[4-(trifluoromethyl)phenyl]piperazin-1-yl}carbonyl)piperazine
(3R)-3-{[4-(4-chlorophenyl)piperazin-1-yl]carbonyl}-1-isopropylpiperazine
(3R)-3-{[4-(3,4-dichlorophenyl)piperazin-1-yl]carbonyl}-1-methyl piperazine
(3R)-3-{[4-(3,4-dichlorophenyl)piperazin-1-yl]carbonyl}-1-ethyl piperazine
(3R)-3-{[4-(4-chlorophenyl)piperidin-1-yl]carbonyl}-1-isopropylpiperazine
(3R)-3-{[4-(4-chlorophenyl)-3,6-dihydropyridin-1(2H)-yl]carbonyl}-1-isopropylpiperazine
2-(4-{[(2R)-4-isopropylpiperazin-2-yl]carbonyl}piperazin-1-yl)-1H-benzimidazole 5-chloro-2-(4-{[(2R)-4-isopropylpiperazin-2-yl]carbonyl}piperazin-1-yl)-1H-benzimidazole
(2R,S)-1-(3,4-dichlorophenyl)-4-(piperazin-2-ylcarbonyl)piperazine
(3R)-1-cyclopropyl-3-{[4-(3,4-dichlorophenyl)piperazin-1-yl]carbonyl}piperazine
(2R)-1-(3,4-dichlorophenyl)-4-[piperazin-2-ylcarbonyl]piperazine
2-(4-{[(2R)-4-ethylpiperazin-2-yl]carbonyl}piperazin-1-yl)-1,3-benzothiazole
(3R,S)-1-[(1-ethylpiperidin-3-yl)methyl]-4-[3-(trifluoromethyl)phenyl]piperazine (3R,S)-1-benzyl-3-{[4-(3,4-dichlorophenyl)piperazin-1-yl]carbonyl}piperazine
(3R,S)-3-{[4-(3,4-dichlorophenyl)piperazin-1-yl]carbonyl}-1-isopropylpiperazine
(3R)-1-(cyclopropylmethyl)-3-{[4-(3,4-dichlorophenyl)piperazin-1-yl]carbonyl}piperazine
(3R)-1-cyclohexyl-3-{[4-(3,4-dichlorophenyl)piperazin-1-yl]carbonyl}piperazine
(3R)-1-cyclopentyl-3-{[4-(3,4-dichlorophenyl)piperazin-1-yl]carbonyl}piperazine
2-[3-((3R)-3-{[4-(3,4-dichlorophenyl)piperazin-1-yl]carbonyl}piperazin-1-yl)propyl]-5-fluoropyrimidine
(3R)-3-{[4-(3,4-dichlorophenyl)piperazin-1-yl]carbonyl}-1-(tetrahydrofuran-3-ylmethyl)piperazine
(3R)-3-{[4-(3,4-dichlorophenyl)piperazin-1-yl]carbonyl}-1-(4,4,4-trifluorobutyl)piperazine
(3R)-3-{[4-(3,4-dichlorophenyl)piperazin-1-yl]carbonyl}-1-(3,3,3-trifluoropropyl)piperazine
(3R)-3-{[4-(3,4-dichlorophenyl)piperazin-1-yl]carbonyl}-1-(1-ethylpropyl)piperazine
(3R)-3-{[4-(3,4-dichlorophenyl)piperazin-1-yl]carbonyl}-1-(1-methylbutyl)piperazine
(3R,S)-1-({1-[2-phenyl]ethyl}piperidin-3-ylmethyl)-4-(2-quinolinyl)piperazine
(3R)-1-({1-[2-phenyl]ethyl}piperidin-3-ylmethyl)-4-(2-quinolinyl)piperazine
(3R)-4-(6-bromoquinazolin-2-yl)-1-({1-[2-phenyl]ethyl}piperidin-3-ylmethyl)piperazine
(3R)-4-(6-bromoquinolin-2-yl)-1-({1-[2-phenyl]ethyl}piperidin-3-ylmethyl)piperazine
(3R)-4-(3-methylquinolin-2-yl)-1-({1-[2-phenyl]ethyl}piperidin-3-ylmethyl)piperazine
(3R)-4-(8-chloroquinolin-2-yl)-1-({1-[2-phenyl]ethyl}piperidin-3-ylmethyl)piperazine
(3R)-4-(quinoxalin-2-yl)-1-({1-[2-phenyl]ethyl}piperidin-3-ylmethyl)piperazine
(3R)-4-(3-methylquinoxalin-2-yl)-1-({1-[2-phenyl]ethyl}piperidin-3-ylmethyl)piperazine
(3R)-4-(1,8-naphthyridin-2-yl)-1-({1-[2-phenyl]ethyl}piperidin-3-ylmethyl)piperazine
(3R)-1-({1-cyclopropyl}piperidin-3-ylmethyl)-4-(2-quinolinyl)piperazine
(3R)-3-{[4-(4-fluorophenyl)piperazin-1-yl]carbonyl}-1-isopropylpiperazine
(3R)-1-isopropyl-3-{[4-(3-methylphenyl)piperazin-1-yl]carbonyl}piperazine
(3R)-3-{[4-(3,5-dichlorophenyl)piperazin-1-yl]carbonyl}-1-isopropylpiperazine
(3R)-1-isopropyl-3-{[4-(4-methylphenyl)piperazin-1-yl]carbonyl}piperazine
(3R)-1-isopropyl-3-({4-[3-(trifluoromethyl)phenyl]piperazin-1-yl}carbonyl)piperazine
(3R)-3-({4-[4-(benzyloxy)phenyl]piperazin-1-yl}carbonyl)-1-isopropylpiperazine
(3R)-3-{[4-(2,4-difluorophenyl)piperazin-1-yl]carbonyl}-1-isopropylpiperazine
(3R)-3-({4-[3-chloro-5-(trifluoromethyl)pyridin-2-yl]piperazin-1-yl}carbonyl)-1-isopropylpiperazine
(3R)-3-[(4-biphenyl-4-ylpiperazin-1-yl)carbonyl]-1-isopropylpiperazine
(3R)-1-isopropyl-3-({4-[4-(trifluoromethoxy)phenyl]piperazin-1-yl}carbonyl)piperazine
(3R)-3-{[4-(5-bromopyridin-2-yl)piperazin-1-yl]carbonyl}-1-isopropylpiperazine
(3R)-3-{[4-(3,4-difluorophenyl)piperazin-1-yl]carbonyl}-1-isopropyl piperazine
(3R)-1-isopropyl-3-[(4-phenylpiperazin-1-yl)carbonyl]piperazine
(3R)-3-{[4-(2-fluorophenyl)piperazin-1-yl]carbonyl}-1-isopropylpiperazine
(3R)-3-{[4-(3,5-dichloropyridin-4-yl)piperazin-1-yl]carbonyl}-1-isopropylpiperazine
(3R)-1-isopropyl-3-[(4-pyridin-2-ylpiperazin-1-yl)carbonyl]piperazine
2-(4-{[(2R)-4-isopropylpiperazin-2-yl]carbonyl}piperazin-1-yl)benzonitrile
(3R)-1-isopropyl-3-{[4-(2-methylphenyl)piperazin-1-yl]carbonyl}piperazine
(3R)-1-isopropyl-3-({4-[2-(methylthio)phenyl]piperazin-1-yl}carbonyl)piperazine
(3R)-3-{[4-(2,3-dimethylphenyl)piperazin-1-yl]carbonyl}-1-isopropylpiperazine
5-(4-ethoxyphenyl)-2-(4-{[(2R)-4-isopropylpiperazin-2-yl]carbonyl}piperazin-1-yl)pyrimidine
(3R)-1-isopropyl-3-[(4-{3-[3-(trifluoro methyl)phenyl]-1,2,4-oxadiazol-5-yl}piperidin-1-yl)carbonyl]piperazine
(3R)-3-{[4-(3,4-dichlorophenyl)piperazin-1-yl]carbonyl}-1-(prop-2-en-1-yl)piperazine
(3R)-3-{[4-(3,4-dichlorophenyl)piperazin-1-yl]carbonyl}-1-(2-methylprop-2-en-1-yl)piperazine
(3R)-3-{[4-(3,4-dichlorophenyl)piperazin-1-yl]carbonyl}-1-(prop-2-yn-1-yl)piperazine
(3R)-3-{[4-(3-chlorophenyl)-2-methylpiperazin-1-yl]carbonyl}-1-isopropylpiperazine
(3R)-3-{[4-(4-phenyl-1,2,4-thiadiazol-2-yl)piperazin-1-yl]carbonyl}-1-(isopropyl)piperazine
(3R,3S)-3-{[4-(3-Chloro-4-fluorophenyl)piperazin-1-yl]carbonyl}-1-tert-butyl piperazine
(3R)-3-{[4-(3-Chloro-4-fluorophenyl)piperazin-1-yl]carbonyl}-1-tert-butyl piperazine
[4-(3,4-dichlorophenyl)piperazin-1-yl]-((2R,2S)-4-tert-butylpiperazin-2-yl)methanone
[4-(3,4-Dichlorophenyl)piperazin-1-yl]-[(2R)-4-tert-butylpiperazin-2-yl]methanone
[4-(3,4-Dichlorophenyl)piperazin-1-yl]-[(2S)-4-tert-butylpiperazin-2-yl]methanone
[4-(3,4-Dichlorophenyl)piperazin-1-yl]-[(2R,2S)-4-(2-methylbutan-2-yl)piperazin-2-yl]methanone
[4-(3,4-Dichlorophenyl)piperazin-1-yl]-[(2S)-4-(2-methylbutan-2-yl)piperazin-2-yl]methanone
[4-(3,4-Dichlorophenyl)piperazin-1-yl]-[(2R)-4-(2-methylbutan-2-yl)piperazin-2-yl]methanone
[4-(5-Chloro-1H-benzoimidazol-2-yl)piperazin-1-yl]-((2R,2S)-4-tert-butylpiperazin-2-yl)methanone
4-((3R)-3-{[4-(3,4-dichlorophenyl)piperazin-1-yl]carbonyl}piperazin-1-yl)-1-pyridin-2-ylcyclohexanol
Particular Intermediates are:
2-{4-[(1-cyclopropylpiperidin-3-yl)carbonyl]piperazin-1-yl}pyrazine
1-[(1-cyclopropylpiperidin-3-yl)carbonyl]-4-(3,5-dichlorophenyl)piperazine
1-[(1-cyclopropylpiperidin-3-yl)carbonyl]-4-pyridin-2-ylpiperazine
1-[(1-cyclopropylpiperidin-3-yl)carbonyl]-4-pyridin-4-ylpiperazine
4-{4-[(1-cyclopropylpiperidin-3-yl)carbonyl]piperazin-1-yl}benzonitrile
4-{4-[(1-cyclopropylpiperidin-3-yl)carbonyl]piperazin-1-yl}-2-methyl quinoline
1-(4-tert-butylphenyl)-4-[(1-cyclopropylpiperidin-3-yl)carbonyl]piperazine
1-[(1-cyclopropylpiperidin-3-yl)carbonyl]-4-[4-(trifluoromethoxy)phenyl]piperazine 1-[(1-cyclopropylpiperidin-3-yl)carbonyl]-4-[4-(methylsulfonyl)phenyl]piperazine (3R)-3-{[4-(3,4-dimethoxyphenyl)piperazin-1-yl]carbonyl}-1-isopropyl piperazine (3R)-3-{[4-(5-ethoxypyridin-2-yl)piperazin-1-yl]carbonyl}-1-isopropyl piperazine (3R)-4-tert-butoxycarbonyl-3-{[4-(3,4-dichlorophenyl)piperazin-1-yl]carbonyl}-1-(prop-2-en-1-yl)piperazine (3R)-4-tert-butoxycarbonyl-3-{[4-(3,4-dichlorophenyl)piperazin-1-yl]carbonyl}-1-(2-methylprop-2-en-1-yl)piperazine tert-butyl (2R)-4-(cyclopropylmethyl)-2-{[4-(3,4-dichlorophenyl)piperazin-1-yl]carbonyl}piperazine-1-carboxylate tert-butyl (2R)-4-cyclohexyl-2-{[4-(3,4-dichlorophenyl)piperazin-1-yl]carbonyl}piperazine-1-carboxylate tert-butyl (2R)-4-cyclopentyl-2-{[4-(3,4-dichlorophenyl)piperazin-1-yl]carbonyl}piperazine-1-carboxylate tert-butyl (2R)-2-{[4-(3,4-dichlorophenyl)piperazin-1-yl]carbonyl}-4-[3-(5-fluoro pyrimidin-2-yl)propyl]piperazine-1-carboxylate tert-butyl (2R)-2-{[4-(3,4-dichlorophenyl)piperazin-1-yl]carbonyl}-4-(tetrahydro furan-3-ylmethyl)piperazine-1-carboxylate tert-butyl (2R)-2-{[4-(3,4-dichlorophenyl)piperazin-1-yl]carbonyl}-4-(4,4,4-trifluorobutyl)piperazine-1-carboxylate tert-butyl (2R)-2-{[4-(3,4-dichlorophenyl)piperazin-1-yl]carbonyl}-4-(3,3,3-trifluoropropyl)piperazine-1-carboxylate tert-butyl (2R)-2-{[4-(3,4-dichlorophenyl)piperazin-1-yl]carbonyl}-4-(1-ethyl propyl)piperazine-1-carboxylate tert-butyl (2R)-2-{[4-(3,4-dichlorophenyl)piperazin-1-yl]carbonyl}-(1,R,S)-4-(1-methylbutyl)piperazine-1-carboxylate tert-butyl (2R)-2-{[4-(1,3-benzothiazol-2-yl)piperazin-1-yl]carbonyl}-4-ethylpiperazine-1-carboxylate tert-butyl (2R)-2-{[4-(3,4-dichlorophenyl)piperazin-1-yl]carbonyl}-4-(prop-2-yn-1-yl)piperazine-1-carboxylate tert-butyl (2R,2'-unspecified)-2-{[4-(3-chlorophenyl)-2'-methylpiperazin-1-yl]carbonyl}-4-isopropylpiperazine-1-carboxylate tert-Butyl (2R)-2-{[4-(4-phenyl-1,2,4-thiadiazol-2-yl)piperazin-1-yl]carbonyl}-4-isopropyl piperazine-1-carboxylate tert-Butyl (2R,2S)-2-{[4-(3-Chloro-4-fluorophenyl)piperazin-1-yl]carbonyl}-4-tert-butylpiperazine-1-carboxylate tert-Butyl (2R,2S)-2-[4-(3,4-dichlorophenyl)piperazine-1-carbonyl]-4-tert-butylpiperazine-1-carboxylate tert-Butyl (2R,2S)-2-[4-(3,4-dichlorophenyl)piperazine-1-carbonyl]-4-(2-methylbutan-2-yl)piperazine-1-carboxylate tert-Butyl (2R,2S)-2-[4-(5-chloro-1H-benzoimidazol-2-yl)piperazine-1-carbonyl]-4-tert-butyl-piperazine-1-carboxylate tert-Butyl (2R)-2-{[4-(3,4-dichlorophenyl)piperazin-1-yl]carbonyl}-4-(4-hydroxy-4-pyridin-2-ylcyclohexyl)piperazine-1-carboxylate Pharmaceutical Compositions This Example illustrates, but is not intended to limit, representative pharmaceutical dosage forms of the invention as defined herein (the active ingredient being termed "Compound X"), for therapeutic or prophylactic use in humans:

Example A

| (a) | |
|---|---|
| Tablet I | mg/tablet |
| Compound X. | 100 |
| Lactose Ph.Eur | 182.75 |
| Croscarmellose sodium | 12.0 |
| Maize starch paste (5% w/v paste) | 2.25 |
| Magnesium stearate | 3.0 |

| (b) | |
|---|---|
| Tablet II | mg/tablet |
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c) | |
|---|---|
| Tablet III | mg/tablet |
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

| (d) | |
|---|---|
| Capsule | mg/capsule |
| Compound X | 10 |
| Lactose Ph.Eur | 488.5 |
| Magnesium | 1.5 |

| (e) | |
|---|---|
| Injection I | (50 mg/ml) |
| Compound X | 5.0% w/v |
| 1M Sodium hydroxide solution | 15.0% v/v |
| 0.1M Hydrochloric acid | to adjust pH to 7.6 |
| Polyethylene glycol 400 | 4.5% w/v |
| Water for injection | to 100% |

| (f) | |
|---|---|
| Injection II | (10 mg/ml) |
| Compound X | 1.0% w/v |
| Sodium phosphate BP | 3.6% w/v |
| 0.1M Sodium hydroxide solution | 15.0% v/v |
| Water for injection | to 100% |

| (g) | |
|---|---|
| Injection III | (1 mg/ml, buffered to pH 6) |
| Compound X | 0.1% w/v |
| Sodium phosphate BP | 2.26% w/v |
| Citric acid | 0.38% w/v |
| Polyethylene glycol 400 | 3.5% w/v |
| Water for injection | to 100% |

-continued (h)

| Aerosol I | mg/ml |
|---|---|
| Compound X | 10.0 |
| Sorbitan trioleate | 13.5 |
| Trichlorofluoromethane | 910.0 |
| Dichlorodifluoromethane | 490.0 |

(i)

| Aerosol II | mg/ml |
|---|---|
| Compound X | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |

(j)

| Aerosol III | mg/ml |
|---|---|
| Compound X | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |

(k)

| Aerosol IV | mg/ml |
|---|---|
| Compound X | 2.5 |
| Soya lecithin | 2.7 |
| Trichlorofluoromethane | 67.5 |
| Dichlorodifluoromethane | 1086.0 |
| Dichlorotetrafluoroethane | 191.6 |

(l)

| Ointment | ml |
|---|---|
| Compound X | 40 mg |
| Ethanol | 300 μl |
| Water | 300 μl |
| 1-Dodecylazacycloheptan-2-one | 50 μl |
| Propylene glycol | to 1 ml |

Note:
Compound X in the above formulations may comprise a compound as illustrated in herein.

The above formulations may be obtained by conventional procedures well known in the pharmaceutical art. The tablets (a)-(c) may be enteric coated by conventional means, for example to provide a coating of cellulose acetate phthalate. The aerosol formulations (h)-(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

The invention claimed is:
1. A compound of Formula I

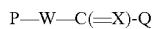

P—W—C(=X)-Q   (I), or a pharmaceutically acceptable salt thereof
wherein
P is a monocyclic or bicyclic $C_{5-10}$ aryl or heteroaryl group of up to 20 ring atoms, each of which is optionally substituted by 1, 2 or 3 substituents independently selected from halogen, $C_{1-4}$ alkyl, $C_{3-6}$ cycloalkyl, $C_{2-4}$ alkenyl or $C_{2-4}$ alkynyl, cyano, phenyl, phenoxy, —O—$C_{1-4}$ alkyl, $C_{1-4}$ thioalkyl, carboxy, carboxy $C_{1-4}$ alkyl, —SO$_2$CH$_3$, $C_{1-4}$ alkylamino and NO$_2$; and wherein $C_{1-4}$ alkyl, —O—$C_{1-4}$ alkyl, or $C_{1-4}$ thioalkyl is optionally substituted by one or more fluorine atoms and wherein the phenyl or phenoxy substituent may in turn be substituted by 1,2, or 3 of the other substituents listed above for P;

W is a piperazine or homopiperazine ring optionally substituted on any ring carbon atom by group independently selected from $C_{1-4}$ alkyl, =O and halogen X is two hydrogen atoms each linked by a single bond to the carbon atom in —C(=X); and Q is a 4-7 membered aliphatic ring comprising one nitrogen atom and Q is linked to —C(=X)— via a ring carbon atom, such aliphatic ring being (i) optionally monosubstituted on the ring nitrogen atom by a $C_{1-4}$ alkyl group which may be further optionally substituted by difluoromethyl, trifluoromethyl, a monocyclic aliphatic or (hetero)aromatic ring of up to 7 ring atoms and comprising up to three heteroatoms each independently selected from N, O or S and the ring being optionally substituted by 1, 2 or 3 substituents independently selected from halogen $C_{1-4}$ alkyl, cyano, —O—$C_{1-4}$ alkyl, $C_{1-4}$ thioalkyl, —SO$_2$CH$_3$, $C_{1-4}$ alkylamino and NO$_2$ and wherein $C_{1-4}$ alkyl, —O—$C_{1-4}$ alkyl, or $C_{1-4}$ thioalkyl is optionally substituted by one or more fluorine atoms; and/or (ii) optionally monosubstituted on the nitrogen atom by a monocyclic (hetero)aliphatic or (hetero)aromatic ring of up to 7 ring atoms and comprising up to three heteroatoms each independently selected from N, O or S and the ring being optionally substituted by 1, 2 or 3 substituents independently selected from halogen, $C_{1-4}$ alkyl, cyano —O—$C_{1-4}$ alkyl, $C_{1-4}$ thioalkyl, —SO$_2$CH$_3$, $C_{1-4}$ alkylamino and NO$_2$; and/or (iii) optionally substituted on the ring nitrogen atom by a (hetero)aryl-$C_{1-4}$ alkyl group comprising up to 8 ring atoms of which up to 3 may be heteroatoms independently selected from N, O and S, such group being optionally substituted by up to 3 substituents independently selected from halogen, $C_{1-4}$ alkyl, $C_{2-4}$ alkenyl or $C_{2-4}$ alkynyl, cyano, phenyl, phenoxy, $C_{1-4}$ thioalkyl, carboxy $C_{1-4}$ alkyl, —SO$_2$CH$_3$ and NO$_2$, and wherein $C_{1-4}$ alkyl, —O—$C_{1-4}$ alkyl, or $C_{1-4}$ thioalkyl is optionally substituted by one or more fluorine atoms and wherein the phenyl or phenoxy substituent may in turn be substituted by 1, 2, or 3 of the other substituents listed above; and/or (iv) optionally substituted on the ring nitrogen atom by a straight or branched chain alkyl group of up to 8 (such as up to 6) carbon atoms optionally comprising a double or treble carbon-carbon bond and further optionally substituted by up to 2 substituents independently selected from hydroxy, CF$_3$, $C_{3-7}$ cycloalkyl or —NR$^1$R$^2$ wherein R$^1$ and R$^2$ are independently selected from hydrogen or any ring substituent listed hereinbefore for Q; and/or (v) optionally mono-substituted on one or more ring carbon atoms by halogen, —CN or a $C_{1-4}$ alkyl group which is optionally by hydroxy or a —O—$C_{1-4}$ alkyl group, and/or (vi) optionally disubstituted on ring carbon atom by $C_{1-4}$ alkyl groups or by a single spiro group having up to 5 carbon atoms, such groups being optionally substituted by a —O—$C_{1-4}$ alkyl group;

provided that formula 1 is not
(i) 1-(2-methoxyphenyl)-4-(piperidin-4-ylmethyl)piperazine;

(ii) 4-(4((1-methylpiperidin-4-yl)methyl)piperazin-1-yl)-1H-indole, or (iii) 1-(2-methoxyphenyl)-4-(piperidin-3-ylmethyl)piperazine.

2. The compound as claimed in claim 1 wherein P is a monocyclic or bicyclic $C_{5-10}$ aryl group or a heteroaryl group of up to 12 ring atoms, each of which is optionally substituted by 1 or 2 substituents independently selected from halogen, $C_{1-4}$ alkyl, $C_{3-6}$ cycloalkyl, $C_{2-4}$ alkenyl or $C_{2-4}$ alkynyl, cyano, phenyl, phenoxy, —O—$C_{1-4}$ alkyl, $C_{1-4}$ thioalkyl, carboxy, carboxy $C_{1-4}$ alkyl, —$SO_2CH_3$, $C_{1-4}$ alkylamino and $NO_2$; and wherein $C_{1-4}$ alkyl, —O—$C_{1-4}$ alkyl, or $C_{1-4}$ thioalkyl is optionally substituted by one or more fluorine atoms and wherein the phenyl or phenoxy substituent may in turn be substituted by 1,2, or 3 of the other substituents listed above for P, or a pharmaceutically acceptable salt thereof.

3. The compound as claimed in claim 1, wherein W is a piperazine.

4. The compound as claimed in claim 2, wherein W is a piperazine.

5. The compound as claimed in claim 1 wherein P is a phenyl or naphthyl or a heteroaryl group of up to 10 ring atoms optionally substituted by 1 or 2 substituents independently selected from halogen, $C_{1-4}$ alkyl, cyano, $C_{1-4}$ alkyl or $C_{1-4}$ alkoxy optionally substituted by up to 3 halogen atoms, phenyl, phenoxy, —O—$C_{1-4}$alkyl, $C_{1-4}$thioalkyl, $SO_2CH_3$, $C_{1-4}$alkylamino, and $NO_2$; and wherein the phenyl, phenoxy substituent is optionally substituted by 1 or 2 substituents independently selected from halogen $C_{1-4}$alkyl, cyano, $C_{1-4}$alkyl or $C_{1-4}$alkoxy optionally substituted by up to 3 halogen atoms, —O—$C_{1-4}$alkyl, $C_{1-4}$thioalkyl, $SO_2CH_3$, $C_{1-4}$alkylamino, and $NO_2$.

6. A pharmaceutical composition comprising a compound of the formula I as claimed in claim 1 in association with a pharmaceutically-acceptable diluent or carrier.

7. A pharmaceutical composition comprising a compound of the formula I as claimed in claim 2 in association with a pharmaceutically-acceptable diluent or carrier.

8. A pharmaceutical composition comprising a compound of the formula I as claimed in claim 5 in association with a pharmaceutically-acceptable diluent or carrier.

9. The compound as claimed in claim 3, wherein P is a phenyl or naphthyl or a heteroaryl group of up to 10 ring atoms optionally substituted by 1 or 2 substituents independently selected from halogen, $C_{1-4}$alkyl, cyano, $C_{1-4}$alkyl or $C_{1-4}$alkoxy optionally substituted by up to 3 halogen atoms, phenyl, phenoxy, —O—$C_{1-4}$alkyl, $C_{1-4}$thioalkyl, $SO_2CH_3$, $C_{1-4}$alkylamino, and $NO_2$; and wherein the phenyl or phenoxy substituent is optionally substituted by 1 or 2 substituents independently selected from halogen, $C_{1-4}$alkyl, cyano, $C_{1-4}$alkyl or $C_{1-4}$alkoxy optionally substituted by up to 3 halogen atoms, —O—$C_{1-4}$alkyl, $C_{1-4}$thioalkyl, $SO_2CH_3$, $C_{1-4}$alkylamino, and $NO_2$.

10. A pharmaceutical composition comprising a compound of the formula I as claimed in claim 9 in association with a pharmaceutically-acceptable diluent or carrier.

* * * * *